(12) United States Patent
Birk et al.

(10) Patent No.: US 8,323,180 B2
(45) Date of Patent: Dec. 4, 2012

(54) HYDRAULIC GASTRIC BAND WITH COLLAPSIBLE RESERVOIR

(75) Inventors: Janel A. Birk, Oxnard, CA (US); Ethan Franklin, Goleta, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/184,456

(22) Filed: Jul. 15, 2011

(65) Prior Publication Data

US 2011/0270030 A1    Nov. 3, 2011

Related U.S. Application Data

(63) Continuation of application No. 12/850,038, filed on Aug. 4, 2010, which is a continuation of application No. 11/754,091, filed on May 25, 2007, now Pat. No. 7,798,954, which is a continuation-in-part of application No. 11/472,902, filed on Jun. 22, 2006, now Pat. No. 8,043,206, which is a continuation-in-part of application No. PCT/US2006/000013, filed on Jan. 4, 2006.

(51) Int. Cl.
A61B 17/00 (2006.01)
(52) U.S. Cl. .......................................... 600/37
(58) Field of Classification Search .............. 600/29–31, 600/37; 606/151–158; 604/8–10, 19–45; A61B 17/08, 17/12, 17/135
See application file for complete search history.

(56) References Cited

U.S. PATENT DOCUMENTS

| 1,174,814 A | 3/1916 | Brennan et al. |
| 1,830,947 A | 11/1931 | Klingel |
| 1,999,683 A | 4/1935 | Borresen |
| 2,163,048 A | 6/1939 | McKee |
| 2,339,138 A | 1/1944 | Black |
| 2,405,667 A | 8/1946 | Ottesen |
| 2,438,231 A | 3/1948 | Schultz et al. |
| 2,635,907 A | 4/1953 | Heimbuch |
| 2,714,469 A | 8/1955 | Carlson |

(Continued)

FOREIGN PATENT DOCUMENTS

CA          949965          6/1974
(Continued)

OTHER PUBLICATIONS

Bio Enterics Lap-Band Adjustable Gastric Banding System, Inamed Health, pub. Aug. 28, 2003, pp. 1-115.

(Continued)

Primary Examiner — Charles A Marmor, II
Assistant Examiner — Catherine E Burk
(74) Attorney, Agent, or Firm — Stephen Donovan; Debra Condino

(57) ABSTRACT

A self-regulating gastric band apparatus for adjusting stoma size. The apparatus includes an adjustable gastric band with an expandable inner ring. A band adjustment assembly includes a sensor for sensing fluid pressure in the inner ring and a pump assembly connected to the inner ring and to a controller for adjusting the volume of the fluid in the band based on the sensed fluid pressure. A memory stores an operating range of a target fluid pressure, and the pump assembly maintains the sensed band pressure within the operating range. An elongated fluid reservoir extends along part of a fill tube. An expandable fluid reservoir stores a volume of the fluid for adjusting the volume of fluid in the lumen. A protective outer sheath is provided around the exterior of an expandable fluid reservoir in both a first, deflated state, and a second, inflated state of the reservoir.

20 Claims, 24 Drawing Sheets

U.S. PATENT DOCUMENTS

| | | | |
|---|---|---|---|
| 2,936,980 A | 5/1960 | Rapata | |
| 3,059,645 A | 10/1962 | Hasbrouck et al. | |
| 3,189,961 A | 6/1965 | Heller | |
| 3,667,081 A | 6/1972 | Burger | |
| 3,840,018 A | 10/1974 | Heifetz | |
| 3,955,834 A | 5/1976 | Ahlrot | |
| 4,053,176 A | 10/1977 | Hilbush | |
| 4,117,727 A | 10/1978 | Friswell et al. | |
| 4,118,805 A | 10/1978 | Reimels | |
| 4,133,315 A | 1/1979 | Berman et al. | |
| 4,157,713 A | 6/1979 | Clarey | |
| 4,176,412 A | 12/1979 | Peterson | |
| 4,236,521 A | 12/1980 | Lauterjung | |
| 4,271,827 A | 6/1981 | Angelchick | |
| 4,286,584 A | 9/1981 | Sampson et al. | |
| 4,299,012 A | 11/1981 | Oetiker | |
| 4,370,982 A | 2/1983 | Reilly | |
| 4,399,809 A | 8/1983 | Baro et al. | |
| 4,406,656 A * | 9/1983 | Hattler et al. | 604/523 |
| 4,408,597 A | 10/1983 | Tenney, Jr. et al. | |
| 4,417,567 A | 11/1983 | Trick | |
| 4,424,208 A | 1/1984 | Wallace et al. | |
| 4,442,153 A | 4/1984 | Meltsch | |
| 4,485,805 A | 12/1984 | Foster, Jr. | |
| 4,492,004 A | 1/1985 | Oetiker | |
| 4,551,862 A | 11/1985 | Haber | |
| 4,558,699 A | 12/1985 | Bashour | |
| 4,559,699 A | 12/1985 | Owen et al. | |
| 4,582,640 A | 4/1986 | Smestad et al. | |
| 4,582,865 A | 4/1986 | Balazs et al. | |
| 4,592,339 A | 6/1986 | Kuzmak et al. | |
| 4,592,355 A | 6/1986 | Antebi | |
| 4,601,713 A | 7/1986 | Fuqua | |
| 4,603,699 A | 8/1986 | Himpens | |
| 4,671,351 A | 6/1987 | Rappe | |
| 4,693,695 A | 9/1987 | Cheng | |
| 4,694,827 A | 9/1987 | Weiner et al. | |
| 4,696,288 A | 9/1987 | Kuzmak et al. | |
| 4,708,140 A | 11/1987 | Baron | |
| 4,716,154 A | 12/1987 | Malson et al. | |
| 4,753,086 A | 6/1988 | Schmidt | |
| 4,760,837 A | 8/1988 | Petit | |
| 4,803,075 A | 2/1989 | Wallace et al. | |
| 4,858,619 A | 8/1989 | Toth | |
| 4,872,483 A | 10/1989 | Shah | |
| 4,881,939 A | 11/1989 | Newman | |
| 4,883,467 A | 11/1989 | Franetzki et al. | |
| 4,886,787 A | 12/1989 | De Belder et al. | |
| 4,896,787 A | 1/1990 | Delamour et al. | |
| 4,915,690 A | 4/1990 | Cone et al. | |
| 4,919,650 A | 4/1990 | Feingold et al. | |
| 4,925,446 A | 5/1990 | Garay et al. | |
| 4,944,659 A | 7/1990 | Labbe et al. | |
| 4,958,791 A | 9/1990 | Nakamura | |
| 4,969,899 A | 11/1990 | Cox, Jr. | |
| 4,989,756 A | 2/1991 | Kagamihara et al. | |
| 4,994,019 A | 2/1991 | Fernandez et al. | |
| 5,045,060 A | 9/1991 | Melsky et al. | |
| 5,074,868 A | 12/1991 | Kuzmak | |
| 5,084,061 A | 1/1992 | Gau et al. | |
| 5,089,019 A | 2/1992 | Grandjean | |
| 5,091,171 A | 2/1992 | Yu et al. | |
| 5,120,313 A | 6/1992 | Elftman | |
| 5,143,724 A | 9/1992 | Leshchiner et al. | |
| 5,152,770 A | 10/1992 | Bengmark et al. | |
| 5,160,338 A | 11/1992 | Vincent | |
| 5,188,609 A | 2/1993 | Bayless et al. | |
| 5,224,494 A | 7/1993 | Enhorning | |
| 5,226,429 A | 7/1993 | Kuzmak | |
| 5,246,456 A | 9/1993 | Wilkinson | |
| 5,246,698 A | 9/1993 | Leshchiner et al. | |
| 5,259,399 A | 11/1993 | Brown | |
| 5,277,333 A | 1/1994 | Shimano | |
| 5,318,533 A | 6/1994 | Adams et al. | |
| 5,326,349 A | 7/1994 | Baraff | |
| 5,356,883 A | 10/1994 | Kuo et al. | |
| 5,360,445 A | 11/1994 | Goldowsky | |
| 5,383,858 A | 1/1995 | Reilly et al. | |
| 5,391,156 A | 2/1995 | Hildwein et al. | |
| 5,399,351 A | 3/1995 | Leshchiner et al. | |
| 5,425,716 A | 6/1995 | Kawasaki et al. | |
| 5,449,363 A | 9/1995 | Brust et al. | |
| 5,449,368 A | 9/1995 | Kuzmak | |
| 5,458,568 A | 10/1995 | Racchini et al. | |
| 5,496,312 A | 3/1996 | Klicek | |
| 5,496,313 A | 3/1996 | Gentelia et al. | |
| 5,509,888 A | 4/1996 | Miller | |
| 5,531,716 A | 7/1996 | Luzio et al. | |
| 5,535,752 A | 7/1996 | Halperin et al. | |
| 5,554,113 A | 9/1996 | Novak et al. | |
| 5,562,714 A | 10/1996 | Grevious | |
| 5,569,839 A | 10/1996 | Ajot et al. | |
| 5,601,604 A | 2/1997 | Vincent | |
| 5,607,418 A | 3/1997 | Arzbaecher | |
| 5,633,001 A | 5/1997 | Agerup | |
| 5,649,546 A | 7/1997 | Steinbeck | |
| 5,653,718 A | 8/1997 | Yoon | |
| 5,658,298 A | 8/1997 | Vincent et al. | |
| 5,676,162 A | 10/1997 | Larson, Jr. et al. | |
| 5,681,284 A | 10/1997 | Hershowitz | |
| 5,695,504 A | 12/1997 | Gifford, III et al. | |
| 5,704,893 A | 1/1998 | Timm | |
| 5,713,911 A | 2/1998 | Racenet et al. | |
| 5,733,257 A | 3/1998 | Sternby | |
| 5,741,232 A | 4/1998 | Reilly et al. | |
| 5,748,200 A | 5/1998 | Funahashi | |
| 5,758,667 A | 6/1998 | Slettenmark | |
| 5,759,015 A | 6/1998 | Van Lintel et al. | |
| 5,766,232 A | 6/1998 | Grevious et al. | |
| 5,769,877 A | 6/1998 | Barreras, Sr. | |
| 5,785,295 A | 7/1998 | Tsai | |
| 5,795,333 A | 8/1998 | Reilly et al. | |
| 5,807,311 A * | 9/1998 | Palestrant | 604/28 |
| 5,808,203 A | 9/1998 | Nolan, Jr. et al. | |
| 5,817,113 A | 10/1998 | Gifford, III et al. | |
| 5,827,529 A | 10/1998 | Ono et al. | |
| 5,833,698 A | 11/1998 | Hinchliffe et al. | |
| 5,861,014 A | 1/1999 | Familoni | |
| RE36,176 E | 3/1999 | Kuzmak | |
| 5,886,042 A | 3/1999 | Yu et al. | |
| 5,891,089 A | 4/1999 | Katz et al. | |
| 5,904,697 A | 5/1999 | Gifford, III et al. | |
| 5,910,149 A | 6/1999 | Kuzmak | |
| 5,928,195 A | 7/1999 | Malamud et al. | |
| 5,938,669 A | 8/1999 | Klaiber et al. | |
| 5,944,696 A | 8/1999 | Bayless et al. | |
| 5,944,751 A | 8/1999 | Laub | |
| 5,993,473 A | 11/1999 | Chan et al. | |
| 5,997,502 A | 12/1999 | Reilly et al. | |
| 6,010,511 A | 1/2000 | Murphy | |
| 6,013,679 A | 1/2000 | Kuo et al. | |
| 6,024,340 A | 2/2000 | Lazarus et al. | |
| 6,024,704 A | 2/2000 | Meador et al. | |
| 6,042,345 A | 3/2000 | Bishop et al. | |
| 6,048,309 A | 4/2000 | Flom et al. | |
| 6,067,991 A | 5/2000 | Forsell | |
| 6,074,341 A | 6/2000 | Anderson et al. | |
| 6,074,378 A | 6/2000 | Mouri et al. | |
| 6,083,249 A | 7/2000 | Familoni | |
| 6,090,064 A | 7/2000 | Reilly et al. | |
| 6,090,131 A | 7/2000 | Daley | |
| 6,102,678 A | 8/2000 | Peclat | |
| 6,102,922 A | 8/2000 | Jakobsson et al. | |
| 6,117,086 A | 9/2000 | Shulze | |
| 6,129,668 A | 10/2000 | Haynor et al. | |
| 6,164,933 A | 12/2000 | Tani et al. | |
| 6,171,321 B1 | 1/2001 | Gifford, III et al. | |
| 6,179,569 B1 | 1/2001 | Kojima et al. | |
| 6,193,734 B1 | 2/2001 | Bolduc et al. | |
| 6,203,523 B1 | 3/2001 | Haller et al. | |
| 6,210,345 B1 | 4/2001 | Van Brunt | |
| 6,210,347 B1 | 4/2001 | Forsell | |
| 6,221,024 B1 | 4/2001 | Miesel | |
| 6,224,857 B1 | 5/2001 | Romeo et al. | |
| 6,306,088 B1 | 10/2001 | Krausman et al. | |
| 6,306,116 B1 | 10/2001 | Hancock | |
| 6,327,503 B1 | 12/2001 | Familoni | |

| | | |
|---|---|---|
| 6,371,942 B1 | 4/2002 | Schwartz et al. |
| 6,371,965 B2 | 4/2002 | Gifford, III et al. |
| 6,387,105 B1 | 5/2002 | Gifford, III et al. |
| 6,402,717 B1 | 6/2002 | Reilly et al. |
| 6,402,718 B1 | 6/2002 | Reilly et al. |
| 6,417,750 B1 | 7/2002 | Sohn |
| 6,419,696 B1 | 7/2002 | Ortiz et al. |
| 6,432,040 B1 | 8/2002 | Meah |
| 6,439,539 B1 | 8/2002 | Powell |
| 6,443,957 B1 | 9/2002 | Addis |
| 6,443,965 B1 | 9/2002 | Gifford, III et al. |
| 6,450,173 B1 | 9/2002 | Forsell |
| 6,450,946 B1 | 9/2002 | Forsell |
| 6,450,987 B1 * | 9/2002 | Kramer .................. 604/43 |
| 6,451,034 B1 | 9/2002 | Gifford, III et al. |
| 6,453,907 B1 | 9/2002 | Forsell |
| 6,454,699 B1 | 9/2002 | Forsell |
| 6,454,700 B1 | 9/2002 | Forsell |
| 6,454,701 B1 | 9/2002 | Forsell |
| 6,454,785 B2 | 9/2002 | De Hoyas Garza |
| 6,457,801 B1 | 10/2002 | Fish et al. |
| 6,460,543 B1 | 10/2002 | Forsell |
| 6,461,293 B1 | 10/2002 | Forsell |
| 6,463,935 B1 | 10/2002 | Forsell |
| 6,464,628 B1 | 10/2002 | Forsell |
| 6,470,892 B1 | 10/2002 | Forsell |
| 6,474,584 B2 | 11/2002 | Ekich |
| 6,475,136 B1 | 11/2002 | Forsell |
| 6,475,192 B1 | 11/2002 | Reilly et al. |
| 6,485,496 B1 | 11/2002 | Suyker et al. |
| 6,491,704 B2 | 12/2002 | Gifford, III et al. |
| 6,491,705 B2 | 12/2002 | Gifford, III et al. |
| 6,511,490 B2 | 1/2003 | Robert |
| 6,517,556 B1 | 2/2003 | Monassevitch |
| 6,527,701 B1 | 3/2003 | Sayet et al. |
| 6,547,801 B1 | 4/2003 | Dargent et al. |
| 6,562,008 B1 | 5/2003 | Reilly et al. |
| 6,565,582 B2 | 5/2003 | Gifford, III et al. |
| 6,579,301 B1 | 6/2003 | Bales et al. |
| 6,601,604 B1 | 8/2003 | Cooper |
| 6,615,084 B1 | 9/2003 | Cigaina |
| 6,632,239 B2 | 10/2003 | Snyder et al. |
| 6,635,020 B2 | 10/2003 | Tripp, Jr. et al. |
| 6,638,258 B2 | 10/2003 | Schwartz et al. |
| 6,646,628 B2 | 11/2003 | Shirochi et al. |
| 6,676,674 B1 | 1/2004 | Dudai |
| 6,681,135 B1 | 1/2004 | Davis et al. |
| 6,685,668 B1 | 2/2004 | Cho et al. |
| 6,691,047 B1 | 2/2004 | Fredricks |
| 6,715,731 B1 | 4/2004 | Post et al. |
| 6,725,726 B1 | 4/2004 | Adolfs et al. |
| 6,729,600 B2 | 5/2004 | Mattes et al. |
| 6,733,478 B2 | 5/2004 | Reilly et al. |
| 6,754,527 B2 | 6/2004 | Stroebel et al. |
| 6,778,927 B2 | 8/2004 | Cha et al. |
| 6,799,698 B2 | 10/2004 | Ono et al. |
| 6,808,513 B2 | 10/2004 | Reilly et al. |
| 6,811,136 B2 | 11/2004 | Eberhardt et al. |
| 6,820,651 B2 | 11/2004 | Seuret et al. |
| 6,834,201 B2 | 12/2004 | Gillies et al. |
| 6,871,090 B1 | 3/2005 | He et al. |
| 6,889,086 B2 | 5/2005 | Mass et al. |
| 6,916,326 B2 | 7/2005 | Benchetrit |
| 6,940,467 B2 | 9/2005 | Fisher et al. |
| 6,966,875 B1 | 11/2005 | Longobardi |
| 7,017,583 B2 | 3/2006 | Forsell |
| 7,017,883 B2 | 3/2006 | Bayer et al. |
| 7,021,147 B1 | 4/2006 | Subramanian et al. |
| 7,027,935 B2 | 4/2006 | Shimase et al. |
| 7,037,344 B2 | 5/2006 | Kagan et al. |
| 7,040,349 B2 | 5/2006 | Moler et al. |
| 7,044,933 B2 | 5/2006 | VanDiver et al. |
| 7,048,519 B2 | 5/2006 | Fong et al. |
| 7,054,690 B2 | 5/2006 | Imran |
| 7,058,434 B2 | 6/2006 | Wang et al. |
| 7,060,080 B2 | 6/2006 | Bachmann |
| 7,066,486 B2 | 6/2006 | Lee |
| 7,118,526 B2 | 10/2006 | Egle |
| 7,119,062 B1 | 10/2006 | Alvis et al. |
| 7,128,750 B1 | 10/2006 | Stergiopulos |
| 7,144,400 B2 | 12/2006 | Byrum et al. |
| 7,172,607 B2 | 2/2007 | Hofle et al. |
| 7,177,693 B2 | 2/2007 | Starkebsum |
| 7,191,007 B2 | 3/2007 | Desai et al. |
| 7,195,610 B1 | 3/2007 | Flachbart |
| 7,198,250 B2 | 4/2007 | East |
| 7,204,821 B1 | 4/2007 | Clare et al. |
| 7,206,637 B2 | 4/2007 | Salo |
| 7,223,239 B2 | 5/2007 | Schulze et al. |
| 7,238,191 B2 | 7/2007 | Bachmann |
| 7,240,607 B2 | 7/2007 | Fish |
| 7,255,675 B2 | 8/2007 | Gertner et al. |
| 7,263,405 B2 | 8/2007 | Boveja et al. |
| 7,282,023 B2 | 10/2007 | Frering |
| 7,284,966 B2 | 10/2007 | Xu et al. |
| 7,288,064 B2 | 10/2007 | Boustani et al. |
| 7,297,103 B2 | 11/2007 | Jarsaillon et al. |
| 7,299,082 B2 | 11/2007 | Feldman et al. |
| 7,310,557 B2 | 12/2007 | Maschino et al. |
| 7,311,503 B2 | 12/2007 | Van Lintel et al. |
| 7,311,716 B2 | 12/2007 | Byrum |
| 7,311,717 B2 | 12/2007 | Egle |
| 7,314,443 B2 | 1/2008 | Jordan et al. |
| 7,314,598 B2 | 1/2008 | Nishino |
| 7,314,636 B2 | 1/2008 | Caseres et al. |
| 7,338,433 B2 | 3/2008 | Coe |
| 7,340,306 B2 | 3/2008 | Barrett et al. |
| 7,351,198 B2 | 4/2008 | Byrum et al. |
| 7,351,240 B2 | 4/2008 | Hassler, Jr. et al. |
| 7,353,747 B2 | 4/2008 | Swayze et al. |
| 7,364,542 B2 | 4/2008 | Jambor et al. |
| 7,366,571 B2 | 4/2008 | Armstrong |
| 7,367,340 B2 | 5/2008 | Nelson et al. |
| 7,367,937 B2 | 5/2008 | Jambor et al. |
| 7,374,565 B2 | 5/2008 | Hassler, Jr. et al. |
| 7,390,294 B2 | 6/2008 | Hassler, Jr. |
| 7,396,353 B2 | 7/2008 | Lorenzen et al. |
| 7,416,528 B2 | 8/2008 | Crawford et al. |
| 7,457,668 B2 | 11/2008 | Cancel et al. |
| 7,481,763 B2 | 1/2009 | Hassler, Jr. et al. |
| 7,500,944 B2 | 3/2009 | Byrum et al. |
| 7,502,649 B2 | 3/2009 | Ben-Haim et al. |
| 7,507,221 B2 | 3/2009 | Neer |
| 7,530,943 B2 | 5/2009 | Lechner |
| 7,585,280 B2 | 9/2009 | Wilson et al. |
| 7,594,885 B2 | 9/2009 | Byrum |
| 7,599,743 B2 | 10/2009 | Hassler, Jr. et al. |
| 7,599,744 B2 | 10/2009 | Giordano et al. |
| 7,601,162 B2 | 10/2009 | Hassler, Jr. et al. |
| 7,615,001 B2 | 11/2009 | Jambor et al. |
| 7,618,365 B2 | 11/2009 | Jambor et al. |
| 7,658,196 B2 | 2/2010 | Ferreri et al. |
| 7,670,279 B2 | 3/2010 | Gertner |
| 7,699,770 B2 | 4/2010 | Hassler, Jr. et al. |
| 7,712,470 B2 | 5/2010 | Gertner |
| 7,727,141 B2 | 6/2010 | Hassler, Jr. et al. |
| 7,741,476 B2 | 6/2010 | Lebreton |
| 7,758,493 B2 | 7/2010 | Gingras |
| 7,763,039 B2 | 7/2010 | Ortiz et al. |
| 7,766,815 B2 | 8/2010 | Ortiz |
| 7,771,439 B2 | 8/2010 | Griffiths |
| 7,775,215 B2 | 8/2010 | Hassler, Jr. et al. |
| 7,775,966 B2 | 8/2010 | Dlugos et al. |
| 7,775,967 B2 | 8/2010 | Gertner |
| 7,794,386 B2 | 9/2010 | Brooks |
| 7,811,298 B2 | 10/2010 | Birk |
| 7,828,813 B2 | 11/2010 | Mouton |
| 7,832,407 B2 | 11/2010 | Gertner |
| 7,841,978 B2 | 11/2010 | Gertner |
| 7,844,342 B2 | 11/2010 | Dlugos et al. |
| 7,862,502 B2 | 1/2011 | Pool et al. |
| 7,879,068 B2 | 2/2011 | Dlugos et al. |
| 7,927,270 B2 | 4/2011 | Dlugos et al. |
| 7,951,067 B2 | 5/2011 | Byrum et al. |
| 2001/0011543 A1 | 8/2001 | Forsell |
| 2002/0038105 A1 | 3/2002 | Schwartz et al. |
| 2002/0072780 A1 | 6/2002 | Foley |
| 2002/0091395 A1 | 7/2002 | Gabbay |

| | | |
|---|---|---|
| 2002/0095181 A1 | 7/2002 | Beyar |
| 2002/0098097 A1 | 7/2002 | Singh |
| 2002/0123716 A1 | 9/2002 | VanDiver et al. |
| 2002/0133081 A1 | 9/2002 | Ackerman et al. |
| 2002/0139208 A1 | 10/2002 | Yatskov |
| 2002/0152816 A1 | 10/2002 | Kim |
| 2002/0177811 A1 | 11/2002 | Reilly et al. |
| 2002/0183765 A1 | 12/2002 | Adams |
| 2002/0198548 A1 | 12/2002 | Robert |
| 2003/0009123 A1 | 1/2003 | Brugger |
| 2003/0014003 A1 | 1/2003 | Gertner |
| 2003/0019498 A1 | 1/2003 | Forsell |
| 2003/0045775 A1 | 3/2003 | Forsell |
| 2003/0045902 A1 | 3/2003 | Weadock |
| 2003/0055311 A1 | 3/2003 | Neukermans et al. |
| 2003/0060754 A1 | 3/2003 | Reilly et al. |
| 2003/0060873 A1 | 3/2003 | Gertner et al. |
| 2003/0066536 A1 | 4/2003 | Forsell |
| 2003/0073880 A1 | 4/2003 | Polsky et al. |
| 2003/0093157 A1 | 5/2003 | Caseres et al. |
| 2003/0100910 A1 | 5/2003 | Gifford, III et al. |
| 2003/0120288 A1 | 6/2003 | Benchetrit |
| 2003/0148995 A1 | 8/2003 | Piron et al. |
| 2003/0158564 A1 | 8/2003 | Benchetrit |
| 2003/0158569 A1 | 8/2003 | Wazne |
| 2003/0167022 A1 | 9/2003 | Dijkman |
| 2003/0171887 A1 | 9/2003 | Cha et al. |
| 2003/0181890 A1 | 9/2003 | Schulze et al. |
| 2003/0181917 A1 | 9/2003 | Gertner |
| 2003/0191433 A1 | 10/2003 | Prentiss |
| 2003/0208212 A1 | 11/2003 | Cigaina |
| 2003/0213285 A1 | 11/2003 | Wheeler et al. |
| 2004/0000843 A1 | 1/2004 | East |
| 2004/0034479 A1 | 2/2004 | Shimase et al. |
| 2004/0044332 A1 | 3/2004 | Stergiopulos |
| 2004/0049209 A1 | 3/2004 | Benchetrit |
| 2004/0059393 A1 | 3/2004 | Policker et al. |
| 2004/0068847 A1 | 4/2004 | Belisle et al. |
| 2004/0069714 A1 | 4/2004 | Ferguson |
| 2004/0133219 A1 | 7/2004 | Forsell |
| 2004/0147816 A1 | 7/2004 | Policker et al. |
| 2004/0148034 A1 | 7/2004 | Kagan et al. |
| 2004/0153106 A1 | 8/2004 | Dudai |
| 2004/0162595 A1 | 8/2004 | Foley |
| 2004/0171942 A1 | 9/2004 | Ackerman et al. |
| 2004/0215159 A1 | 10/2004 | Forsell |
| 2004/0230137 A1 | 11/2004 | Mouton |
| 2004/0235025 A1 | 11/2004 | Mori et al. |
| 2004/0243057 A1 | 12/2004 | Vinten-Johansen |
| 2004/0254533 A1 | 12/2004 | Schriver et al. |
| 2004/0254536 A1 | 12/2004 | Conlon et al. |
| 2004/0254537 A1 | 12/2004 | Conlon et al. |
| 2004/0260319 A1 | 12/2004 | Egle |
| 2004/0267288 A1 | 12/2004 | Byrum et al. |
| 2004/0267291 A1 | 12/2004 | Byrum et al. |
| 2004/0267292 A1 | 12/2004 | Byrum et al. |
| 2004/0267293 A1 | 12/2004 | Byrum et al. |
| 2004/0267377 A1 | 12/2004 | Egle |
| 2005/0002984 A1 | 1/2005 | Byrum et al. |
| 2005/0038484 A1 | 2/2005 | Knudson et al. |
| 2005/0038498 A1 | 2/2005 | Dubrow et al. |
| 2005/0055039 A1 | 3/2005 | Burnett et al. |
| 2005/0070934 A1 | 3/2005 | Tanaka et al. |
| 2005/0070937 A1 | 3/2005 | Jambor et al. |
| 2005/0100779 A1 | 5/2005 | Gertner |
| 2005/0104457 A1 | 5/2005 | Jordan et al. |
| 2005/0119672 A1 | 6/2005 | Benchetrit |
| 2005/0119674 A1 | 6/2005 | Gingras |
| 2005/0131383 A1 | 6/2005 | Chen et al. |
| 2005/0131485 A1 | 6/2005 | Knudson et al. |
| 2005/0136122 A1 | 6/2005 | Sadozai et al. |
| 2005/0142152 A1 | 6/2005 | Leshchiner et al. |
| 2005/0143765 A1 | 6/2005 | Bachmann et al. |
| 2005/0143766 A1 | 6/2005 | Bachmann et al. |
| 2005/0154274 A1 | 7/2005 | Jarsaillon et al. |
| 2005/0171568 A1 | 8/2005 | Duffy |
| 2005/0177111 A1 | 8/2005 | Ozeri et al. |
| 2005/0183730 A1 | 8/2005 | Byrum |
| 2005/0192531 A1 | 9/2005 | Birk |
| 2005/0192601 A1 | 9/2005 | Demarais |
| 2005/0192614 A1* | 9/2005 | Binmoeller .................. 606/191 |
| 2005/0192629 A1 | 9/2005 | Saadat et al. |
| 2005/0216042 A1 | 9/2005 | Gertner |
| 2005/0226936 A1 | 10/2005 | Agerup |
| 2005/0228415 A1 | 10/2005 | Gertner |
| 2005/0228504 A1 | 10/2005 | Demarais |
| 2005/0240155 A1 | 10/2005 | Conlon |
| 2005/0240156 A1 | 10/2005 | Conlon |
| 2005/0240279 A1 | 10/2005 | Kagan et al. |
| 2005/0244288 A1 | 11/2005 | O'Neill |
| 2005/0250979 A1 | 11/2005 | Coe |
| 2005/0251181 A1 | 11/2005 | Bachmann |
| 2005/0251182 A1 | 11/2005 | Bachmann |
| 2005/0267406 A1 | 12/2005 | Hassler, Jr. |
| 2005/0267500 A1 | 12/2005 | Hassler, Jr. |
| 2005/0267533 A1 | 12/2005 | Gertner |
| 2005/0271729 A1 | 12/2005 | Wang |
| 2005/0277899 A1 | 12/2005 | Conlon et al. |
| 2005/0283041 A1 | 12/2005 | Egle |
| 2005/0288739 A1 | 12/2005 | Hassler, Jr. et al. |
| 2005/0288740 A1 | 12/2005 | Hassler, Jr. et al. |
| 2006/0009697 A1 | 1/2006 | Banet et al. |
| 2006/0015138 A1 | 1/2006 | Gertner |
| 2006/0020298 A1 | 1/2006 | Camilleri et al. |
| 2006/0041183 A1 | 2/2006 | Massen et al. |
| 2006/0074439 A1 | 4/2006 | Garner et al. |
| 2006/0074473 A1 | 4/2006 | Gertner |
| 2006/0079766 A1 | 4/2006 | Neer et al. |
| 2006/0079767 A1 | 4/2006 | Gibb et al. |
| 2006/0089571 A1 | 4/2006 | Gertner |
| 2006/0122147 A1 | 6/2006 | Wohlrab |
| 2006/0142700 A1 | 6/2006 | Sobelman et al. |
| 2006/0142790 A1 | 6/2006 | Gertner |
| 2006/0149161 A1 | 7/2006 | Wilson et al. |
| 2006/0161186 A1 | 7/2006 | Hassler, Jr. et al. |
| 2006/0167531 A1 | 7/2006 | Gertner et al. |
| 2006/0173238 A1 | 8/2006 | Starkebaum |
| 2006/0173424 A1 | 8/2006 | Conlon |
| 2006/0178555 A1 | 8/2006 | Bortolotti |
| 2006/0183967 A1 | 8/2006 | Lechner |
| 2006/0189887 A1 | 8/2006 | Hassler, Jr. et al. |
| 2006/0189888 A1 | 8/2006 | Hassler, Jr. et al. |
| 2006/0189889 A1 | 8/2006 | Gertner |
| 2006/0194758 A1 | 8/2006 | Lebreton |
| 2006/0195139 A1 | 8/2006 | Gertner |
| 2006/0197412 A1 | 9/2006 | Rasmussen |
| 2006/0199997 A1 | 9/2006 | Hassler, Jr. et al. |
| 2006/0211912 A1 | 9/2006 | Dlugos et al. |
| 2006/0211913 A1 | 9/2006 | Dlugos et al. |
| 2006/0211914 A1 | 9/2006 | Hassler, Jr. et al. |
| 2006/0212051 A1 | 9/2006 | Snyder et al. |
| 2006/0212053 A1 | 9/2006 | Gertner |
| 2006/0235448 A1 | 10/2006 | Roslin et al. |
| 2006/0246137 A1 | 11/2006 | Hermitte et al. |
| 2006/0247721 A1 | 11/2006 | Maschino et al. |
| 2006/0247722 A1 | 11/2006 | Maschino et al. |
| 2006/0252982 A1 | 11/2006 | Hassler, Jr. |
| 2006/0252983 A1 | 11/2006 | Lembo et al. |
| 2006/0257488 A1 | 11/2006 | Hubbard |
| 2006/0264699 A1 | 11/2006 | Gertner |
| 2006/0264762 A1 | 11/2006 | Starr |
| 2006/0276812 A1 | 12/2006 | Hill et al. |
| 2006/0293627 A1 | 12/2006 | Byrum et al. |
| 2007/0001447 A1 | 1/2007 | Fennington, Jr. |
| 2007/0015954 A1 | 1/2007 | Dlugos |
| 2007/0015955 A1 | 1/2007 | Tsonton |
| 2007/0015956 A1 | 1/2007 | Crawford et al. |
| 2007/0016231 A1 | 1/2007 | Jambor et al. |
| 2007/0016262 A1 | 1/2007 | Gross et al. |
| 2007/0027356 A1 | 2/2007 | Ortiz |
| 2007/0027358 A1 | 2/2007 | Gertner et al. |
| 2007/0044655 A1 | 3/2007 | Fish |
| 2007/0077292 A1 | 4/2007 | Pinsky |
| 2007/0078476 A1 | 4/2007 | Hull, Sr. et al. |
| 2007/0106153 A1 | 5/2007 | Neer et al. |
| 2007/0125826 A1 | 6/2007 | Shelton |
| 2007/0156013 A1 | 7/2007 | Birk |
| 2007/0167672 A1 | 7/2007 | Dlugos et al. |

| | | |
|---|---|---|
| 2007/0167982 A1 | 7/2007 | Gertner et al. |
| 2007/0173685 A1 | 7/2007 | Jambor et al. |
| 2007/0173888 A1 | 7/2007 | Gertner et al. |
| 2007/0179335 A1 | 8/2007 | Gertner et al. |
| 2007/0185373 A1 | 8/2007 | Tsonton |
| 2007/0185462 A1 | 8/2007 | Byrum |
| 2007/0191717 A1 | 8/2007 | Rosen et al. |
| 2007/0213836 A1 | 9/2007 | Paganon |
| 2007/0218083 A1 | 9/2007 | Brooks |
| 2007/0232848 A1 | 10/2007 | Forsell |
| 2007/0232849 A1 | 10/2007 | Gertner |
| 2007/0233170 A1 | 10/2007 | Gertner |
| 2007/0235083 A1 | 10/2007 | Dlugos et al. |
| 2007/0243227 A1 | 10/2007 | Gertner |
| 2007/0250085 A1 | 10/2007 | Bachmann et al. |
| 2007/0250086 A1 | 10/2007 | Wiley et al. |
| 2007/0255335 A1 | 11/2007 | Herbert et al. |
| 2007/0255336 A1 | 11/2007 | Herbert et al. |
| 2007/0265598 A1 | 11/2007 | Karasik |
| 2007/0265645 A1 | 11/2007 | Birk et al. |
| 2007/0265646 A1 | 11/2007 | McCoy et al. |
| 2007/0298005 A1 | 12/2007 | Thibault |
| 2008/0009680 A1 | 1/2008 | Hassler, Jr. |
| 2008/0015406 A1 | 1/2008 | Dlugos et al. |
| 2008/0015501 A1 | 1/2008 | Gertner |
| 2008/0027269 A1 | 1/2008 | Gartner |
| 2008/0027469 A1 | 1/2008 | Bachmann |
| 2008/0071306 A1 | 3/2008 | Gertner |
| 2008/0097496 A1 | 4/2008 | Chang et al. |
| 2008/0108862 A1 | 5/2008 | Jordan et al. |
| 2008/0108896 A1 | 5/2008 | Gibb et al. |
| 2008/0108941 A1 | 5/2008 | Neer |
| 2008/0108943 A1 | 5/2008 | Wagner |
| 2008/0114302 A1 | 5/2008 | Neer |
| 2008/0147002 A1 | 6/2008 | Gertner |
| 2008/0161717 A1 | 7/2008 | Gertner |
| 2008/0161875 A1 | 7/2008 | Stone |
| 2008/0166028 A1 | 7/2008 | Turek et al. |
| 2008/0167647 A1 | 7/2008 | Gertner |
| 2008/0167648 A1 | 7/2008 | Gertner |
| 2008/0172072 A1 | 7/2008 | Pool et al. |
| 2008/0188766 A1 | 8/2008 | Gertner |
| 2008/0195092 A1 | 8/2008 | Kim et al. |
| 2008/0208240 A1 | 8/2008 | Paz |
| 2008/0221598 A1 | 9/2008 | Dlugos et al. |
| 2008/0243071 A1 | 10/2008 | Quijano et al. |
| 2008/0249806 A1 | 10/2008 | Dlugos et al. |
| 2008/0250340 A1 | 10/2008 | Dlugos et al. |
| 2008/0250341 A1 | 10/2008 | Dlugos et al. |
| 2008/0255403 A1 | 10/2008 | Voegele et al. |
| 2008/0255414 A1 | 10/2008 | Voegele et al. |
| 2008/0255425 A1 | 10/2008 | Voegele et al. |
| 2008/0255459 A1 | 10/2008 | Voegele et al. |
| 2008/0255537 A1 | 10/2008 | Voegele et al. |
| 2008/0275294 A1 | 11/2008 | Gertner |
| 2008/0275295 A1 | 11/2008 | Gertner |
| 2008/0275484 A1 | 11/2008 | Gertner |
| 2008/0281347 A1 | 11/2008 | Gertner |
| 2008/0287969 A1 | 11/2008 | Tsonton et al. |
| 2008/0287974 A1 | 11/2008 | Widenhouse et al. |
| 2008/0287976 A1 | 11/2008 | Weaner et al. |
| 2008/0294097 A1 | 11/2008 | Kim et al. |
| 2008/0300618 A1 | 12/2008 | Gertner |
| 2008/0306443 A1 | 12/2008 | Neer et al. |
| 2008/0319435 A1 | 12/2008 | Rioux et al. |
| 2009/0054914 A1 | 2/2009 | Lechner |
| 2009/0062825 A1 | 3/2009 | Pool et al. |
| 2009/0062826 A1 | 3/2009 | Steffen |
| 2009/0082793 A1 | 3/2009 | Birk |
| 2009/0118572 A1 | 5/2009 | Lechner |
| 2009/0149874 A1 | 6/2009 | Ortiz et al. |
| 2009/0157106 A1 | 6/2009 | Marcotte et al. |
| 2009/0157107 A1 | 6/2009 | Kierath et al. |
| 2009/0157113 A1 | 6/2009 | Marcotte et al. |
| 2009/0163803 A1 | 6/2009 | Neer et al. |
| 2009/0171375 A1 | 7/2009 | Coe et al. |
| 2009/0171378 A1 | 7/2009 | Coe et al. |
| 2009/0171379 A1 | 7/2009 | Coe et al. |
| 2009/0187202 A1 | 7/2009 | Ortiz et al. |
| 2009/0188494 A1 | 7/2009 | Imai et al. |
| 2009/0192404 A1 | 7/2009 | Ortiz et al. |
| 2009/0192415 A1 | 7/2009 | Ortiz et al. |
| 2009/0192533 A1 | 7/2009 | Dlugos, Jr. et al. |
| 2009/0192534 A1 | 7/2009 | Ortiz et al. |
| 2009/0192541 A1 | 7/2009 | Ortiz et al. |
| 2009/0198261 A1 | 8/2009 | Schweikert |
| 2009/0202387 A1 | 8/2009 | Dlugos, Jr. et al. |
| 2009/0204131 A1 | 8/2009 | Ortiz et al. |
| 2009/0204132 A1 | 8/2009 | Ortiz et al. |
| 2009/0204141 A1 | 8/2009 | Dlugos, Jr. et al. |
| 2009/0204179 A1 | 8/2009 | Dlugos, Jr. et al. |
| 2009/0209995 A1 | 8/2009 | Byrum et al. |
| 2009/0216193 A1 | 8/2009 | Schriver et al. |
| 2009/0216255 A1 | 8/2009 | Coe et al. |
| 2009/0220176 A1 | 9/2009 | Fusco |
| 2009/0222031 A1 | 9/2009 | Axelsson |
| 2009/0222065 A1 | 9/2009 | Dlugos, Jr. et al. |
| 2009/0228063 A1 | 9/2009 | Dlugos, Jr. et al. |
| 2009/0228072 A1 | 9/2009 | Coe et al. |
| 2009/0241677 A1 | 10/2009 | Klees et al. |
| 2009/0270759 A1 | 10/2009 | Wilson et al. |
| 2009/0270904 A1 | 10/2009 | Birk et al. |
| 2009/0306462 A1 | 12/2009 | Lechner |
| 2009/0312635 A1 | 12/2009 | Shimchuk et al. |
| 2009/0312785 A1 | 12/2009 | Stone et al. |
| 2010/0010291 A1 | 1/2010 | Birk et al. |
| 2010/0087843 A1 | 4/2010 | Bertolote et al. |
| 2010/0099945 A1 | 4/2010 | Birk et al. |
| 2010/0100079 A1 | 4/2010 | Berkcan |
| 2010/0145378 A1 | 6/2010 | Gertner |
| 2010/0152532 A1 | 6/2010 | Marcotte |
| 2010/0168508 A1 | 7/2010 | Gertner |
| 2010/0185049 A1 | 7/2010 | Birk et al. |
| 2010/0191265 A1 | 7/2010 | Lau et al. |
| 2010/0191271 A1 | 7/2010 | Lau et al. |
| 2010/0204647 A1 | 8/2010 | Gertner |
| 2010/0204723 A1 | 8/2010 | Gertner |
| 2010/0226988 A1 | 9/2010 | Lebreton |
| 2010/0228080 A1 | 9/2010 | Tavori et al. |
| 2010/0234682 A1 | 9/2010 | Gertner |
| 2010/0249803 A1 | 9/2010 | Griffiths |
| 2010/0280310 A1 | 11/2010 | Raven |
| 2010/0305397 A1 | 12/2010 | Birk et al. |
| 2010/0312147 A1 | 12/2010 | Gertner |
| 2010/0324358 A1 | 12/2010 | Birk et al. |
| 2010/0324359 A1 | 12/2010 | Birk |
| 2011/0130626 A1 | 6/2011 | Hassler, Jr. et al. |
| 2011/0201874 A1 | 8/2011 | Birk et al. |

FOREIGN PATENT DOCUMENTS

| | | |
|---|---|---|
| CN | 1250382 | 4/2000 |
| CN | 1367670 | 9/2002 |
| DE | 4225524 | 2/1994 |
| DE | 19802615 | 8/1999 |
| DE | 10020688 | 12/2000 |
| EP | 0119596 | 9/1984 |
| EP | 0230747 | 8/1987 |
| EP | 0416250 | 3/1991 |
| EP | 0611561 | 8/1994 |
| EP | 0695558 | 2/1996 |
| EP | 0876808 | 11/1998 |
| EP | 1036545 | 9/2000 |
| EP | 1072282 | 1/2001 |
| EP | 1105073 | 6/2001 |
| EP | 1396242 | 3/2004 |
| EP | 1396243 | 3/2004 |
| EP | 1491167 | 12/2004 |
| EP | 1491168 | 12/2004 |
| EP | 1529502 | 5/2005 |
| EP | 1547549 | 6/2005 |
| EP | 1574189 | 9/2005 |
| EP | 1600183 | 11/2005 |
| EP | 1602346 | 12/2005 |
| EP | 1704833 | 9/2006 |
| EP | 1719480 | 11/2006 |
| EP | 1754890 | 11/2006 |
| EP | 1736123 | 12/2006 |
| EP | 1736195 | 12/2006 |

| | | |
|---|---|---|
| EP | 1736202 | 12/2006 |
| EP | 1743605 | 1/2007 |
| EP | 1829504 | 9/2007 |
| EP | 1829505 | 9/2007 |
| EP | 1829506 | 9/2007 |
| EP | 1949875 | 7/2008 |
| EP | 1967168 | 9/2008 |
| EP | 1922316 | 11/2008 |
| EP | 1992315 | 11/2008 |
| EP | 1992316 | 11/2008 |
| EP | 2074970 | 7/2009 |
| EP | 2074971 | 7/2009 |
| EP | 2087862 | 8/2009 |
| EP | 2095796 | 9/2009 |
| EP | 2095797 | 9/2009 |
| EP | 2095798 | 9/2009 |
| FR | 1566202 | 5/1969 |
| FR | 2688693 | 9/1993 |
| FR | 2769491 | 4/1999 |
| FR | 2783153 | 3/2000 |
| FR | 2797181 | 2/2001 |
| FR | 2799118 | 4/2001 |
| FR | 2823663 | 10/2002 |
| FR | 2855744 | 12/2004 |
| FR | 2921822 | 4/2009 |
| GB | 1174814 | 12/1969 |
| GB | 2090747 | 7/1982 |
| JP | 57-171676 | 10/1982 |
| JP | 1-67309 | 4/1989 |
| JP | 2-019147 | 1/1990 |
| JP | 2-132104 | 11/1990 |
| JP | 3-105702 | 11/1991 |
| JP | 11-244395 | 9/1999 |
| JP | 2003-526410 | 9/2003 |
| JP | 2005-131380 | 5/2005 |
| JP | 2005-334658 | 12/2005 |
| SE | 8503144 | 12/1986 |
| WO | WO 86/00079 | 1/1986 |
| WO | WO 86/00912 | 2/1986 |
| WO | WO 89/11701 | 11/1989 |
| WO | WO 90/00369 | 1/1990 |
| WO | WO 92/20349 | 11/1992 |
| WO | WO 94/02517 | 2/1994 |
| WO | WO 96/33751 | 1/1996 |
| WO | WO 98/35639 | 8/1998 |
| WO | WO 98/35640 | 8/1998 |
| WO | WO 00/00108 | 1/2000 |
| WO | WO 00/01428 | 1/2000 |
| WO | WO 00/09047 | 2/2000 |
| WO | WO 00/09048 | 2/2000 |
| WO | WO 00/15158 | 3/2000 |
| WO | WO 00/66196 | 11/2000 |
| WO | WO 01/10359 | 2/2001 |
| WO | WO 01/12078 | 2/2001 |
| WO | WO 01/41671 | 6/2001 |
| WO | WO 01/47435 | 7/2001 |
| WO | WO 01/47575 | 7/2001 |
| WO | WO 01/49245 | 7/2001 |
| WO | WO 01/52777 | 7/2001 |
| WO | WO 01/68007 | 9/2001 |
| WO | WO 01/70131 | 9/2001 |
| WO | WO 01/85071 | 11/2001 |
| WO | WO 02/05753 | 1/2002 |
| WO | WO 02/09792 | 2/2002 |
| WO | WO 02/19953 | 3/2002 |
| WO | WO 02/26317 | 4/2002 |
| WO | WO 02/053093 | 7/2002 |
| WO | WO 02/065948 | 8/2002 |
| WO | WO 02/096326 | 12/2002 |
| WO | WO 03/007782 | 1/2003 |
| WO | WO 03/055420 | 7/2003 |
| WO | WO 03/057092 | 7/2003 |
| WO | WO 03/059215 | 7/2003 |
| WO | WO 03/077191 | 9/2003 |
| WO | WO 03/101352 | 12/2003 |
| WO | WO 03/105732 | 12/2003 |
| WO | WO 2004/014245 | 2/2004 |
| WO | WO 2004/019671 | 3/2004 |
| WO | WO 2004/108025 | 12/2004 |
| WO | WO 2004/112563 | 12/2004 |
| WO | WO 2005/007232 | 1/2005 |
| WO | WO 2005/009305 | 2/2005 |
| WO | WO 2005/067994 | 5/2005 |
| WO | WO 2005/072195 | 8/2005 |
| WO | WO 2005/087147 | 9/2005 |
| WO | WO 2005/094447 | 10/2005 |
| WO | WO 2005/112888 | 12/2005 |
| WO | WO 2006/049725 | 5/2006 |
| WO | WO 2006/083885 | 8/2006 |
| WO | WO 2006/108203 | 10/2006 |
| WO | WO 2007/067206 | 6/2007 |
| WO | WO 2007/081304 | 7/2007 |
| WO | WO 2007/106727 | 9/2007 |
| WO | WO 2007/114905 | 10/2007 |
| WO | WO 2007/145638 | 12/2007 |
| WO | WO 2008/063673 | 5/2008 |
| WO | WO 2008/109300 | 9/2008 |
| WO | WO 2008/134755 | 11/2008 |
| WO | WO 2009/023247 | 2/2009 |
| WO | WO 2009/050709 | 4/2009 |
| WO | WO 2009/132127 | 10/2009 |
| WO | WO 2009/136126 | 11/2009 |
| WO | WO 2010/042493 | 4/2010 |

OTHER PUBLICATIONS

Brown et al; "Symmetrical Pouch Dilation After Laparoscopic Adjustable Gastric Banding: Incidence and Management"; Obesity Surgery; V. 18, pp. 1104-1108; 2008.

Ceelen et al.; "Surgical Treatment of Severe Obesity With a Low-Pressure Adjustable Gastric Band: Experimental Data and Clinical Results in 625 Patients"; Annals of Surgery; V. 237, No. 1; pp. 10-16; 2003.

Dixon et al.; "Pregnancy After Lap-Band Surgery: Management of the Band to Achieve Healthy Weight Outcomes"; Obesity Surgery; V. 11, pp. 59-65; 2001.

Neary et al.; "Peptide YY(3-36) and Glucagon-Like Peptide-1$_{(7-36)}$ Inhibit Food Intake Additively"; Endocrinology; V.146; pp. 5120-5127; 2005.

Padidela et al.; "Elevated basal and post-feed glucagon-like petide 1 (GLP-1) concentrations in the neonatel period"; European Journal of Endocrinology; v. 160; pp. 53-58; 2009.

Shi et al.; "Sexually Dimorphic Responses to Fat Loss After Caloric Restriction or Surgical Lipectomy"; Am. J. Physiol. Endocrinol. Metab.; V. 293; E316-E326; 2007.

Xanthakos et al.; "Bariatric Surgery for Extreme Adolescent Obesity: Indications, Outcomes, and Physiologic Effects on the Gut-Brain Axis"; Pathophysiology; V. 15; pp. 135-146; 2008.

"Innovative medical devices and implants"; LGSP medical futures, p. 5.

Acuna-Goycolea et al.; "Mechanism of Neuropeptide Y, Peptide YY, and Pancreatic Polypeptide Inhibition of Identified Green Fluorescent Protein-Expressing GABA Neurons in the Hypothalamic Neuroendocrine Acruate Nucleus"; The Journal of Neuroscience; V. 25(32); pp. 7406-7419; Aug. 10, 2005.

Adrian et al.; "Mechanism of Pancreatic Polypeptide Release in Man." The Lancet; pp. 161-163; Jan. 22, 1977.

Anson; "Shape Memory Alloys—Medical Applications," Source: Materials World, vol. 7, No. 12, pp. 745-747, Dec. 1999.

Asakawa et al; "Antagonism of Ghrelin Receptor Reduces Food Intake and Body Weight Gain in Mice"; Gut.; V.52; pp. 947-952; 2003.

Baggio et al. "Biology of Incretins: GLP-1 and GIP"; Gastroenrology; V. 132; pp. 2131-2157; 2007.

Ballantyne; "Peptide YY(1-36) and Peptide YY(3-36): Part I. Distribution, Release, and Actions"; Obesity Surgery; V.16; pp. 651-658; 2006.

Ballantyne; "Peptide YY(1-36) and Peptide YY(3-36): Part II. Changes after Gastrointestinal Surgery and Bariatric Surgery"; Obesity Surgery; V.16; pp. 795-803; 2006.

Berne et al; "Physiology"; V. 5; pp. 55-57, 210, 428, 540, 554, 579, 584, 591; 2004.

BioEnterics Lap-Band Adjustable Gastric Banding System, Inamed Health, pub., pp. 1-115; Aug. 28, 2003.

Boulant et al.; "Cholecystokinin in Transient Lower Oesophageal Sphincter Relaxation Due to Gastric Distension in Humans"; Gut.; V. 40; pp. 575-581; 1997.

Bradjewin et al.; "Dose Ranging Study of the Effects of Cholecystokinin in Healthy Volunteers"; J. Psychiatr. Neurosci.; V. 16 (2); pp. 91-95; 1991.

Burdyga et al.; "Cholecystokinin Regulates Expression of Y2 Receptors in Vagal Afferent Neurons Serving the Stomach"; The Journal of Neuroscience; V. 28; No. 45; pp. 11583-11592; Nov. 5, 2008.

Chaptini et al.; "Neuroendocrine Regulation of Food Intake"; Current Opinion in Gastroenterology; V. 24; pp. 223-229; 2008.

Chaudhri; "Can Gut Hormones Control Appetite and Prevent Obesity?" Diabetes Care; V. 31; Supp 2; pp. S284-S289; Feb. 2008.

Cohen et al.; "Oxyntomodulin Suppresses Appetite and Reduces Food Intake in Humans"; J. Clin. Endocrinol. Metab.; V. 88; No. 10; pp. 4696-4701; 2003.

Corno et al.; "A new implantable device for telemetric control of pulmonary blood flow"; New ideas; received in revised form Jul. 12, 2002; 10 pages.

Corno et al.; "FlowWatchTM in clipped and in clipped position"; Interact Cardio Vase Thorac Surg 2002; 1:46-49; Copyright @ 2002 The European Association for Cardio-thoracic Surgery; 1 page.

Cummings et al.; "Plasma Ghrelin Levels After Diet-Induced Weight Loss or Gastric Bypass Surgery"; N. Engl J. Med; V. 346, No. 21; pp. 1623-1630; May 23, 2002.

Cummings; "Gastrointestinal Regulation of Foot Intake"; The Food Journal of Clinical Investigation; V. 117, N. 1; pp. 13-23; Jan. 2007.

Dakin et al.; "Oxyntomodulin Inhibits Food Intake in the Rat"; Endocrinology; V. 142; No. 10; pp. 4244-4250; 2001.

Dakin et al.; "Peripheral Oxyntomodulin Reduces Food Intake and Body Weight gain in Rats"; Endocrinology; V. 145; No. 6; pp. 2687-2695; Jun. 2004.

Davison; "Activation of Vagal-Gastric Mechanoreceptors by Cholecystokinin"; Proc. West. Pharmocol. Soc.; V. 29; pp. 363-366; 1986.

De Waele et al.; "Endoscopic Volume Adjustment of Intragastric Balloons for Intolerance"; Obesity Surgery; V. 11; pp. 223-224; 2001.

De Waele et al.; "Intragastric Balloons for Preoperative Weight Reduction"; Obesity Surgery; V. 58; pp. 58-60; 2001.

Desai et al.; "Molecular Weight of Heparin Using 13C Nuclear Magnetic Resonance Spectroscopy" Journal of Pharmaceutical Science, V. 84, I 2; 1995, Abstract only.

Doldi et al.; "Intragastric Balloon: Another Option for Treatment of Obesity and Morbid Obesity"; Hepato-Gastroenterology; V. 51, N. 55; pp. 294-307; Jan.-Feb. 2004.

Doldi et al.; "Treatment of Morbid Obesity with Intragastric Balloon in Association with Diet"; Obesity Surgery; V. 10, pp. 583-587; 2000.

Doldi et al; "Intragastric Balloon in Obese Patients"; Obesity Surgery; V. 10, 578-581; 2000.

Ekblad et al.; "Distribution of Pancreatic Peptide and Peptide-YY"; Peptides; V. 23; pp. 251-261; 2002.

El Khoury et al.; "Variation in Postprandial Ghrelin Status Following Ingestion of High-Carbohydrate, High Fat, and High Protein Meals in Males"; Ann Nutr Metab; V. 50; pp. 260-269; 2006.

Galloro et al; "Preliminary Endoscopic Technical Report of an New Silicone Intragastric Balloon in the Treatment of Morbid Obesity"; Obesity Surgery; V. 9, pp. 68-71; 1999.

GinShiCel MH Hydroxy Propyl Methyl Cellulose, Web Page http://www.ginshicel.cn/MHPC.html, Nov. 12, 2008.

Girard; "The incretins: From the concept to their use in the treatment of type 2 diabetes. Part A: Incretins: Concept and physiological functions"; Diabetes and Metabolism; V. 34; pp. 550-559; 2008.

Greenough et al.; "Untangling the Effects of Hunger, Anxiety, and Nausea on Energy Intake During Intravenous Cholecystokinin Octapeptide (CCK-8) Infusion"; Physiology & Behavior; V. 65, No. 2; pp. 303-310; 1998.

Grise et al.; "Peptide YY Inhibits Growth of Human Breast Cancer in Vitro and in Vivo"; Journal of Surgical Research; V. 82; pp. 151-155; 1999.

Grundy; "Signaling the State of the Digestive Tract"; Autonomic Neuroscience: Basic and Clinical; V. 125; pp. 76-80; 2006.

Grundy; "Vagal Control of Gastrointestinal Function"; Bailliere's Clinical Gastroenterology; V. 2; No. 1; pp. 23-43; 1988.

Hallden et al. "Evidence for a Role of the Gut Hormone PYY in the Regulation of Intestinal Fatty Acid Binding Protein Transcripts in Differentiated Subpopulations of Intestinal Epithelial Cell Hybrids"; Journal of Biological Chemistry; V. 272 (19); pp. 125916-126000; 1997.

Hameed et al.; "Gut hormones and appetite control." Oral Diseases; V. 15; pp. 18-26; 2009.

Hassan et al.; "Effects of Adjuvants to Local Anesthetics on Their Duration III Experimental Studies of Hyaluronic Acid" Abstract Pub Med [Acta Anesthesiol Scand.; 29 (4): 384-8], 1 page; May 1985.

Hodson et al.; "Management of Obesity with the New Intragastric Balloon"; Obesity Surgery; V. 11, pp. 327-329, 2001.

Holzer; "Gastrointestinal Afferents as Targets of Novel Drugs for the Treatment of Functional Bowel Disorders and Visceral Pain"; European Journal of Pharmacology; V. 429; pp. 177-193; 2001.

Houpt; "Gastrointestinal Factors in Hunger and Satiety." Neuroscience and Behavioral Reviews; V. 6; pp. 145-164; 1982.

Iverson et al.; "Recent Advances in Microscale Pumping Technologies: A Review and Evaluation"; Microfluid Nanofluid; vol. 5; pp. 145-174; Feb. 19, 2008.

Jones; "Molecular, pharmacological, and clinical aspects of liraglutide, a oncedaily human GLP-1 analogue"; Molecular and Cellular Endocrinology; V. 297; pp. 137-140; 2009.

Kerem et al.; "Exogenous Ghrelin Enhances Endocrine and Exocrine Regeneration in Pancreatectomized Rats"; J Gastrointest Surg.; V.13; pp. 775-783, 2009.

Kesty et al.; "Hormone-based therapies in the regulation of fuel metabolism and body weight"; Expert Opin. Biol. Ther.; V. 8; No. 11; pp. 1733-1747; 2008.

Kissileff et al.; "Peptides that Regulate Food Intake: Cholecystokinin and Stomach Distension Combine to Reduce Food Intake in Humans"; Am. J. Physiol. Regul. Integr. Comp. Physiol; V. 285; pp. 992-998; 2003.

Kojima et al.; "A role for pancreatic polypeptide in feeding and body weight regulation." Peptides; V. 28; pp. 459-463; 2007.

Kulicke et al. "Visco-Elastic Propeerties of Sodium Hyaluronate Solutions," American Institute of Physics; pp. 585-587; 2008.

Lap-Band AP System Adjustable Gastric Banding System With OmniformTM Design: Directions for Use (DFU); Allergan, 16 pages; 2009.

Le Roux et al.; "Gut Hormone Profiles Following Bariatric Surgery Favor an Anorectic State, Facilitate Weight Loss, and Improve Metabolic Parameters"; Ann. Surg; V. 243; No. 1; pp. 108-114; Jan. 2006.

Liu et al.; "Adjuvant Hormonal Treatment With Peptide YY or Its Analog Decreases Human Pancreatic Carcinoma Growth"; The American Journal of Surgery; V. 171; pp. 192-196; Jan. 1996.

Mathus-Vliegen et al. "Intragastric Balloons for Morbid Obesity: Results, Patient Tolerance and Balloon Life Span"; Br. J. Surg.; V. 77, No. 7, pp. 76-79; Jan. 1990.

Mathus-Vliegen et al. "Treating Morbid and Supermorbid Obesity" International Journal of Gastroenterology; V. 5, No. 1, pp. 9-12; 2000.

Medeiros et al.; "Processing and metabolism of Peptide-YY: Pivotal roles of Dipeptidase-IV, Aminopeptidase-P, and Endopeptidase-24. 11"; Endocrinology; V. 134, No. 5; pp. 2088-2094; 1994.

Naslund et al. "Pranidal subcutaneous injections of glucagon-like peptide-1 cause weight loss in obese human subjects"; British Journal of Nutrition; V. 91; pp. 439-446; 2004.

Potier et al.; "Protein, amino acids, and the control of food intake"; Current Opinion in Clinical Nutrition and Metabolic Care; V. 12; pp. 54-58; 2009.

Qian et al.; "Pulmonary delivery of a GLP-1 receptor agonist, BMS-686117"; International Journal of Pharmaceutics; V. 366; pp. 218-220; 2008.

Rang et al.; "Pharmacology"; V. 5; pp. 203, 397, 402, 524; 2004.

Raybould et al.; "Integration of Postprandial Gastrointestinal Tract: Role of CCK and Sensory Pathways"; Annals of New York Academy of Science; pp. 143-156; 1994.

Renshaw et al. "Peptide YY: A Potential Therapy for Obesity"; Current Drug Targets; V. 6; pp. 171-179; 2005.

Sannino et al.; "Crosslinking of Cellulose Derivatives and Hyaluronic Acid with Water-Soluble Carbodiimide" Polymer 46; pp. 11206-11212; 2005.

Shechter et al.; "Reversible PEGylation of peptide YY3-36 prolongs its inhibition of food intake in mice"; FEBS Letters; V. 579; pp. 2439-2444; 2005.

Silver et al.; "Physical Properties of Hyaluronic Acid and Hydroxypropylmethylcellulose in Solution: Evaluation of Coating Abillity" Journal of Applied Biomaterials, V. 5; pp. 89-98, 1994.

Small et al.; "Gut hormones and the control of appetite"; TRENDS in Endocrinology and Metabolism; V. 15. No. 6; pp. 259-263; Aug. 2004.

Stanley et al.; "Gastrointestinal Satiety Signals III. Glucagon-like Peptide 1, oxyntomodulin, peptide YY, and pancreatic polypeptide"; Am. J. Physiol Gastrointest Liver Physiol; V. 286; pp. 693-697; 2004.

Tezel; "The Science of Hyaluronic Acid Dermal Fillers," Journal of Cosmetic and Laser Therapy (2008) 10: pp. 35-42.

Tolhurst et al.; "Nutritional regulation of glucagon-like peptidel secretion"; J. Physiol.; V. 587, No. 1; pp. 27-32; 2009.

Totte et al.; "Weight Reduction by Means of Intragastric Device: Experience with the Bioenterics Intragastric Balloon"; Obesity Surgery; V. 11, pp. 519-523; 2001.

Tough et al.; "$Y_4$ Receptors Mediate the Inhibitory Responses of Pancreatic Polypeptide in Human and Mouse Colon Mucosa"; The Journal of Pharmacology and Experimental Therapeutics; V. 319, No. 1; pp. 20-30; 2006.

Tseng et al; "Peptide YY and cancer: Current findings and potential clinical applications"; Peptides; V. 23; pp. 389-395; 2002.

Valassi et al.; "Neuroendocrine control of food intake"; Nut. Metab. & Cariovasc. Disease; V. 18; pp. 158-168; 2008.

Van Der Lely et al.; "Biological, Physiological, Pathophysiological Aspects of Ghrelin"; Endocrine Reviews; V. 25, No. 3; pp. 426-457; 2004.

Verdich et al. "A Meta-Analysis of the Effect of Glucagon-Like-Peptide-1 (7-36) Amide on ad Libitum Energy Intake in Humans"; J. Clin. Endocrinal. Metab. V. 86; pp. 4382-4389; Sep. 2001.

Wahlen et al.; "The BioEnterics Intragastric Balloon (BIB): How to Use It"; Obesity Surgery; V. 11; pp. 524-527; 2001.

Wang et al.; "Plasma Ghrelin Modulation in Gastric Band Operation and Sleeve Gastrectomy"; Obes. Surg.; pp. 357-362; 2008.

Weiner et al.; "Preparation of Extremely Obese Patients for Laparoscopic Gastric Banding by Gastric Balloon Therapy"; Obesity Surgery; V. 9, pp. 261-264, 1999.

Wynne et al.; "Subcutaneous Oxyntomodulin Reduces Body Weight in Overweight and Obese Subjects: A Double-Blind Randomized, Controlled Trial"; Diabetes; V. 54; pp. 2390-2395; 2005.

Yuzuriha et al.; "Gastrointestinal Hormones (anorexigenic peptide YY and orexigenic ghrelin) influence neural tube development"; FASEB J.; V. 21; pp. 2108-2112; 2007.

* cited by examiner

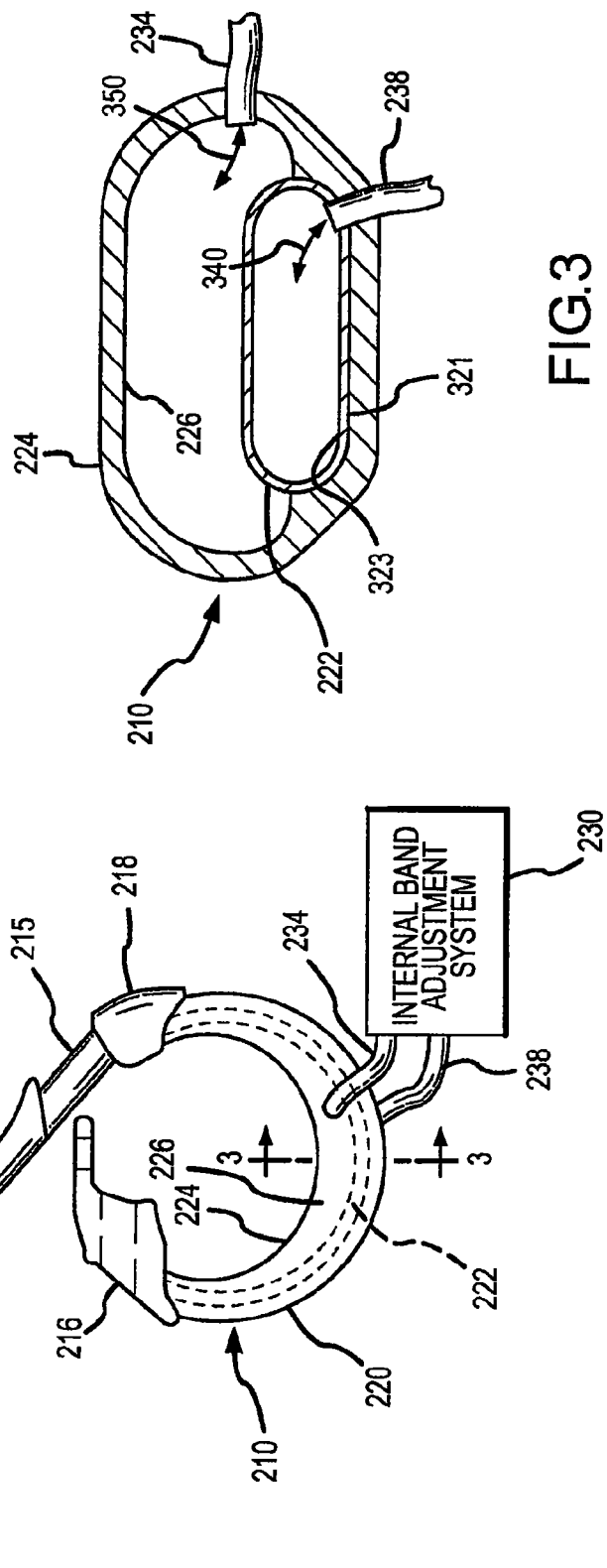

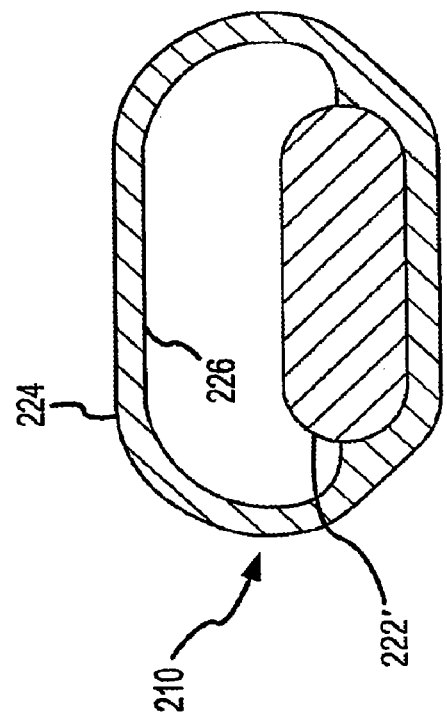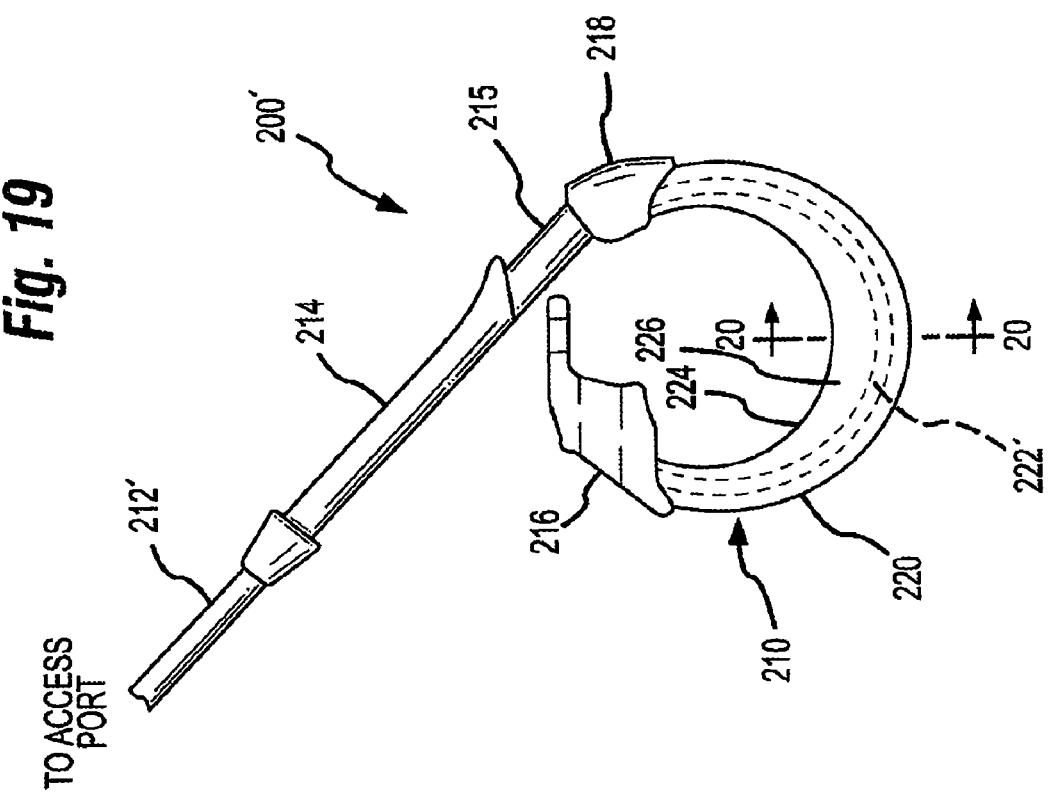

HYDRAULIC GASTRIC BAND WITH COLLAPSIBLE RESERVOIR

CROSS REFERENCE TO RELATED APPLICATIONS

This application is a continuation application of U.S. patent application Ser. No. 12/850,038, filed on Aug. 4, 2010, which is a continuation application of Ser. No. 11/754,091, filed on May 25, 2007, now U.S. Pat. No. 7,798,954, which is a continuation-in-part application of U.S. patent application Ser. No. 11/472,902, filed on Jun. 22, 2006 now U.S. Pat. No. 8,043,206, which is a continuation-in-part application of International Application No. PCT/US06/000013, filed on Jan. 4, 2006. The entire contents of each of these applications are hereby incorporated by reference herein.

FIELD OF THE INVENTION

The present invention relates, in general, to devices and methods for controlling obesity, and, more particularly, a gastric band or gastric band assembly/system, and corresponding methods, configured for self-monitoring and adjustment of the size, i.e., internal diameter, of the gastric band so as to provide ongoing adjustment of stoma size in a patient.

BACKGROUND OF THE INVENTION

Severe obesity is an increasingly prevalent chronic condition that is difficult for physicians to treat in their patients through diet and exercise alone. Gastrointestinal surgery is used by physicians to treat people who are severely obese and cannot lose weight by traditional means or who suffer from serious obesity-related health problems. Generally, gastrointestinal surgery promotes weight loss by restricting food intake, and more specifically, restrictive operations limit food intake by creating a narrow passage or "stoma" from the upper part of the stomach into the larger lower part, which reduces the amount of food the stomach can hold and slows the passage of food through the stomach. Initially, the stoma was of a fixed size, but physicians have more recently determined that the procedure is more effective if the stoma can be adjusted to alter its size.

One of the more commonly used of these purely restrictive operations for obesity is adjustable gastric banding (AGB). In an exemplary AGB procedure, a hollow band (i.e., a gastric band) made of silicone elastomer is placed around the stomach near its upper end, creating a small pouch and a narrow passage (i.e., a stoma) into the rest of the stomach. The band is then inflated with a saline solution by using a non-coring needle and syringe to access a small port that is placed under the skin. To control the size of the stoma, the gastric band can be tightened or loosened over time by the physician or another technician extracorporeally by increasing or decreasing the amount of saline solution in the band via the access port to change the size of the passage or stoma.

Providing fine adjustments of the gastric band after initial stoma sizing has proven a significant improvement in the adjustable gastric banding procedure. However, there is an ongoing difficulty in determining when to further adjust the gastric band and how much to increase or decrease the band's size or diameter to achieve a desired stoma size. Numerous gastric bands have been developed to allow a physician or other technician to adjust an implanted gastric band. In general, these band systems include a sensor for measuring or determining parameters associated with the patient and in response, the physician or technician acts to adjust the volume of fluid in the band based on the patient parameters. For example, one adjustable gastric band system determines when the pressure in a patient's stomach exceeds a pre-set limit and provides an alarm to an external control device. A doctor or other operator then responds by loosening the gastric band by removing an amount of fluid from the band via the external access port and fill line. In another gastric band system, components for adjusting the size of the gastric band are implanted within the patient, and when a physical parameter related to the patient, such as stomach pressure or the physical position of the patient, are determined, an external control unit outside the patient's body is operated to power the implanted components to adjust the size of the band, e.g., by adding or removing a preset volume of fluid from the band.

While providing improved control over adjustable gastric bands, the existing gastric bands do not meet the needs of patients. In part, the deficiencies in the existing adjustable gastric bands are due to the need for the patient to be treated by a doctor or other technician to adjust the size of the gastric band and the formed stoma via an external control unit. Other deficiencies are related to the unreliability or inaccuracy of sensing parameters related to the patient and correlating this to a desired stoma size. Further, some of the existing gastric bands require insertion of sensors into the patient, such as into or onto the stomach to determine stomach pressure. Due to these and other limitations of existing technologies, there remains a need for an improved gastric banding system, and associated adjustment methods, for providing improved adjustments to the size of a stoma in a patient being treated for obesity.

SUMMARY OF THE INVENTION

The present invention addresses the above and other problems by providing a self-regulating gastric band system for implanting in an obese patient to automatically adjust the size of a stoma on a periodic or ongoing basis. The system is "self-regulating" in some embodiments as it includes a sensor for sensing a property or parameter of an implanted expandable gastric band and a band adjustment assembly or system that adjusts the size of the expandable gastric band in response to the sensed band property. For example, a physician or clinician may set an operating range for the property in memory of the system prior to implanting or after via an external control device. The sensor operates to periodically, on an ongoing basis, or upon being activated to sense the band property (such as fluid pressure within an expandable inner ring or member of the band). The sensor or a controller operates to determine if the band is within the desired range based on the sensed band property, and if not, the controller acts to adjust the size of the band to bring the band or its sensed property back into the operating range, such as by operating a pump assembly to move fluid between a fluid reservoir and the expandable inner ring. The self-regulating gastric band system typically also includes a housing for enclosing the system components implanted with the gastric band and a local power source that is implanted to provide power to various system components such as pumps, the sensor, and the controller. In this manner, embodiments of the gastric band system may be considered "set-it and forget-it" gastric banding treatments for obesity.

More particularly, a gastric band adjustment assembly is provided for placing in a patient while implanting the gastric band. The assembly includes a sensor used for taking pressure readings or sensing pressure of fluid in a lumen of an expandable portion of the gastric band. A pump assembly is connected to the lumen, and a controller is provided that operates the pump assembly to adjust a volume of the fluid in the lumen based on the pressure readings and a target pressure defined for the gastric band (e.g., a desired pressure for the band stored in memory of the assembly). The assembly further includes a pressure adjusting module (e.g., a software/hardware application run by the controller) that processes the pressure readings to provide a setting of the target pressure. This processing may include determining pressure variations/standard deviations at first and second values or data ranges for the volume of fluid (i.e., at first and second fill levels or increments) and then, setting the target pressure to correspond to one of the first and second values or volumes for which the pressure variations are determined to be lower and, in some cases, to be lower than a predefined maximum pressure variation value or pressure variation limit for the gastric band. For example, the pressure variation limit may be less than about 0.5 PSI, less than 0.3 PSI, or even more preferably less than about 0.1 PSI, and a fill volume may be set that corresponds to the target pressure. The adjusting module may further operate to monitor pressure readings after the band is filled to the fill volume and to adjust the target pressure when pressure variations exceed the pressure variation limit so as to adapt automatically to changing treatment conditions. An external control device may be used to wirelessly communicate with the controller to modify the target pressure and/or the fill volume and to retrieve the pressure readings, which may be displayed such as in graph form on a monitor of the external control device to provide a physician feedback during band adjustment operations.

According to another aspect of the invention, a method is provided for adjusting volume of fluid in an expandable portion of a gastric band. In a patient, a gastric band is implanted or placed such that an expandable inner ring engages the patient's stomach and/or esophagus to form a stoma. The method also includes providing a sensor operably coupled with the gastric band for taking pressure readings of fluid in the expandable inner ring. A first volume of fluid is injected into the inner ring, the sensor is operated for a period of time to collect a first set of pressure readings, and then a pressure adjustment module is used to process the first set of pressure readings to determine a first set of pressure variations (e.g., standard deviations, differences between maximum and minimum pressures, or the like). The method continues with injecting an additional amount of fluid into the inner ring to provide a second volume of fluid in the gastric band. Then, the sensor operates to gather a second set of pressure readings and the pressure adjustment module processes these pressure readings to determine a second set of pressure variations. The method continues with comparing the first and second sets of pressure variations to a pressure variation limit. A fill volume is then set for the gastric band that is equal to or proximate to the first or second volume depending on which had pressure variations that were less than the pressure variation limit. If both volumes have pressure variations less than the pressure variation limit, the method may include incrementally injecting additional amounts of fluid into the inner ring and then repeating the steps of operating the sensor, determining the pressure variation, comparing the pressure variation limit, and setting the fill volume until the pressure variation limit is exceeded. This method may be performed by an internal band adjustment system or by an external controller with the use of a pressure sensor provided at or near an access port that is connected to the inner ring by a fill line.

According to another aspect of the invention, a method is provided for adjusting the diameter or perimeter of the band and monitoring the pressure inside a shell that is filled with a fluid, a gas, a gel, or a solid and that lines the inner surface of the band. By changing the diameter or perimeter of the band by mechanical or other means, changes in pressure are realized inside the fluid filled shell. As noted above, the pressure variation could be monitored over time as the band diameter is adjusted to monitor and analyze to set the band size below the maximum set limit of variation (e.g., to set the perimeter or diameter size). The use of the controller, pressure adjusting module, and external controller or monitoring device and other features of the other embodiments are applicable at least in some cases to this aspect to the invention.

According to another aspect of the invention, the method for self analyzing the data above may be applied to a manual access port used in conjunction with a hydraulically adjusted gastric band. In such an embodiment, a pressure sensor is placed inside the access port or inside the system fluid path during monitoring (sensor could be placed in a syringe or syringe adaptor) and used to remotely query data from an external hand held (or desk top or the like) controller. The band is adjusted (in addition to or in place of adjusting by the automated internal adjustment system) using a manual needle and syringe, and pressure data is in some cases collected during incremental fill volumes. The external or "remote" controller includes a processing module(s) that analyzes the data for pressure variation and indicates the optimal fill volume to the adjusting physician based on data analysis (e.g., by displaying sensed pressures, determined pressure variations, and/or a calculated fill volume for the particular band/fill line/port design based on analysis of the sensed pressures and determined pressure variations). As noted earlier, this data could be displayed graphically and/or by numerically on the controller to indicate the ideal pressure setting for the access port.

In accordance with one aspect of the invention, an implantable adjustable gastric band assembly for placement in a patient comprises a gastric band having a fluid-inflatable member with an internal lumen disposed around an inner periphery thereof. A pump assembly connects to the lumen and a controller for operating the pump assembly adjusts a volume of the fluid in the lumen. An expandable fluid reservoir in fluid communication with the pump assembly has a balloon-like structure for storing a volume of fluid for use in adjusting the volume of fluid in the lumen. Desirably, the fluid reservoir is a separate device from the gastric band. Alternatively, the fluid reservoir is part of the gastric band, such as an outer lumen of the gastric band. In accordance with one embodiment, an access port leads to a fill tube through which fluid can flow into the internal lumen of the inflatable member of the gastric band, and the fluid reservoir is provided along the fill tube. For instance, the fluid reservoir is an elongated balloon placed along the fill tube. Desirably, the assembly further includes a protective sheath that collapses around the fluid reservoir and expands therewith to provide protection against damage.

Another embodiment of the invention is an implantable adjustable gastric band assembly for placement in a patient comprising a gastric band having a fluid-inflatable member with an internal lumen disposed around an inner periphery thereof. A fill tube in fluid communication with the internal lumen extends from the fluid-inflatable member to a fill port. An elongated fluid reservoir extends along a substantial part of the fill tube for storing a volume of fluid and is in selective fluid communication with the internal lumen of the gastric band. Preferably, the fluid reservoir is expandable, and a protective sheath collapses around the fluid reservoir and expands therewith to provide protection against damage. In one construction, the fluid reservoir and fill tube are co-extruded. For instance, the fluid reservoir and fill tube are co-extruded and the reservoir collapses around at least a portion of the fill tube in a first, deflated state and expands to be substantially adjacent the fill tube in a second, inflated state of the reservoir.

The implantable adjustable gastric band assembly may also have a sensor for taking pressure readings of fluid in the internal lumen of fluid-inflatable member of the gastric band, a pump assembly connected to the lumen, a controller for operating the pump assembly to adjust a volume of the fluid in the lumen based on the pressure readings and a target pressure for the gastric band, and optionally a pressure adjusting module for processing the pressure readings and setting the target pressure.

A still further aspect of the invention comprises an implantable adjustable gastric band assembly for placement in a patient. The assembly includes a gastric band having a fluid-inflatable member with an internal lumen disposed around an inner periphery thereof. An expandable fluid reservoir having a balloon-like structure stores a volume of the fluid for use in adjusting the volume of fluid in the lumen. A protective outer sheath desirably remains around the exterior of an expandable portion of the fluid reservoir in both a first, deflated state, and a second, inflated state of the reservoir.

In one particular embodiment, the assembly includes an access port leading to a fill tube through which fluid can flow into the internal lumen of the inflatable member of the gastric band, and the fluid reservoir is provided along the fill tube. The fluid reservoir and the fill tube may be co-extruded wherein the reservoir collapses around at least a portion of the fill tube in a first, deflated state and expands to be substantially adjacent the fill tube in a second, inflated state of the reservoir. Indeed, the protective sheath, fluid reservoir and fill tube may be co-extruded. Alternatively, the protective sheath is a split tube attached to the fluid reservoir/fill tube co-extrusion and is biased into a compact configuration around the fluid reservoir/fill tube in the first, deflated state of the reservoir, and spreads open while still surrounding the reservoir in the second, inflated state of the reservoir.

BRIEF DESCRIPTION OF THE DRAWINGS

Features and advantages of the present invention will become appreciated as the same become better understood with reference to the specification, claims, and appended drawings wherein:

FIG. 2 illustrates a gastric band with an interconnected internal band adjustment system in fluid communication with lumens of the band such as may be used in a self-regulating gastric band system such as in the system of FIG. 1;

FIG. 3 is a cross sectional view of the gastric band of FIG. 2 taken at line 3-3 illustrating the inner, expandable lumen used for fine tuning the inner diameter or size of the gastric band and an outer lumen providing a local or internal reservoir for fluid for use in expanding (and deflating or shrinking) the inner, expandable lumen;

FIG. 19 illustrates an alternative self-regulating gastric band having a fluid reservoir that is separate from the band;

FIG. 20 is a cross sectional view of the gastric band of FIG. 19 taken at line 20-20 illustrating the inner, expandable lumen used for fine tuning the inner diameter or size of the gastric band;

DETAILED DESCRIPTION OF THE PREFERRED EMBODIMENTS

In brief, the invention is directed to a self-regulating gastric band or band system that enables an operator (e.g., a physician or technician) to set operational parameters for a gastric band prior or after implantation in a patient. The self-regulating gastric band then is operable to directly monitor properties of or associated with the gastric band, to determine if these monitored or sensed properties are within the set operational parameters or bounds, and then, if not within the bounds, to automatically adjust the size of the gastric band (i.e., its inner diameter that establishes the size of a stoma in the patient's stomach) such that the monitored or sensed property or properties are within the present operation range or bounds.

Self-regulating gastric band systems of the invention generally can be used with numerous gastric band designs with many embodiments being particularly useful for those that include an inflatable portion or inner lumen that is expanded or contracted by increasing or decreasing the volume of fluid contained therein. Generally, the gastric band systems of the invention include one or more sensors for directly sensing a band parameter, such as pressure of the fluid in the inflatable portion, and a controller that processes this sensed band parameter or property to determine whether to add or withdraw fluid from the band to finely tune its size (and the corresponding stoma size). A local fluid reservoir may be provided that is connected to a pump assembly, which is controlled by the controller to pump fluid into or out of the band. In one embodiment, the local fluid reservoir is provided within the gastric band itself, e.g., in an outer lumen or reservoir ring or member. An internal fill line or tube is connected between the pump assembly and the inflatable portion or member of the gastric band to allow the volume to be controlled locally (e.g., instead of or in addition to a standard access port). Power for the pump assembly, controller, and sensor is typically also provided local to the gastric band, i.e., intracorporeally or adjacent the stoma and gastric band in the patient, rather than from an external power source such as an induction power source. Memory is also associated with the controller to store band data and band operating ranges or bounds that are used to determine when to adjust the size of the gastric band, and these operating ranges or bounds (i.e., range limits) may be set before implantation or later set or modified via communications with an external controller/monitor. These and other features of the invention are described in detail in the following description with reference to FIGS. 1-10.

Figure 1:
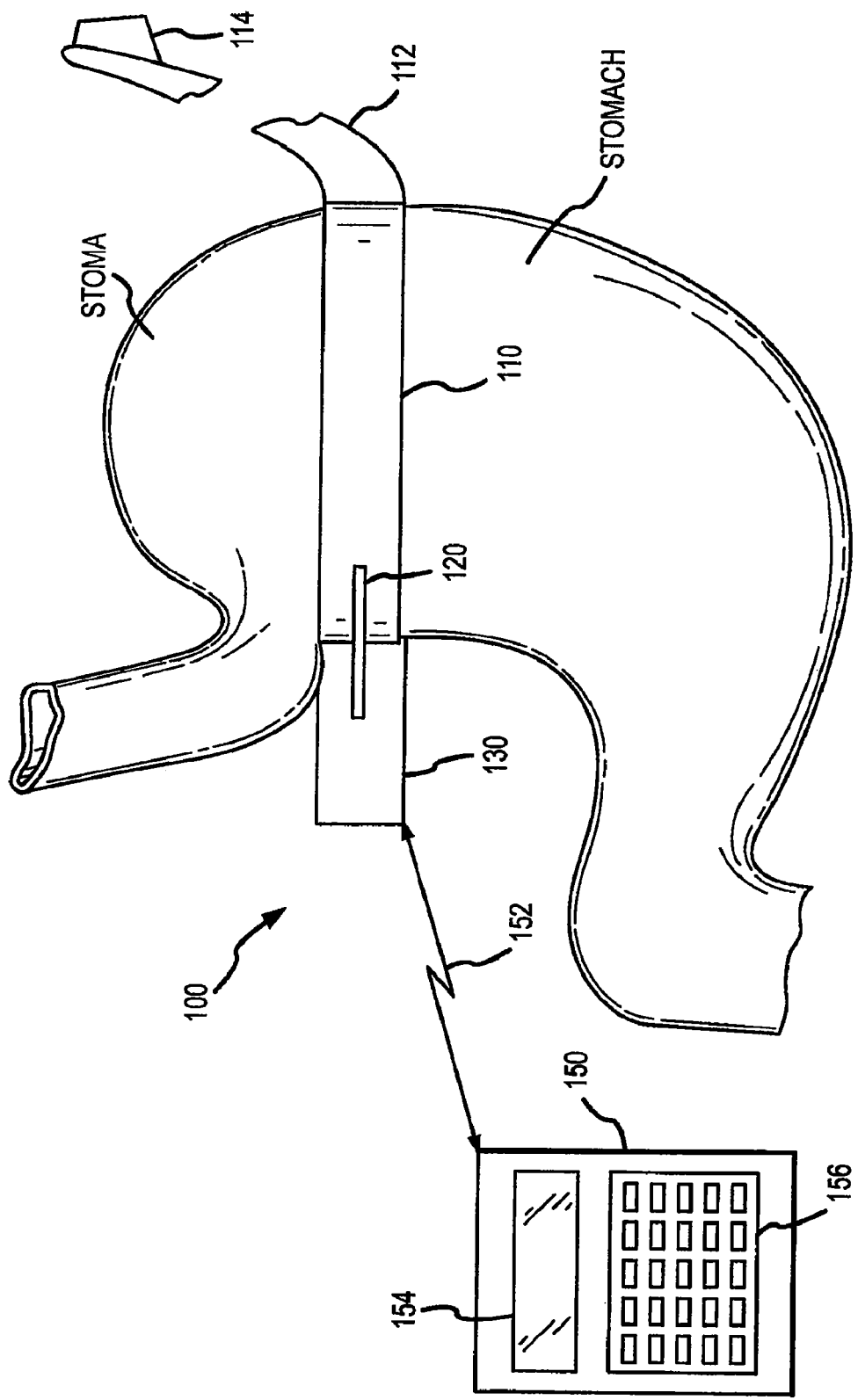
FIG. 1 illustrates a self-regulating (i.e., self-monitoring and self-adjusting) gastric band system according to the present invention as it may appear when installed in a patient.

FIG. 1 illustrates a self-regulating gastric band system or apparatus 100 as it may appear when installed in a patient being treated for morbid obesity. As shown, the system 100 is being used to form a stoma or smaller opening in the upper portion of the stomach near the esophagus to restrict food intake and flow. It is often useful or even necessary to vary the size of the stoma to properly treat a patient. Hence, the self-regulating gastric band system 100 is adapted for self-regulation of its size based on sensed band parameters and operating parameters (such as a range of operating parameters with set upper and lower limits). The gastric band system 100 includes a gastric band 110 that is inflatable by external or extracorporeal actions via a fill tube or line 112 that is connected to an access port 114 through which fluid can be pumped into the inflatable portion or member of the gastric band 110. Such a filling is typically performed as part of an initial sizing of the stoma as part of the implanting process performed by the physician or other technician.

The band 110 and other components of the system 100 are implanted in the same or similar surgical procedure as used with existing expandable or inflatable gastric bands. For example, a surgeon would typically dissect the tissues around the stomach to create a tunnel for the band 110. The band 110 is then introduced into the patient's abdomen, e.g., through an 18 mm or other sized trocar or the like or directly through the trocar hole in the skin. The band 110 is then tunneled in place and positioned around the stomach. The other components of the system 100 including the internal band adjustment system or unit 130 are placed near the stomach (such as just below the skin on top of the sternum or on the rectus muscle sheath proximate the access port) with fluid connection provided via fill/drain line 120 to the gastric band 110 and particularly to the inflatable or expandable member or portion of the band 110 (additional connections are provided in embodiments in which the band 110 also includes a local fluid reservoir for use in sizing the band 110). In other embodiments, the connection 120 is provided to the fill line 112 such that another connection to the band 110 is not required.

The self-regulating gastric band system 100 includes an internal band adjustment assembly or unit 130 that functions to sense a band parameter, such as fluid pressure in the inflatable or expandable portion or lumen or in the fill line 112 or a property such as surface tension/strain on the band or the like, to determine if this sensed or monitored band property or parameter is within a predefined acceptable band operating range, and if not, to adjust the size of the gastric band 110. Typically, the size adjustment is achieved via the fill/drain line 120 by adding or removing liquid, such as saline, to or from the band 110, which is explained in detail with reference to FIGS. 4-10. The system 100 further includes an external monitoring or control device 150 that includes a display element 154 that is used to display data received via wireless communications 152 with the internal band adjustment system or unit 130, to display data such as new operational parameters to be sent to the internal system 100, or to display historic or other data associated with the gastric band 110. The external monitoring device 150 also includes a keypad or other input area 156 for allowing an operator to enter data or input (such as to request data from the internal system 130, to input a new setting for the gastric band 110 by adjusting its operating range, or the like).

The gastric band 110 may take many forms to practice the invention. For example, but not as a limitation, the gastric band 110 may be configured similar to the gastric bands described in U.S. Pat. Nos. 5,226,429 and 5,601,604, which are incorporated herein in their entirety by reference. Alternatively, the gastric band 110 may include one of the gastric bands available from Allergan, Inc. (e.g., one of the bands in the LAP-BAND™ family of expandable gastric bands such as the 9.75, 10.0, 11.0 cm, the VG, or AP LAP-BANDs). Other gastric bands from various band manufacturers/distributors that could be used for this application include, but are not limited to: the Obtech (Ethicon) band, the AMI band, the Heliogast band, the Minimizer (Pier) band, and Cousin Bioband.

FIGS. 2 and 3 illustrate an embodiment of a self-regulating gastric band assembly 200 that includes one exemplary gastric band 210 that may used to implement the invention (such as for use as band 110 in system 100). The gastric band assembly 200 includes the gastric band 210 and an internal adjustment system 230, as described with regard to FIG. 1 and in more detail with FIGS. 4-10, that generally includes a sensor(s) for directly sensing properties of band 210, a controller with memory, an internal power supply, and a pump assembly (not shown in FIGS. 2 and 3 but described with reference to FIGS. 4-10).

The gastric band 210 includes a fill tube or line 212 that is used to provide a fluid connection between an access port (not shown) and an expandable or inflatable portion or lumen 226 in the band 210. A belt 214 with a recessed surface 215 and raised portion 218 are provided along with a buckle member 216 to allow initial forming of a circular loop or band of a particular initial size or inner diameter when the band 210 is implanted about a patient's stomach (e.g., to initially set the size to the band at 9 to 11 cm or another useful inner diameter) to provide an initial size of a stoma. To allow additional fine adjustment of the stoma, the gastric band includes an inflatable portion or member that abuts the outer surfaces of the stomach.

As shown, the gastric band 210 includes a shell or molded shell 220, an inner ring 222, and an inflatable portion, member, or balloon 224 made of an elastic or other material that can be increased in size and later reduced in size. The inflatable member 224 includes an internal lumen 226 for received volumes of fluid, e.g., saline or the like. According to one feature of the invention, the gastric band 210 may be configured to provide a local fluid reservoir for storing fluid for expanding or deflating the inflatable portion 224. In this regard, the inner ring 222, which is typically made of a more rigid material than the inflatable member 224 and is attached at 321 (such as with adhesive) to the shell 220, includes a lumen or reservoir 323 for storing fluid that later can be pumped into the lumen 226 of inflatable portion 224 by the internal adjustment system 230. The lumen or reservoir 323 is useful as a store of fluid because reservoir connection tube or line 238 is provided to the internal band adjustment system 230 (such as to a pump (not shown) in the system 230).

Fluid removed from the reservoir 323 formed by inner ring 222 is pumped via line 340 by the internal band adjustment system 230 to the lumen 226 of the inflatable member 224 to increase the size of the gastric band (i.e., increase the outer diameter of a cross section of the band 210 as shown in FIG. 3) or to reduce the size of the ID formed by the band about the stomach to reduce the size of the stoma formed in a patient. At other times, the internal adjustment system 230 is operated (based on sensed band parameters) to pump fluid from the lumen 226 as shown by arrow 350 via fill/drain line 234 which connects the lumen 226 of the inflatable portion 224 to the internal band adjustment system 230 (or to a pump in the system 230). Such removal of fluid from lumen 226 decreases the size of the band 210 and inflatable member 224 while increasing the ID formed by the band 210 about the stomach and increasing the size of the patient's stoma. The fluid removed from the inflatable portion 224 is pumped into the reservoir 323 as shown by arrow 340 for storage and later use in sizing or adjusting the gastric band 210.

Figure 4:
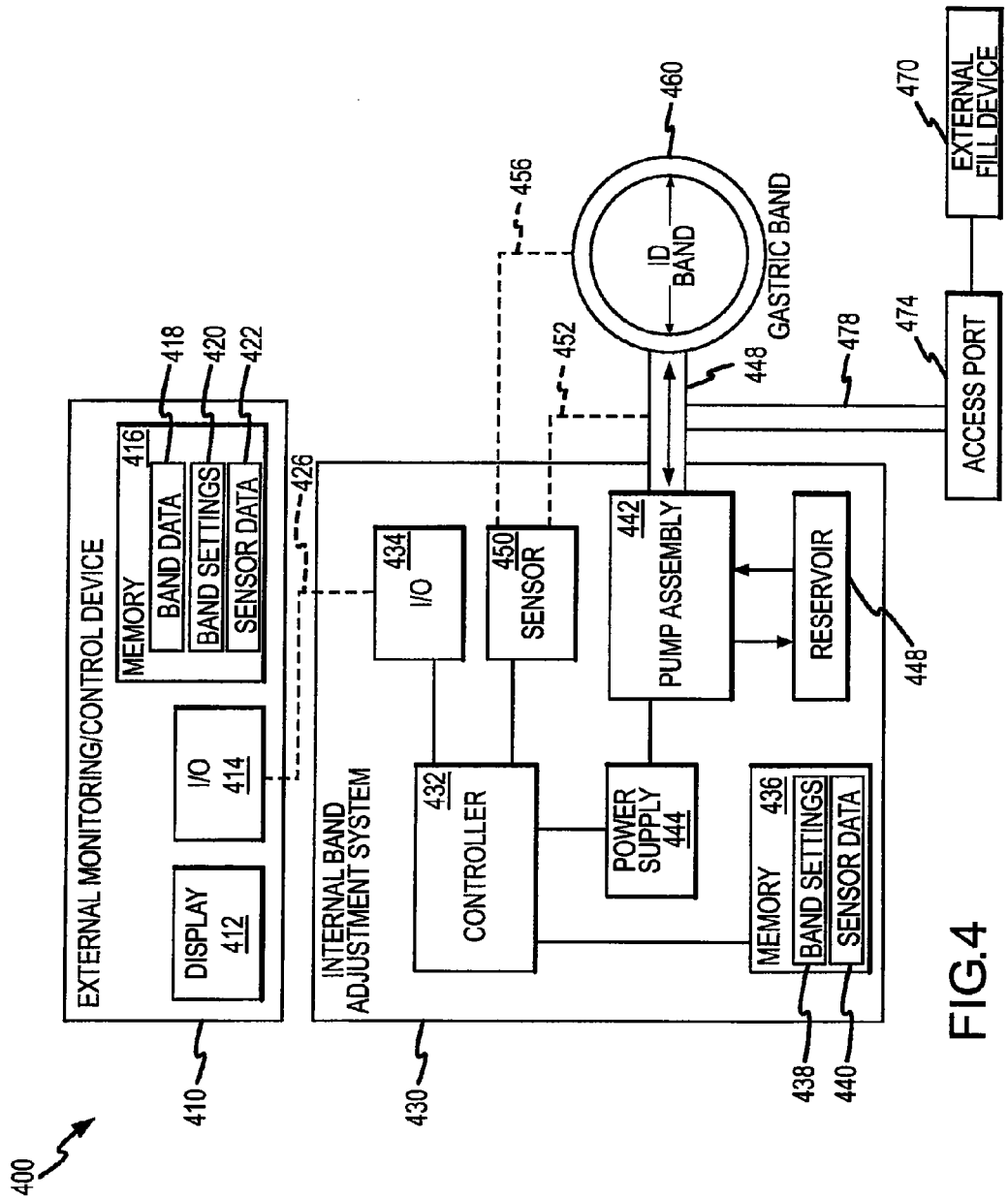
FIG. 4 is a functional block diagram of a self-regulating gastric band system according to one embodiment of the invention.

FIG. 4 illustrates in functional block form an exemplary self-regulating gastric band assembly or system 400. The system 400 includes an external monitoring and/or control device 410 that communicates wirelessly 426 with an internal band adjustment system 430. In use, the internal band adjustment system 430 is implanted along with an expandable or adjustable gastric band 460 in an abdominal cavity of a patient to form a stoma in the patient's stomach to treat obesity, i.e., the gastric band is inflated or deflated by the addition or withdrawal of fluid to change the size of the gastric band and the inner diameter of the band, ID.sub.BAND, formed by the band in its circular configuration. The external monitoring and control device 410 may take the form of a handheld, laptop, or desktop computer and/or communication device that includes a display element 412 for displaying information and an input/output component 414 for allowing a user to input data or information such as a keypad, touchscreen, and/or voice data entry feature and for wireless communications as shown at 426 with an I/O component of the internal band adjustment system 430. The device 410 further includes memory 416 for storing band data 418, such as may be read from system 430 and provided by controller 432 and I/O 434 of internal system 430 and for storing band settings 420, such as operating ranges or bounds (i.e., an upper and lower limit such as for a pressure range) for the gastric band 460 that may be entered with the control device 410 or present in the internal system 430 and later read by the external device 410 for storage in memory 416 and/or for modification or alteration by operation of the external control device 410. The memory 416 may also be used by the external control device 410 for storing sensor data 422 (and, in some cases, patient data) obtained by the sensor 450 of the internal band adjustment system 430.

The internal band adjustment system 430 is shown to include a controller 432, which may include a CPU and code useful for controlling operation of the system 430. The system further includes an I/O element 434 for communicating with the external monitoring and control device 410. Memory 436 is provided in the system 430 for storing band settings 438, i.e., an acceptable operating range for a particular property or parameter of the gastric band 460 that is sensed by the sensor 450 such as an upper or lower pressure limit (e.g., 4 and 5 PSI) when the sensor 450 is a pressure sensor for the fluid in the inflatable portion of the gastric band 460. The band settings 438 may be set for the particular patient or as default settings prior to implanting the system 430 in a patient and/or the band settings 438 may be set or modified after implanting via the external monitoring/control device 410 so as to alter the size of the gastric band 460 and the resulting inner diameter, ID.sub.BAND. The memory 436 may also be used by the controller 432 for storing other sensor and band data 440 such as data collected from the sensor 450 to provide a historical perspective of operation of the gastric band 460 and band information such as band serial number, manufacturer, and the like.

To monitor operation of the gastric band 460, the system 430 includes the sensor 450 which preferably monitors directly properties or physical parameters of the gastric band 460. As shown, the sensor 450 may be provided in or linked to as shown at 452 a pressure transducer or other device in a fluid link or connection 448 between the gastric band 460 and the pump assembly 442 of the system 430. Alternatively, a pressure transducer or other pressure sensing device may be provided as sensor 450 or in communication with the sensor 450 to measure pressure in the gastric band 460 such as by positioning in the inflatable portion of the band 460, at an inlet port to the band 460, in the fill line 478 which is in communication with access port 474 and external fill device 470 (which, in turn, is provided for initial filling of inflatable or expandable portion of the band 460 or for optional later adjusting of the band 460). The sensor 450 may also be positioned so as to otherwise directly sense properties of the band 460 such as shown with line 456, e.g., with a strain sensor indicating surface tension of the band 460 such as on a surface of the inflatable or expandable portion or with other sensing devices useful with measuring the present size of the gastric band 460.

The sensor 450 may include the memory 436 for storing the band settings 438 such that when it senses a parameter of the band 460 that is outside a preset range (such as above a maximum setting or below a minimum setting) the sensor 450 may "wake up" the controller 432 to operate the pump assembly 442. In other words, the sensor 450 may be configured to be intelligent enough to determine when the gastric band 460 is outside a preset operational range and respond by alerting or alarming to cause the controller 432 to operate to control the pump 442 including transmitting the sensed band parameter to allow the controller 432 to act appropriately to adjust the band 460. Alternatively, the sensor 450 may be periodically (or, in some cases, more frequently as to approach nearly continuous) operated to take an additional reading of the band property or parameter (as shown as 452 and 456) and to provide the sensed value to the controller 432 which, in turn, acts to compare the sensed band value with the band settings 438 to determine if adjustments of the band 460 are required or desired.

In either case, a power supply 444 such as a battery or the like is used to power the controller 432 and other power consuming components of the system 430 (such as the pump assembly 442 and the sensor 450). The system 430 further includes pump assembly 442 and an internal reservoir 446. The pump assembly 442 may take a variety of forms (such as those shown in FIGS. 5-10) to hydraulically adjust the size of the band 460 in response to sensor 450 information and the invention is not limited to one particular pump or fluid transfer device. The internal or local reservoir 446 is in fluid communication with the pump assembly 442 and provides fluid (such as saline) for pumping via fill/drain line 448 into the band 460 to increase its size and reduce the ID.sub.BAND and also provides a location for storing fluid that is pumped or allowed to flow based on pressure differentials from the band 460 via the line 448 and pump assembly 442. The reservoir 446 may be provided as a separate component in a housing (not shown) that is used to enclose or encapsulate the internal band adjustment system 430 or the reservoir 446 may be provided as a separate device, such as in the form of a balloon-like structure, that is provided proximate the system 430 housing and the band 460. Further, in some embodiments, the reservoir 446 may be provided as part of the gastric band 460 itself such as in an outer lumen or member of the band shell (as is shown in FIGS. 2-3 and FIGS. 5-10).

With an understanding of the general features of self-regulating gastric band systems, it may be useful now to more fully discuss operation of such systems to effectively adjust the size of an implanted gastric band (such as bands 110, 210, and 460). The pump assembly is typically modular and can be used with any of number of gastric bands, e.g., those currently available from Allergan, Inc. such as the 9.75 cm, 10.0 cm, VGs, or APs LAP-BANDs. The pump in the pump assembly replaces the function of the manually adjustable access port. The materials used to construct the band will generally remain the same as normally employed, and the dimensions of the band, except the tubing in the case of a local reservoir being provided in the shell or tubing, will remain the same. However, alternate materials may be used to implement the invention such as materials selected specifically to improve performance, to increase acid resistance, or to achieve some other desired result. Similarly, there may be a minor change to the band tubing to increase the outer diameter from 0.130 to 0.180 or greater to increase saline capacity in the outer or shell lumen or tubing to act as a reservoir for additional saline or fluid that may be used for future adjustments. The tubing of the gastric band may have 2 lumens to separate the saline for the reservoir and saline that is part of the band (as is shown in FIGS. 2 and 3). In addition, a long extended balloon may be placed along the tubing to act as a reservoir. The pump assembly will generally include one or more pumps (or pump-like devices for moving fluid in and out of the band), electronics, communication components, computer or intelligence components, and a power supply such as a battery or batteries. The internal gastric band adjustment assembly will be sealed inside an outer housing made of a biocompatible material such as acetyl copolymer, PEEK, titanium, or the like. In some embodiments, the power supply is an implantable grade battery that is hermetically sealed in titanium prior to being placed into the pump assembly. The pump assembly may have an over-ride port that allows for manual adjustments if needed such as with external fill device 470 via access port 474 shown in FIG. 4.

In some preferred embodiments, the self-regulating gastric band system functions automatically or as a "set-it-and-forget-it" device. For example, the system may function continually or periodically (such as hourly, daily, weekly, monthly, or some other selected monitoring period) sense a band parameter or property and then adjust such as via inflating and deflating the gastric band hydraulically with saline or another fluid. In some cases, the same or similar specification for saline fill volume and a fill burst of the band will apply to the self-regulating gastric band system. The adjustments in these self-regulating embodiments are performed by the remote actuation of a micropump or pumps coupled with the sensor and with control electronics. The sensor detects directly a parameter or property of the band such as an internal parameter of the band, e.g., an internal band pressure, or an internal or external parameter such as stress and/or strain of the shell. The sensor may also include a linear motion sensor that detects changes in length in the band or in the inflatable portion of the band, with the sensor or controller acting to convert this detected length delta to stoma or band diameter measurements. The sensor may also be a distance sensor functioning to detect the distance between two points to detect a change in position. The sensor could be queried by an external monitoring or control unit via telemetry to gather data on the parameter being monitored for real time feedback to the clinician.

In some cases, the sensor is programmed to "wake up" at intervals (or monitoring periods) to monitor parameters and to adjust the band to the ideal band parameter(s) established through testing or established to better treat a patient over a longer treatment period. If the parameters are not within the ideal range, the sensor will send a command to re-adjust as necessary to ensure that the band reads within the ideal parameter control limits or alternatively, the sensor will merely pass the gathered information from the band to the controller for use in determining whether the band is in a desired operating range. For example, the sensor may "wake up" and determine that the band is monitoring an internal band pressure of "X psi" and determine based on a comparison with preset band parameters that the band needs to be adjusted such that its internal fluid pressure is at "Y psi" which may be a pressure at the midpoint within an operating range or any pressure within that range. The sensor, in this arrangement, will communicate to the controller to cause the controller to activate the implanted pump and command the volume of fluid to be pumped into band or out of the band until the sensor reads within ideal parameter limits, e.g., by operating the pump until the sensor detects an internal fluid pressure in the band within the range or matching the midpoint of the present operating range (or other reset point saved in memory associated with the sensor or with the controller).

The micropump(s) draw power from the implanted battery or power supply to allow for the adjustment, and, if included, the controller also activates one or more check valves to open (see FIGS. 5-10). To inflate the band further or to finely increase its size, the pump pulls fluid from the local reservoir into the band. To deflate the band or to finely decrease its size, the pump will pull fluid from the band back into the reservoir. Once the sensor reads within the specified parameter range, the valves will close to prevent fluid migration. The pump and sensor will then be shut off to conserve power until the sensor "wakes up" again. Just as in current bands, fluid will be used to either inflate or deflate the shell to control the stoma size but in this case the change in size is handled internally using local control and a local fluid reservoir. After the parameter monitored by the sensor has been changed, the sensor will send a command or message to the controller to record the date the parameter was changed, the value of the new setting or sensed band parameter or property, and, in some cases, the delta or amount of the change.

To externally monitor a parameter reading such as a new or adjusted parameter reading from the sensor, a clinician or operator of the system can use a handheld or other sized external monitor and control device external to the patient's body to query the sensor for a reading or to query the controller for a most recently stored value (or both). Aside from the external monitor device and access port, the system is self-contained to monitor and adjust itself. The pump assembly may store a variety of data in addition to the band data and acceptable band operating range such as a serial number that can be remotely read by the external monitoring and control device to identify the implanted device including the implanted gastric band and internal gastric band adjustment system.

The external device often will take the form of a handheld control unit that may feature an LCD display and control panel to operate the device. The handheld may feature a series of menus that allow an operator to program (or read/determine) the implant to contain in memory important information such as the band size, patient's name, implanting physician, and the date it is implanted. The handheld may communicate with the sensor via telemetry through radiowaves. The FDA and globally recognized communications band (WMTS 402-405 MHz) may be used in some embodiment, and an authentication process can be used to ensure that the device cannot be accidentally accessed or controlled by another control mechanism other than the handheld. The telemetry control signal can be sent from approximately a foot or possibly a greater distance from the patient and will typically not require the patient to disrobe to query the sensor or to change its parameters. During adjustments, the handheld external monitoring device is preferably able to read and write information to the implant such as current pressure or parametric data, adjusting physician's name, the date with the handheld device often operating to store or retain the adjustment history in its own memory (this history can be stored in the internal adjustment system, too or only). The handheld device may also be password controlled to prevent unauthorized personnel from querying the device. The display of the handheld, which may include visual and audio outputs, typically will display or output the sensed parameter of the band's condition or physical parameter whether this parameter or property is pressure, stress, strain, and/or linear measurement.

As to the sensor change duration, the sensor query typically will only take a few seconds, but the control of the micropump(s) may take longer, such as approximately 30 seconds per 1 psi of pressure change. The resolution of pressure readings and parameter ranges will be fine and preferably will have greater resolution than is currently possible by manual syringe adjustments. Regarding data storage, at least a portion of the information will be stored directly on the implanted internal system. To retrieve data, the handheld may be used to query the device and display on the screen data, such as the serial number, patient name, doctor's name, band size, fill volume, fill volume, and adjustment history.

As to the implant system's power source, although the above specifically mentions an implanted battery, the implant could be powered by a variety of internal power sources that meet the energy requirements such as the following: (a) kinetic energy creation by body motion stored onto a capacitor; (b) an implanted fuel cell; (c) an implanted power source powered by chemistry of the body; (d) an implanted power source powered by temperature change; and (e) implanted batteries that can be recharged by direct contact. The handheld control device will typically be powered by rechargeable batteries while some embodiments may use other power sources. For example, a power cord may be supplied to allow recharging of the device in between uses with in most embodiments a fully charged device performing a day's worth of queries of a plurality of implanted band systems.

The self-regulating gastric band adjustment system of the present invention presents a number of design advantages. For example, the system provides precise and safe operation and supports telemetric communication with the implant. The system is configured so as to reduce risk of infections and to improve patient comfort. The implantable battery or power source provides a reliable and consistent power supply. The system can be operated to provide feedback on the state of the implant, which can be used for improving therapeutic intervention and patient follow-up.

In some embodiments, the external monitoring and control device, such as device 410 of FIG. 4, is configured to control operation of the internal band adjustment system. In these embodiments, the sensor 450 (or the controller 432) is queried by the external device 410 via telemetry 426 to gather data on the parameter being monitored by the sensor at 452 and/or 456. Based on the current readings, the clinician or operator of the device 410 that is gathering this information can then change the monitoring limits (i.e., the band settings 438 that may be programmed into the sensor 450 when the sensor 450 is configured to intelligently monitor the operating bounds of the band 460) of the parameter such as to increase or decrease pressure or stress and strain of the gastric band. The sensor 450 (or controller 432 by storing new band settings 438) can then reprogrammed to read data and determine if the new data is within the modified control limits. The sensor 450 sends a signal to the control mechanism 432 to adjust the band 460 such that (or until) the sensor 450 reads data (i.e., a gastric band property or parameter) within the control limits (or band settings 420 or 438).

For example, a band may be monitoring or reading a band parameter (such as fluid pressure within the band 460) between 2 and 3 psi when the clinician queries the sensor 450 by operating the external device 410. The clinician, physician, or other operator may then choose to increase the monitoring range of the band to a range having 5 psi as its midpoint. The physician will re-program the sensor 450 to monitor between 4.5 to 5.5 psi (such as by resetting the band settings 420 and/or 438) and send this to the sensor 450 telemetrically 426. The sensor 450 resets its monitoring limits (or the controller 432 resets its band settings 438 for use in comparison of sensor-obtained band parameters) and communicates with the controller 432 to activate the implanted pump assembly 442 such that a volume of fluid is pumped into the band or out of the band until the sensor 450 reads (via 452, 456) within the control limits.

During operation, the pump draws power from the implanted battery or power supply 444 to allow for the adjustment and also activates any check valves to open (as discussed with reference to FIGS. 5-10). To inflate the band 460, the pump assembly 442 pulls fluid from the reservoir 446 into the band 460. To deflate the band 460, the pump assembly 442 pulls fluid from the band 460 back into the reservoir 446. Once the sensor 450 reads within the specified parameter range, appropriate check valves are closed to prevent fluid migration from or to the band 460. To confirm the new pressure (or other band parameter) reading, the clinician or operator uses the handheld 410 to query the sensor 450 for another reading. If confirmed, the pump assembly 442 and sensor 450 are shut off until queried again to conserve power.

FIGS. 5-10 illustrate particular self-regulating gastric band systems that may be employed to practice the invention. Each described system providing an alternative example of an effective pump assembly may be employed in a gastric band system (such as for the pump assemblies of internal band adjustment systems of FIGS. 1-4). The described systems each employ a pressure sensor for use in detecting or determining the fluid pressure in the inflatable or expandable portion of the gastric band (hereafter labeled "inner expandable ring"). However, it should be remembered that the invention is not limited to only a pressure sensor and that many embodiments of the invention (including those described in FIGS. 5-10 with a substitution of the sensor) employ other sensors for directly sensing one or more gastric band properties or physical parameters.

For example, but not as a limitation, the sensors employed may include:

1. Pressure Sensors, such as those available from CardioMems and Tronics Microsystem, SA;
2. Implantable grade stress-strain sensors, e.g., those available from CardioMems and Tronics Microsystem, SA or being developed by these companies individually or in joint efforts with Inamed (the assignee of this patent application);
3. Linear motion sensors, such as those available from Microstrain, Inc. (e.g., see http://www.microstrain.com/images/sensorman.jpg, which is incorporated herein by reference);
4. Distance sensors, such as those distributed by Microstrain, Inc., to measure the distance between two points;
5. Force sensors, such as those distributed by Microstrain, Inc., to measure the force exerted against an area by the saline;
6. Thermal sensors, such as those available or in development by Verichip or by Verichip and Inamed (the assignee of this patent application), to measure a thermal gradient from a low level heat source to approximate distance; and
7. Shell thickness gauge to detect reduction in shell wall thickness due to elongation during expansion.

Figure 5:
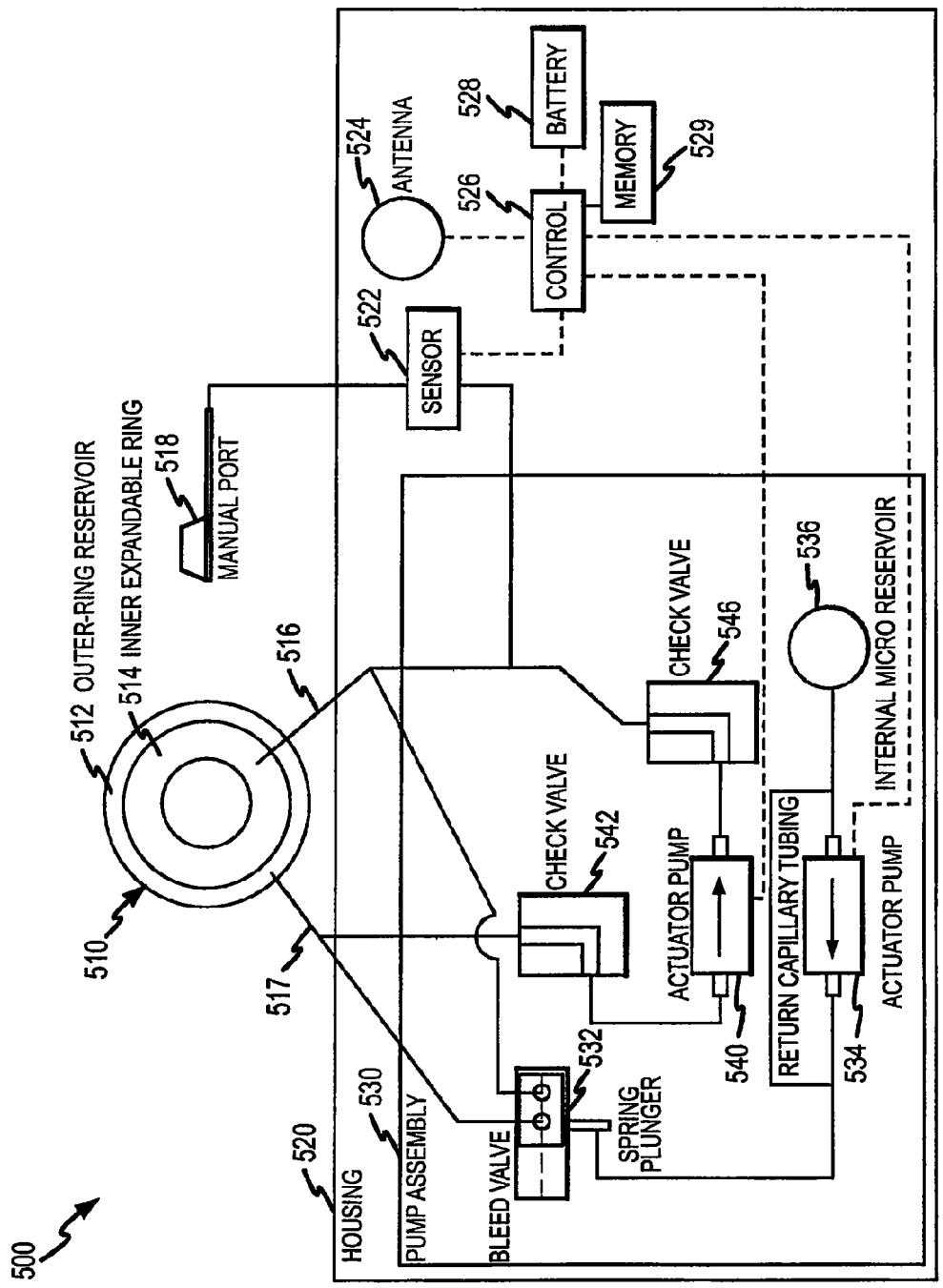
FIG. 5 is a schematic and/or functional block diagram of another embodiment of a self-regulating gastric band system of the invention illustrating more particularly one embodiment of a pump assembly useful for implementing the self-adjusting features of the invention.

Referring to FIG. 5, a schematic of a self-regulating gastric band system 500 is illustrated includes a gastric band 510 for implanting in a patient in a circular configuration about their stomach to form a stoma. The band 510 includes an outer ring reservoir 512 for storing fluid for use in adjusting the size of the band 510, e.g., a lumen may be provided in outer ring or shell of the band that extends at least partially about the circumference of the band 510 (or along the band's length when it is not implanted or placed in its circular configuration such as from a head to a tail of the band or from a first end to a second end of the band). An inner expandable or inflatable ring 514 is provided in the band 510 that is formed of a material that allows it to expand as it received a fluid and to deflate or contract when the fluid is removed or drained.

As discussed above, expandable gastric bands are well known in the art, and nearly any of these known bands may be employed in the system 500 with modifications to include the outer ring reservoir 512 and a fluid connection line 517 (or reservoir fill/drain line or tube) provided to the reservoir 512. During use, the inner expandable ring 514 is filled and drained of fluid via a fill line or tube 516 (which more accurately may be considered a band size adjustment line). Initial sizing of the band 510 is performed via access or manual port 518 that is typically implanted just beneath the patient's skin and which is connected to the fill line 516. Sizing includes a clinician injecting a volume of fluid that is typically selected for the gastric band 510 in an attempt to obtain a desired inner diameter of the band 510. Fine tuning and ongoing "self-regulation" is performed in the system 500 using an internal band adjustment system made up of a pump assembly 530, a sensor 522, a power supply 528 (e.g., one or more batteries), and control and communications components. Although not shown, the system 500 may interact with an external monitor/control device as discussed in detail above. In this regard, an antenna or other wireless communication component 524 is provided in the internal assembly and linked to the control 526, and this antenna 524 allows telemetry to be used to communicate band parameters and other information (again, as discussed in detail above) with the external monitoring/control device.

As illustrated, a housing 520 is provided such that the components of internal band adjustment system can be isolated within the patient. Within the housing 520, a pump assembly 530 is provided along with the sensor 522, the antenna 524, a control 526, a battery or power source 528, and memory 529 (which may be incorporated in the sensor 522 and/or control 526). The sensor 522, control 526, battery 528, and memory 529 provide the functionalities described in detail with reference to FIG. 4 and the preceding description. In this embodiment, the sensor 522 is a pressure sensor for sensing the fluid pressure in the inner expandable ring 514. To this end, the fill line 516 is routed to the housing 520 from the access or manual port 518 through or via contact with the sensor 522 to the inlet of the inner expandable ring 514. In some embodiments, the sensor 522 includes a pressure transducer that can sense directly the back pressure applied by fluid in the inner expandable ring 514 on fluid in the fill line 516. In other embodiments, the sensor 522 or a portion of the sensor 522 is provided in the band 510 such as in or near the inlet port to the inner expandable ring 514 for the fill line 516 or interior to the inner expandable ring 514.

The sensor 522 may be inactive for periods and be activated by the control 526, by an internal timing mechanism, and/or by an external monitoring device. The sensor 522 when activated takes pressure readings and provides these to the control 526 for storage in memory 529 and/or for comparison against a preset operating range (i.e., minimum and maximum pressure limits or bounds such as 3 to 7 psi or more likely 4 to 5 psi, which may be considered band settings) stored in memory 529. Alternatively, the sensor 522 may have intelligence and memory and act to compare the read pressure readings (i.e., directly obtained band property) to band settings programmed into the sensor 522. When the read pressure in the band 510 is outside the band settings, the sensor 522 may awaken the controller 526 to operate to raise or lower the pressure in the band 510 by operating the pump assembly 530 to add or withdraw fluid from the inner expandable ring 514. The battery 528 provides a local power source for power consuming components within the housing 520 such as the control 526, the sensor 522, and any pumps and/or electronic valves in the pump assembly 530. In addition to band settings, the memory 529 may store pressure readings from the sensor 522 and other data related to the gastric band 510 (such as the band identification information, the date of implantation, and the like) as well as, in some cases, data related to the patient (such as patient name, last treatment date/time, and the like).

The pump assembly 530 functions generally to respond to control signals from the control 526 to either pump fluid into the inner expandable ring 514 or to remove or withdraw fluid from the inner expandable ring 514 to thereby size the band 510, whereby a band parameter or property monitored by the sensor 522 is returned to within an operating range or to within band settings. As shown, the pump assembly 530 of system 500 includes a bleed valve 532 (e.g., a ceramic bleed valve or the like operated by a spring plunger) in fluid communication with the outer ring reservoir 512 via line 517. The bleed valve 532 is operated by a pump 534 (e.g., a 7 psi Bartel actuator pump or other pump having the same capacity or a larger or smaller capacity or pressure rating) that is primed with an internal reservoir 536. The bleed valve 532 is also shown to be connected to the fill/drain line 516 of the inner expandable ring 514. The bleed valve 532 is provided to allow the pump assembly 530 to equalize the pressure between the outer ring reservoir 512 and the inner expandable ring 514, which may be desirable in some embodiments (and when not, these components associated with the bleed valve 532 may be omitted from pump assembly 530).

Further (or alternatively), the bleed valve 532 may be used to drain/withdraw fluid from the inner expandable ring 514. In these embodiments, the sensor 522 may sense a pressure that is too high, i.e., above an upper limit of a band setting or operation range, and the control 526 may respond to a signal from the sensor 522 to activate the pump 534 to open the bleed valve 532. A pressure differential between the outer ring reservoir 512 and inner expandable ring 514 results in flow of fluid from the inner ring 514 via fill line 516 and bleed valve 532 to the outer ring reservoir 512 (e.g., this operational embodiment assumes the fluid reservoir 514 is maintained at a lower pressure than fluid in the inner expandable ring 512). The sensor 522 continues to monitor the pressure in the inner expandable ring 512 and when it (or the control 526) determines that the pressure is within the desired operating range (or more typically at or near the center or midpoint of such a range) the control 526 is operated to deactivate the pump 534 to shut the bleed valve 532.

The pump assembly 530 of system 500 also includes a pair of check valves 542, 546 (e.g., Bartel micro check valves or the like) between which is positioned a pump 540 (e.g., a 20-psi Bartel custom actuator pump or the like). One check valve 542 is connected to the outer ring reservoir 512 via line 517, and one check valve 546 is connected to the inner expandable ring 514 via fill line 516. The pump 540 is connected between the check valves 542, 546 with flow during pumping to be from the outer ring reservoir 512 to the inner expandable ring 514. With this arrangement, the pump 540 can be used to increase the size of the band 510 when operated by the control 526 to pump fluid from the outer ring reservoir 512 through the check valves 542, 546 into the inner expandable ring 514. The control 526 provides a shut off signal when the pressure of the fluid in the inner expandable ring 514 is within the set operating range (or at or near a midpoint or other preset point within such a range) as determined by operation of the sensor 522 and control 526.

In some cases, the band 510 may be adjusted to have a smaller size by withdrawing fluid from the inner expandable ring 514 via the pump 540. In these embodiments, the sensor 522 may sense a pressure that is too low (i.e., less than a lower bound or limit of the operating range or band parameters) and provide this information to the control 526. The control 526 then signals the check valves 542, 546 to open and fluid is allowed to flow backwards through the pump 540 to the outer ring reservoir 512 via line 517. This embodiment also assumes that the pressure of the outer ring reservoir 512 is less than that of the fluid in the inner expandable ring 514, and that the pump 540 is configured to allow back flow when it is not actively pumping. When the sensor 522 senses a pressure within the programmed operating range (or a midpoint or other set point within that range) as determined by the sensor 522 and/or the control 526, the control 526 operates to close check valves 542, 546.

Figure 6:
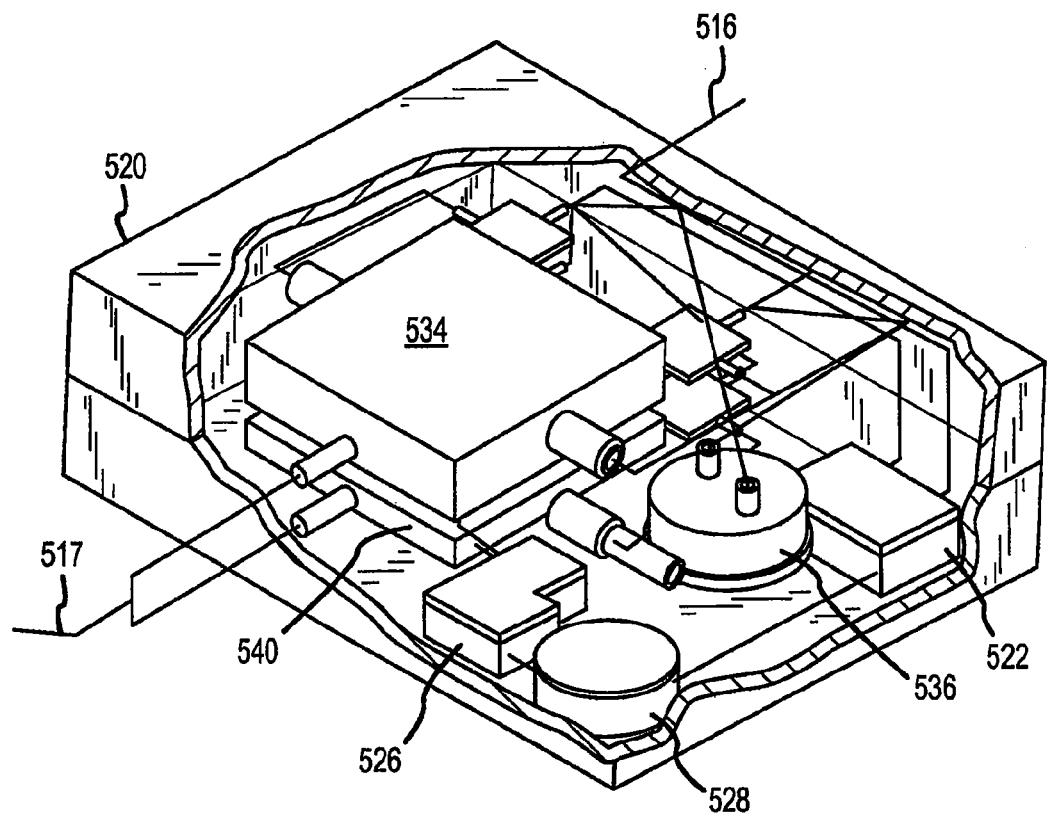
FIG. 6 is a cutaway perspective view of one physical implementation of the pump assembly of the invention, and particularly, of the pump assembly of the system of FIG. 5.

FIG. 6 illustrates one physical arrangement for the pump assembly 530. As shown, the housing 520 is a one-piece unit or box that encloses the sensor 522, the control 526, the battery 528, the pumps 534, 540, and internal reservoir 536 (as well as other components of the pump assembly 530). The housing also provides fluid ports or connection points for the fill line 516 and reservoir connection line 517. The materials used for the housing 520 are preferably biocompatible, and the housing 520 is preferably constructed to be leak resistant (e.g., water or fluid "tight") to support extended use of the pump assembly as an implant. In other embodiments not shown, the housing 520 may take different shapes such as a cylinder, a square, or other useful shape and may be modular such that differing components are provided in two or more enclosures that may be attached or provided as detached modules.

Figure 7:
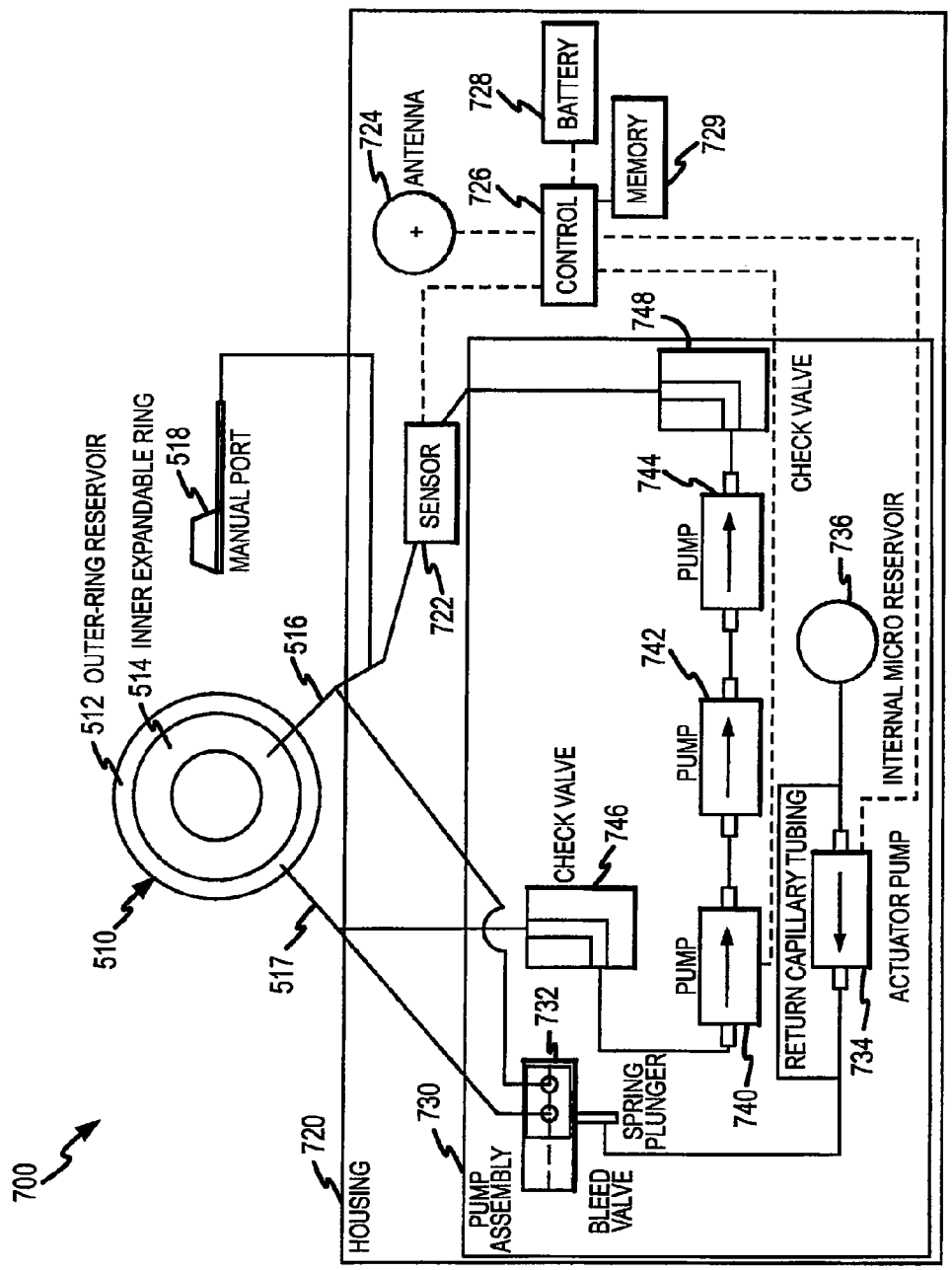
FIG. 7 is a schematic diagram similar to FIG. 5 showing another embodiment of a self-regulating gastric band system of the invention that uses a different pump assembly than the system of FIG. 5.

FIG. 7 illustrates a schematic of another embodiment of a self-regulating gastric band system 700. The system 700 is configured similarly to that of system 500 with an adjustable gastric band 510 having an inner expandable ring 514 and an outer ring reservoir 516 that with fill/drain lines 516 and 518, respectively. An access port 518 is connected to the fill/drain line 516 to allow external filling of the inner expandable ring 514 with saline or other fluid, such as during the implant process to initially size the band 510. In a housing 720, a sensor 722 is provided in fill/drain line 516 to sense the fluid pressure of the gastric band 510 in the inner expandable ring 514. An antenna 724, a control 726, a battery 728, and memory 729 are provided with functionality similar to that of like components in system 500.

The system 700 differs from the system 500 in the configuration of the pump assembly 730 provided as part of the internal band adjustment system in housing 720. As shown, the pump assembly 730 includes a bleed valve 732 connected to the fill/drain lines 516, 517 that is operated similarly to valve 532 by operation of the pump 734 and reservoir 736 and control 726. However, the pump assembly 730 differs from pump assembly 530 with replacement of a single pump 540 with a plurality of pumps 740, 742, 744 (e.g., three 7-psi Bartel actuator pumps or other pump useful for this function/purpose) that are arranged in series between check valves 746, 748. The pumps 740, 742, 744 are operated via battery 728 and control 726 to pump fluid from the outer ring reservoir 512 into inner expandable ring 514 when the sensor 722 detects a pressure lower than a preset lower pressure limit. Further, in some embodiments, the check valves 746, 748 are opened by control 726 and powered by battery 728 to allow fluid in inner expandable ring that is under a pressure above a present upper pressure limit (as detected by sensor 722) to flow out of the inner expandable ring 514 through the pumps 740, 742, 744 into the outer ring reservoir 512 until determined by sensor 722 and control 726 to be within the preset operating range.

Figure 8:
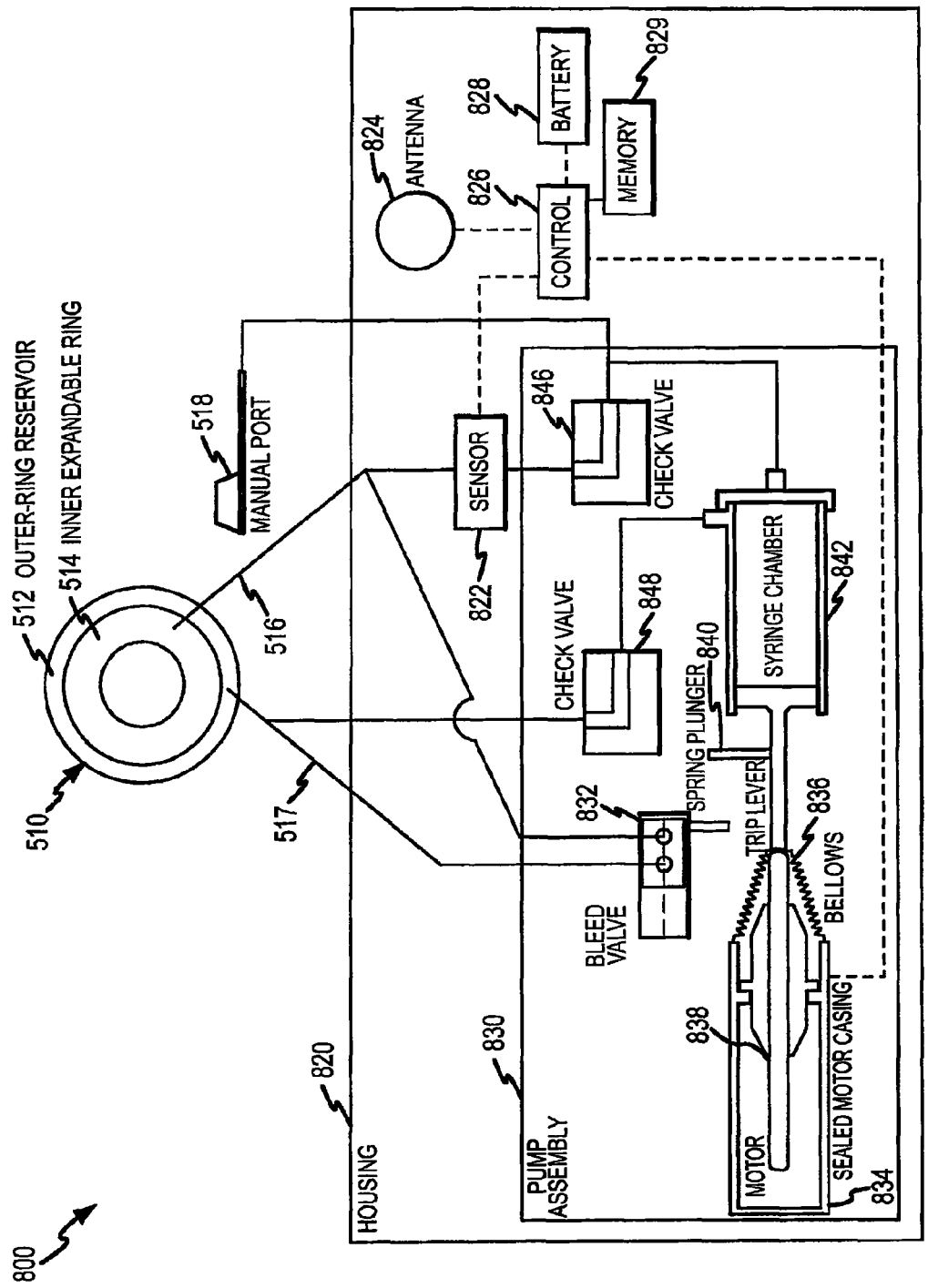
FIG. 8 is a schematic diagram similar to FIGS. 5 and 7 showing yet another embodiment of a self-regulating gastric band system of the invention using a pump assembly that differs from those shown in the systems of FIGS. 5 and 7.

FIG. 8 illustrates an embodiment of a self-regulating gastric band system 800 is similar to systems 500 and 700 including an expandable gastric band 510 with a self-contained fluid reservoir 512 and within housing 820 a pressure sensor 822, a communication module 824, a controller 826, a local power supply 828, and memory 829. The system 800 however includes a pump assembly 830 in the housing 820 that differs from the pump assemblies 530, 730. As shown, an optional bleed valve 832 is provided between the outer ring reservoir and the inner expandable ring 514 that is operable to maintain a desired pressure differential between the fluid in these two portions of the band 510 (or system 800). For example, it may be desirable in some bands 510 to maintain a differential of less than about 2 psi or less than about 0.25 to 1 psi or the like. In other embodiments (not shown) of system 800, the bleed valve 832 may be omitted.

To allow for selective adjustment of the size of the inner expandable ring 514, the pump assembly 830 includes a pair of check valves 846, 848 connected to the fill/drain lines 516, 517. Pumping or fluid motive forces are provided by a syringe or other chamber 842 that is in fluid communication with the two check valves 516, 517 and therefore, with the two reservoirs or portions 512, 514 of the band 510. Fluid is drawn into and forced out of the chamber 842 by operation of a squiggle motor 838 that is sealed in a motor casing 834 having a bellows 836 to support movement of a shaft/plunger 840 connected to the motor 838 (e.g., a Squiggle motor or the like) and chamber 842.

During operation of the system 800, the sensor 822 senses pressure in the inner expandable ring 514 of the band 510. The sensed or monitored band property is either used by the sensor 822 to determine if the band pressure is within a programmed or preset operating range or such a determination is made by control 826. Once a determination is made that the pressure is lower than a preset lower limit or out of range low, the control 826 operates the motor 838 to pump fluid from the outer ring reservoir 512 into the inner expandable ring 514 via check valves 846, 848 and fill/drain lines 516, 517 until the pressure in the band 510 as sensed by sensor 822 is within the preset operating range (or typically some amount higher than the lower limit). When a determination is made that the pressure of fluid in the inner expandable ring 514 is higher than a preset upper limit or out of range high, the control 826 may adjust the pressure (and corresponding size of the ring 514) by opening check valves 846 and 848 to allow fluid at a higher pressure in the inner expandable ring 514 to flow to the outer ring reservoir 512 via fill/drain lines 516, 517 until the pressure detected by the sensor 822 is again within the range (or at a pressure a preset amount below the upper pressure limit).

Figure 9:
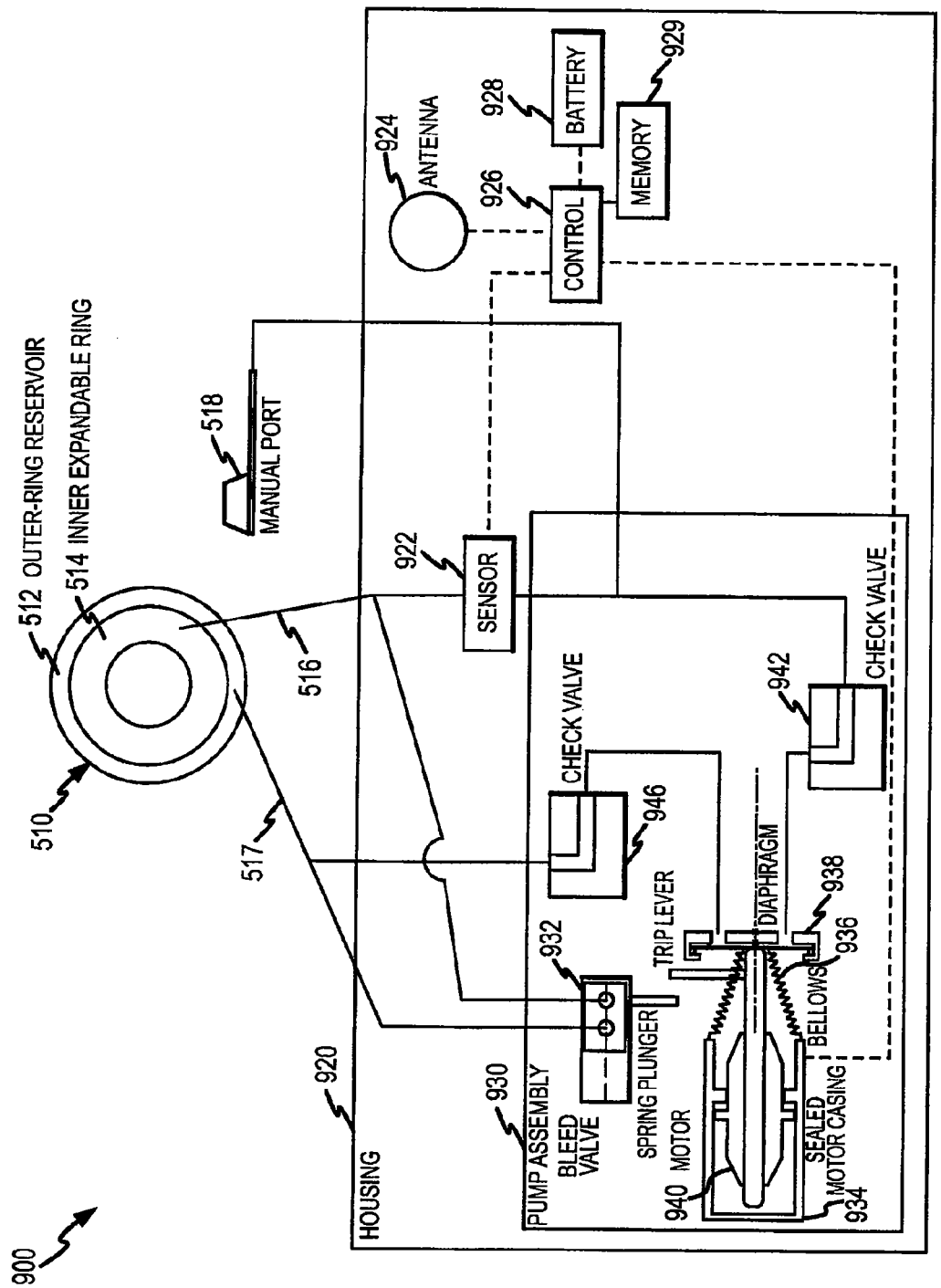
FIG. 9 is a schematic diagram similar to FIGS. 5, 7, and 8 that illustrates another embodiment of a self-regulating gastric band system of the invention using yet another pump assembly useful for practicing the adjusting features of the invention.

FIG. 9 illustrates another self-regulating gastric band system 900 similar to the systems 500, 700, and 800 in that it includes a gastric band 510 and a housing 920 that encloses a pressure sensor 922 in the fill line 516 of the band 510, an antenna or communication element 924, a control device 926, a battery 928, and memory 929. The pump assembly 930 is similar to assembly 830 in that it includes a bleed valve 932 in fluid communication with the inner expandable ring 514 and outer ring reservoir 512 via lines 516, 517 for maintaining a desired pressure differential between the two lumens or reservoirs 512, 514. The pump assembly 930 differs from assembly 830 in with the insertion between check valves 942, 946 of a pumping mechanism that is made up of a motor casing 934 sealing a squiggle motor 940 that is used to drive or move a diaphragm 938 via a shaft extending through or into bellows 936. Other operations of the system 900 are similar to that of system 800.

Figure 10:
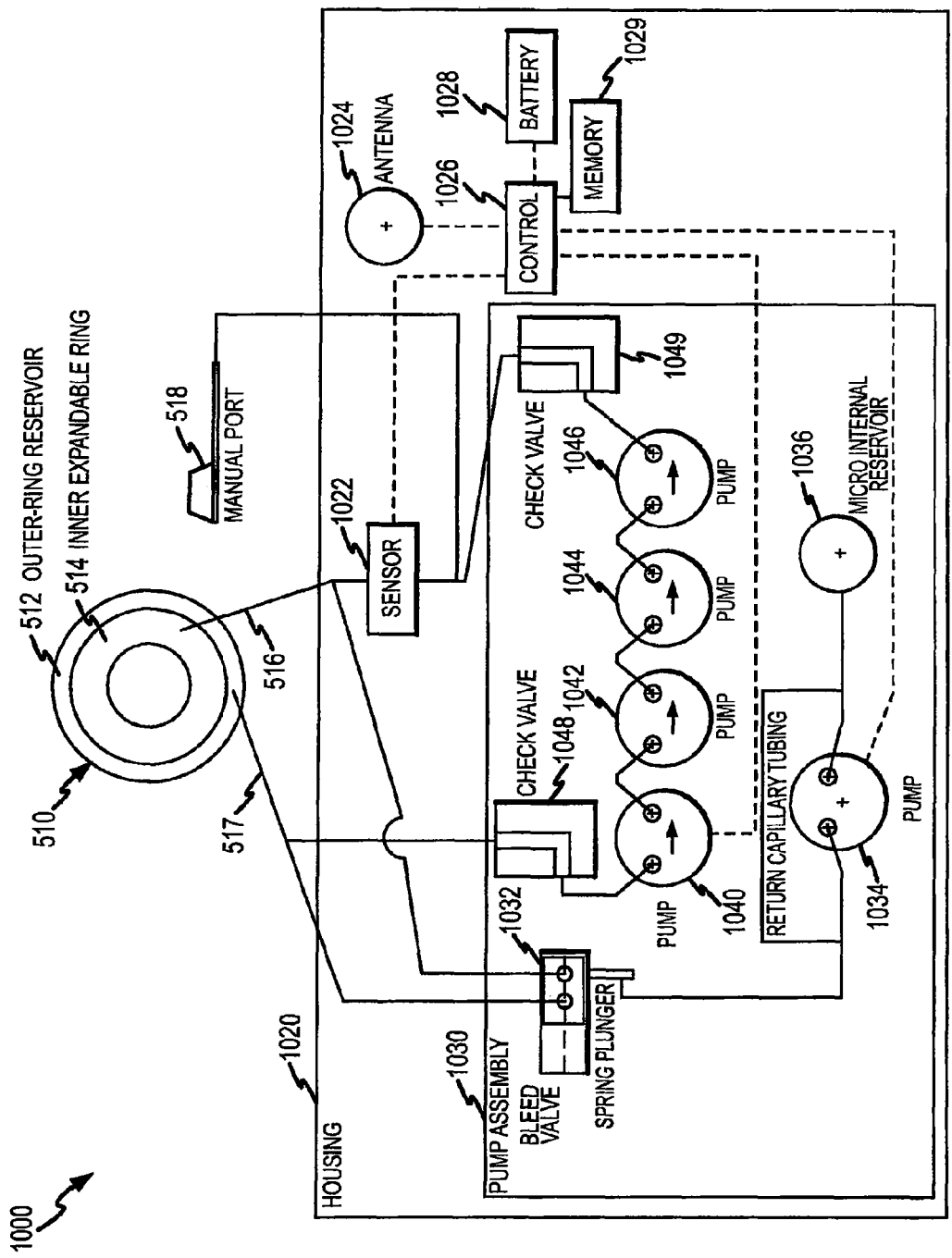
FIG. 10 is a schematic diagram similar to FIGS. 5, 7, 8, and 9 that shows still another embodiment of a self-regulating gastric band system of the invention using a pump assembly and sensor location relative to the systems of FIGS. 5, 7, 8, and 9.

FIG. 10 illustrates a self-regulating gastric band assembly 1000 that is configured similar to system 500 of FIG. 5. Differences between the systems (or unique aspects of system 1000) include the positioning of the sensor 1022 external to the housing 1020 between the inner expandable ring 514 and a check valve 1049 in the fill line 516. The sensor 1022 is in communication (wired or wireless) with the controller 1026, which acts to communicate with an external monitoring/control device (not shown in FIG. 10) via antenna or communication element 1024, to store data received from sensor 1022 and external monitoring/control device in memory 1029, and to power the pump assembly 1030 (as needed) with battery 1028, which also powers the controller 1026. The controller 1026 is also configured to operate (as discussed in detail above) the pump assembly 1030 to automatically maintain the band 510 within a desired operating range typically defined by a lower and an upper limit (e.g., a lower pressure limit and an upper pressure limit) by pumping fluid into and out of the inner expandable ring 514 based on band properties sensed by sensor 1022 (e.g., pressure of fluid in line 516 and in ring 514).

The system 1000 also differs from system 500 in the configuration of its pump assembly 1030. The pump assembly 1030 includes a bleed valve 1032 for bleeding higher pressure fluid in the inner expandable ring 514 (when sensed by the sensor and based on control signals from the control 1026) to the outer ring reservoir 512. The assembly 1030 however includes a different pump 1034, e.g., a 5-psi Thinxxs pump or the like, than that used in the system 530, which is primed by internal reservoir 1036 to operate the bleed valve 1032 in response to signals from the control 1026. The system 1000 further differs from system 500 in that a plurality of pumps 1040, 1042, 1044, 1046 (e.g., 5-psi Thinxxs pumps or other useful pumps) are positioned between check valves 1048, 1049 and the reservoir 512 and inner expandable ring 514 rather than a single pump 540. These serially-arranged pumps 1040, 1042, 1044, 1046 are operated to pump fluid from the reservoir 512 into the inner expandable ring 514 when the senor 1022 detects a pressure below (or outside low) a minimum pressure defining a lower bound of the desired operating range or the programmed pressure range for the band 510.

As can be seen from FIG. 5-10, there are many different pump assembly configurations that may be used to implement the present invention. Additionally, other components may be varied to achieve the desired functionality of a self-regulating gastric band. For example, the systems shown in FIGS. 5-10 included a fluid reservoir provided in a lumen or integral portion of the gastric band. In some embodiments, it may be desirable to have the fluid reservoir be provided within the pump housing. In other cases, the fluid reservoir may be provided as a component external to the pump housing and external to the gastric band, such as by providing a separate elastic sack, balloon, or other similar structure that would be useful for storing fluid for pumping into the band and out of the band by the pump assembly.

In some embodiments, it is desirable to allow adjustment of an implanted band by a physician or other technician via a telephone link. Briefly, this is achieved by providing a controller local to the patient and a remote controller local to the physician or technician, with the two controllers communicating via a wired and/or wireless telephone link. The local controller can be thought of as a remotely adjustable band (RAB) handheld controller (or the controller can be fixed but local to the patient) or RHC. The primary function of the RHC is to: locate the implanted pump, control the implanted pump, provide an easy to use programming and system status display, allow access to the RHC functions through remote dialup, provide a web server application which allows for web page-based control of all functions when accessed through remote dial up, and provide a standard wireless link to a cradle, which provides charging power to the controller and a telephony link (for accessing the web page and/or other controller). The local controller or RHC may, for example, be used to communicate via the antennae of the systems shown in FIGS. 1-10, and the use of such an RHC is explained in more detail in the following description.

Figure 11:
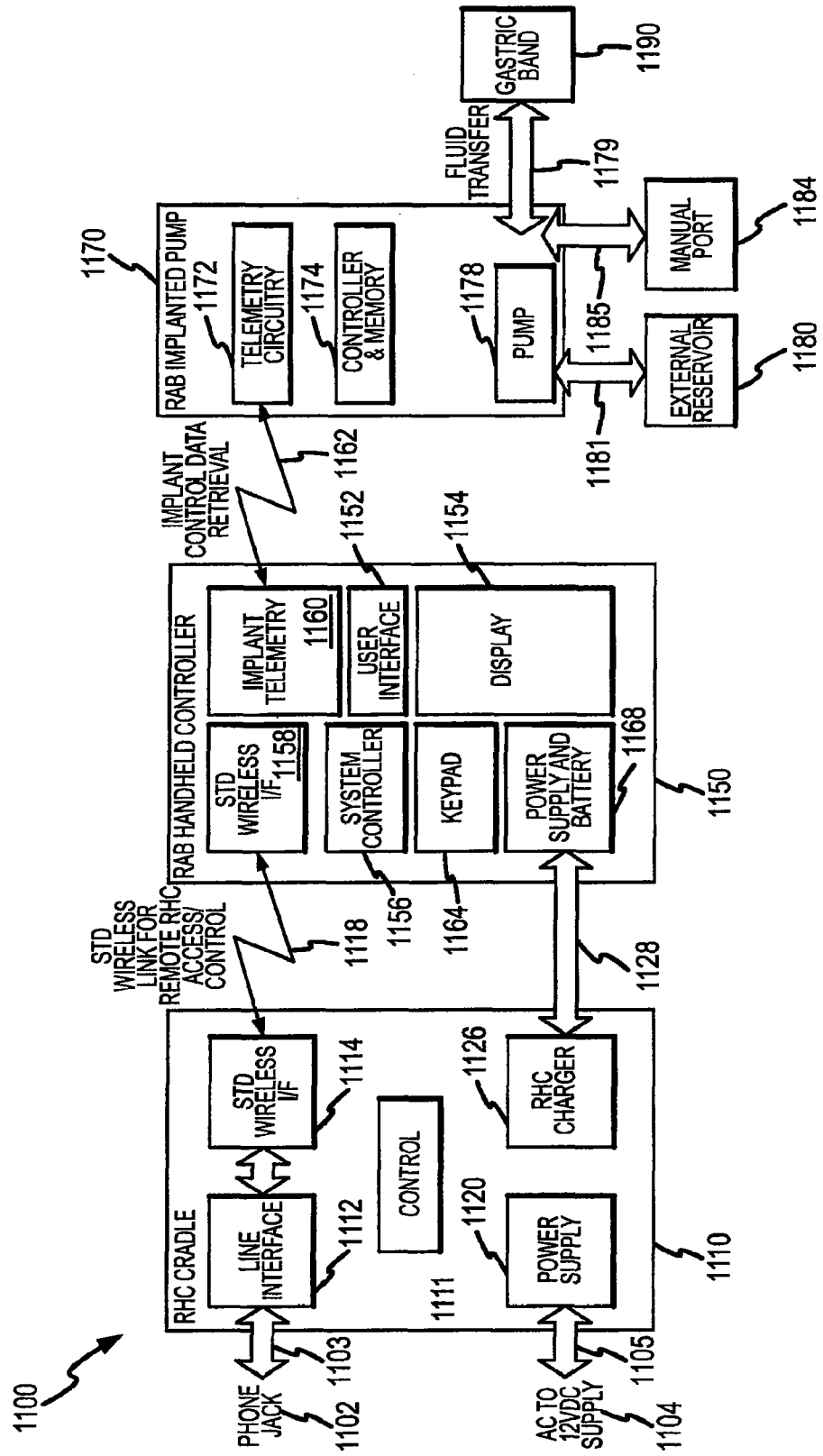
FIG. 11 is a functional block diagram of self-regulating or adjusting gastric band system of the invention utilizing a handheld controller communicating with remote controllers or services (such as web page-based controllers or services) via a telephone link.
Figure 12:
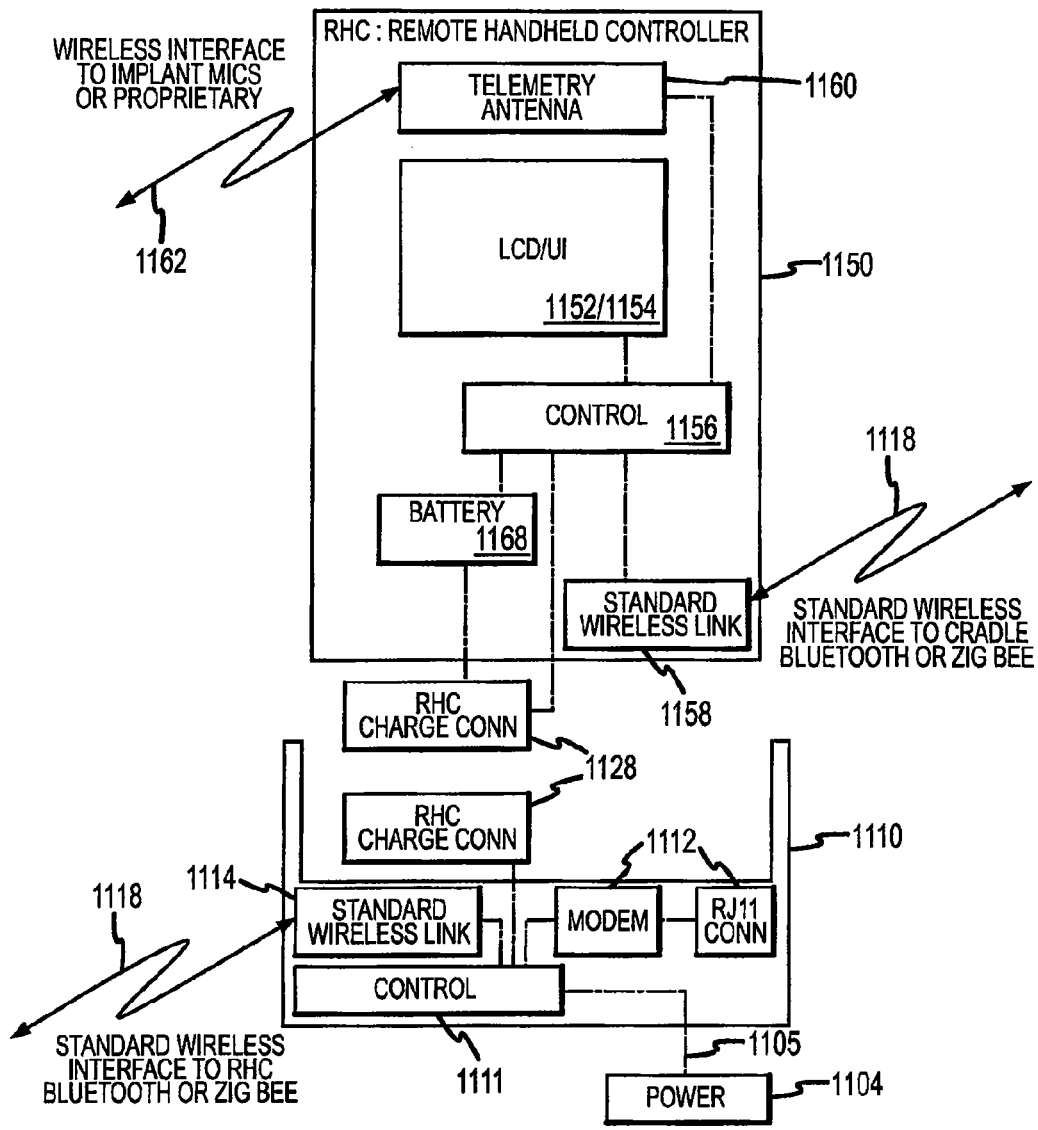
FIG. 12 is another functional block diagram showing the handheld controller and cradle of the system of FIG. 11 in additional detail.

FIG. 11 illustrates in functional block form a gastric band system 1100 that uses a RAB controller 1150 to control adjustments of an implanted (or implantable) band 1190. FIG. 12 illustrates RAB controller 1150 and its cradle 1110 in more detail. As shown, the system 1100 includes a cradle 1100 for providing telephony connections and power for a RAB handheld controller or RHC 1150. The RHC 1150 in turn is used to control via transferred data over wireless link 1162 an implanted pump 1170, which adjusts or regulates the size of a gastric band 1190 by controlling fluid transfer over connection 1179. Fluid is supplied in this example by external reservoir 1180 (e.g., external to a housing of the pump assembly 1170 or via a manual port 1184 (e.g., for an initial filling or sizing of the ban 1190) via connections 1181, 1185. As with previously described pump assemblies, the pump assembly 1170 includes telemetry circuitry 1172, controller and memory 1174 and one or more hydraulic pumps 1178.

The RHC 1150 is shown to include a user interface 1152 and display 1154 along with a keypad (or user input mechanism) 1164 to allow a user (such as gastric band patient or other operator of the system 1100) to view data from the pump assembly 1170 and data received remotely via the telephone link 1118 and to allow the user to make adjustments and enter data in some cases. The RHC 1150 further includes a system controller 1156, a wireless circuitry and antenna or cradle link 1158 for communicating with the cradle 1110, an implant telemetry 1160 for communicating with the telemetry circuitry 1172 of the implanted pump assembly 1170, and a power supply/battery 1168 to allow the RHC 1150 to be used outside the cradle 1110.

The cradle 1110 provides a power link 1128 by providing a power link 115 to a power supply 1104 via power supply 1120 and RHC charger 1126. More significantly, the cradle 1110 includes a controller 1111 and a telephone/data link 1118 to facilitate remote control of the RHC 1150 and pump assembly 1170 via a telephone jack or other connection 110 that is linked 1103 with a line interface 1112 to communicate with the RHC 1150 via wireless communication circuit/antenna 1114. The primary functions of the RHC cradle 1110 are to: charge the RHC battery 1168, store the RHC 1150 when not in use, provide telephone/line interface including a modem (in some cases as shown in FIG. 12) for data access via interface 1112, implement a standard wireless data link 1118 between the modem and RHC 1150 to allow remote access to the RHC features and pump assembly 1170, and allow access to the RHO functions through remote dialup.

Figure 13:
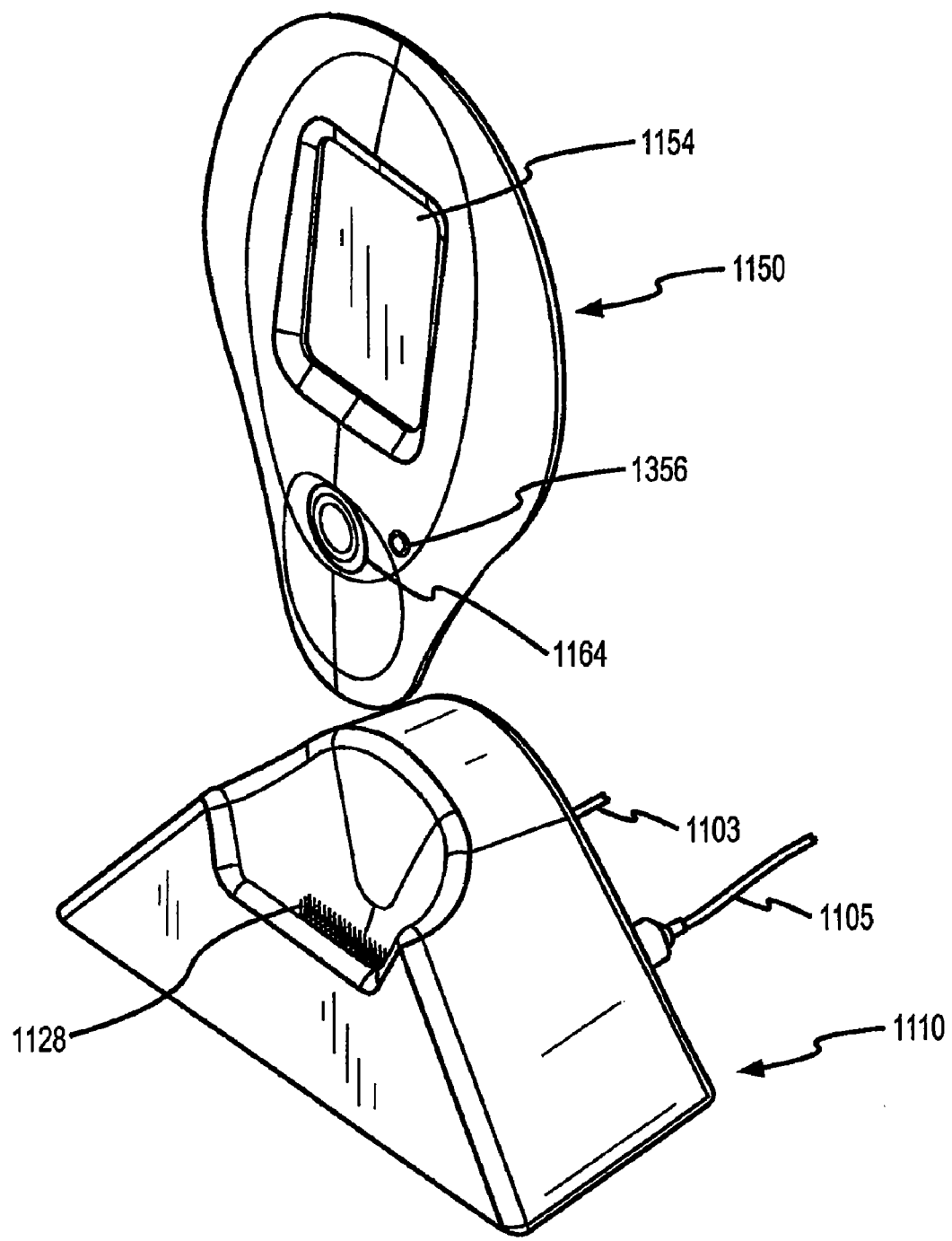
FIGS. 13 and 14 are perspective views of an exemplary implementation of a handheld controller and cradle according to the present invention, such as to implement the systems of FIGS. 10 and 11.
Figure 14:
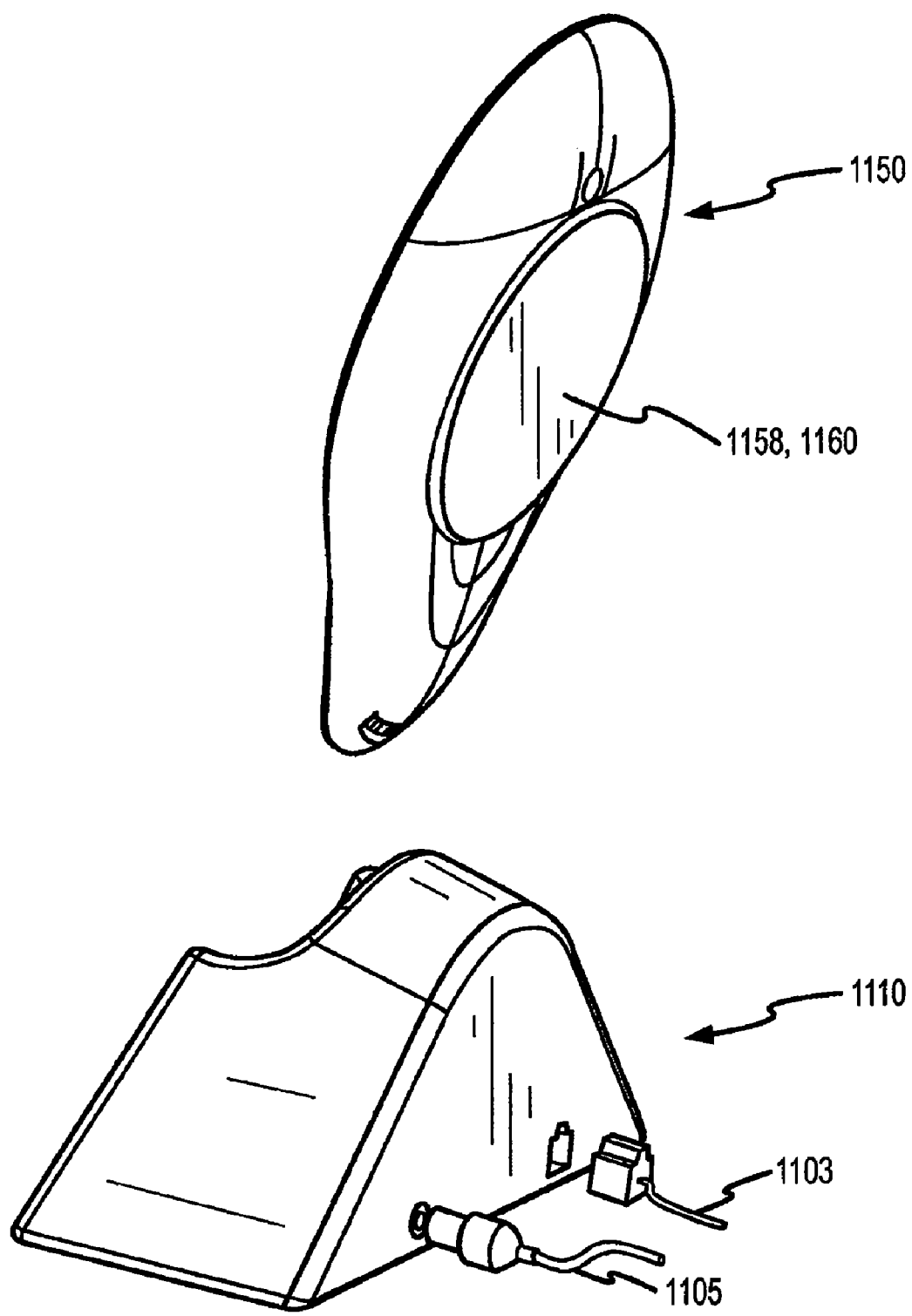

FIGS. 13 and 14 illustrate one useful physical implementation of the RHC 1150 and the cradle 1110. These figures show that the RHC 1150 can easily be removed and inserted or docked into the cradle for charging via power connection (or docking connector) 1128. A telephone line 1103 is connected to (or connectable to) cradle 1110 as is a power line 1105 (such as a 12 volt direct current line). The display 1154 upon which a user interface 1152 would be provided is shown in the RHC 1150 as is a keypad 1164 and a power on/off switch or button 1356. The RHC 1150 may be configured in a number of ways to include the implant telemetry access antenna and standard wireless antenna 1156, 1160 with these shown in FIG. 14 to be provided on the rear of the body or housing of the RHC 1150 for ease of access and maintenance. As can be seen, the RHC 1150 is configured for easy handheld operation to allow a user to place the RHC 1150 near the patient and the gastric band 1190 to facilitate communications with implant telemetry circuitry 1172 in the pump assembly 1170 and ease of data input/output via display 1154.

Figure 15:
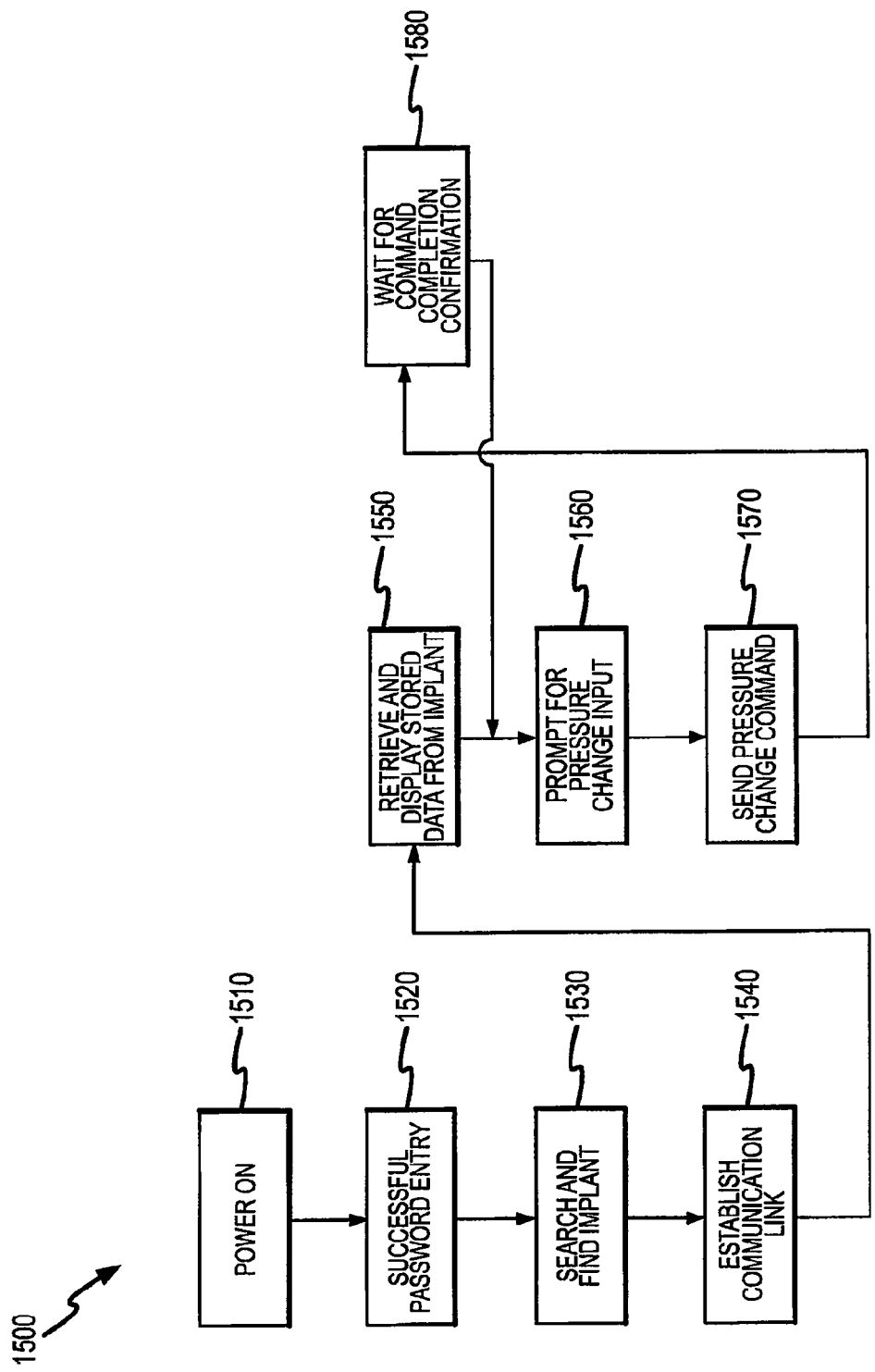
FIG. 15 is a flow chart of a normal mode of operating gastric band system, such as those described in FIGS. 10 and 11, to regulate the size of an implantable gastric band.

It may now be useful to discuss a few of the operational features of the system 1100 and RHC 1150 along with a discussion of its operations, with reference to FIG. 15, to regulate an implanted gastric band 1190. The useful features of the system 1110 and the RHC 1150 include: (a) the implantable pump 1170 that the RHC 1150 controls is self-powered and does not require power to be transferred by the controller 1150; (b) the implantable pump 1170 performs adjustments to the band 1190 until a desired band pressure is achieved (as opposed to a desired volume); (c) the RHC 1150 contains a standard wireless interface 1158, such as Bluetooth or ZIGBEE, connecting the RHC 1150 to the telephony interface 1114 in the RAB cradle 1110 which in turn connects via interface 1112 and connection 1103 to a remote computer or controller (not shown) capable of performing a dial-up access or otherwise communicating data and control information to the RHC 1150; (d) the RHC 1150 contains networking software run by controller 1156 allowing connectivity from remote computers through the telephone interface provided by cradle 1110 and wireless interface 1158; (e) the RHC 1150 contains a web server run by system controller 1156 allowing web-based access to all RHC 1150 functions, including adjustment commands, after a dial up networking connection has been established over the telephone interface, which eliminates the need for installing application specific software on accessing computer (e.g., in one embodiment, Secure Internet Explorer or a similar connection is the utilized).

The RHC 1150 operates in the following high level modes: normal, remote accessed, docked, and powered down. FIG. 15 illustrates operation of the RHC 1150 (or gastric band system 1100) in the normal mode for remotely adjusting or regulating 1500 a gastric band in a patient. In this mode the RHC's primary function is to access and control the RAB implantable pump 1170. Wireless access to the implantable pump 1170 may be, for example, through the Medical Implant Communications Service (MICS) band operating in the 402-405 MHz frequency range. The communication protocol between the RHC 1150 and implantable pump 1170 may be kept compliant with patient privacy regulations and health industry regulations. The flow chart of FIG. 15 shows a typical set of activities leading to an adjustment. Adjustments are typically in the form of pressure changes in the band as opposed to discrete volumetric change.

In the normal regulation mode or process 1500, the RHC 1550 is powered on at 1510, such as by pressing a button or moving a switch 1356 on the RHC 1550. At 1520, a password entry may be required to use the RHC 1550 to prevent unauthorized users from adjusting the band 1190. At 1530, the RHC 1550 is operated by the system controller 1156 to search and find the implanted pump 1170 such as communications being performed between the implant telemetry 1160 in the RHC 1150 and the telemetry circuitry 1172 of the pump assembly 1170 with the link 1162 being established at 1540 when the assembly 1170 is found by the RHC 1150. At 1550, the RHC 1550 acts to retrieve and display data that is stored in the memory 1174 of the implanted pump assembly 1170.

At 1560, the RHC 1550 prompts via UI 1152 and display 1154 for a pressure change input (i.e., does the user wish to change or adjust the pressure in the gastric band 1190 to adjust the band 1190). At 1570, input has been received (such as via input by the user via keypad 1164 and/or UI 1152) and a pressure change command(s) is sent via link 1162 from the RHC 1150 to the implanted pump assembly 1170. At 1580, the RHC 1550 waits for a confirmation from the implanted pump assembly 1170 that it has completed the pressure change in the gastric band 1190 (e.g., via operation of the pump 1178 by the controller 1174 to add or remove fluid via connections 1179, 1181 and fluid reservoir 1180 as discussed in detail with reference to FIGS. 1-10). The process 1500 may then continue with retrieval of additional data at 1550 or more typically, with displaying a confirmation and then prompting for input of additional changes at 1560.

An innovative feature of the system 1100 (and the systems of FIGS. 1-10) is the capability for a physician to perform remote band adjustment. By operating the system 1100, physicians or other operators are able to connect securely from their office computers to the RHC 1150. This connection and control communications are achieved by operating the physician's or other operator's computer to "dial-up" and connect to the RAB system 1100 through a telephone modem or link in the cradle 1110.

The following sequence of events occur in one embodiment to achieve remote access to and control of the RAB system: (a) the patient connects the cradle 1110 to an active telephone jack 1102 using a standard telephone cord 1103, with the physician typically being made aware of the phone number of the cradle/jack prior to attempting the remote access; (b) the physician uses standard windows dial-up networking software to dial the RAB system 1100; (c) the cradle 1110 contains the telephone interface and modem circuitry 1112, and upon detection of a telephone ring signal on the telephone line 1103, the cradle 1110 automatically "picks up" and the modem 1112 is activated; (d) the modem 1112 in the cradle 1110 establishes a connection 1103 with the physician's computer modem (not shown); (e) the cradle 1110 then establishes a wireless data link 1118 between the modem or interface 1114 and the RAB Handheld Controller 1150, which contains networking software (e.g., a TCP/IP stack run by system controller 1156 and/or with wireless interface 1158); (f) the RHC 1150 establishes a network connection with the physician's computer, with the connection typically being encrypted and compatible with Microsoft Internet Explorer secure connection or the like; (g) the physician launches the Microsoft Internet Explorer or similar application on their computer or other remote controller and, using a predefined web address, gains access to a web based application on the RHC 1150 allowing full control of the RHC's function; (h) the physician performs all functions allowed in the normal mode of operation (e.g., method 1500 of FIG. 15) after entering the appropriate access codes (Username and/or password); and (i) the patient or operator of the RHC 1150 will be prompted on the RHC screen or display 1154 on what action they should take to facilitate remote adjustment/control of implanted pump assembly 1170 by the physician. In many cases, the wireless data link will be either Bluetooth, ZIGBEE, or other communication protocol/technique compliant.

The docked mode of operation is primarily used for charging the RHC 1150. However, remote access may be provided for the purpose of preprogramming an adjustment or retrieving patient data. In the powered down mode of operation, the RHC functions are suspended except for battery charging and charge monitoring.

The operation of a self-regulating gastric band system has been described in detail with reference to FIGS. 1-15, but it may be useful to provide yet another summary of an embodiment of such a system. An implantable pump assembly is provided that allows for a non-invasive pressure management of an implantable gastric band, and this function is typically invoked as a response to commands transmitted from the RAB Handheld Controller (RHC) shown in FIGS. 11-15 or other controller. The implanted pump assembly and its components are internally powered (i.e., powered locally by a battery or the like rather than remotely or external to the patient's body).

The implanted components (or internal band adjustment system) include the following functional components: an enclosure; an external reservoir; a manual port; a fluid pump (e.g., a Bartels 20 PSI pump with active valve or the like); a control circuitry (e.g., for controlling the pump and any valves); telemetry circuitry and antenna; and a battery and power supply circuitry. The RAB implantable pump can be implemented as a piezoelectric 20 PSI (or other capacity) pump, e.g., a pump with an active valve incorporated into its design. The implantable pump is preferably self-powered through a custom implantable battery designed for long term implantation. The pump has inlet and outlet valves. For a robust design, check valves at the pump inlet and the pump outlet are used to eliminate or control leakage, such as micro check valves. For pressure release and pressure equalization, the system may use a piezoelectric or active valve or the like. The system directly pumps fluid from the reservoir to the band, changing the band pressure. Band pressure release is accomplished through a separate sub-system. Increase in pressure in the band is done directly via the pump. Decrease in pressure is achieved through pressure release followed by re-pumping the band to the proper pressure.

The following describes the two modes of band adjustment. In normal operation, a 20-psi pump with 30-psi minimum back pressure withstanding check valve maintains directional flow between an external reservoir and the gastric band. The pump, e.g., a 20-psi piezoelectric pump or the like, is for pressure increase in the band and is monitored by a pressure sensor. Because of the nature of the piezo material, the flow is not reversible for pressure relief in the band. Pressure is maintained in the band once the pump is shut down. No leakage or back-flow occurs because of check valves that are integrated into the pump or provided separately.

To provide pressure relief/equalization, for pressure relief in the band, an active valve/flow re-direction mechanism, e.g., a piezo-active valve, is used. The active valve is opened to equalize pressure between the band and the reservoir. Once equalization is achieved, the active valve is shut down. The main pump is then activated to increase the pressure to the desired pressure in the gastric band.

As discussed above, it is sometimes desirable to monitor the pressure of fluid within an implanted gastric band. Further, in some embodiments, it is desirable for the pressure of the band or the fluid in the band to be automatically monitored and controlled/adjusted by an internal band adjustment system. This automatic adjusting may be combined with periodic reporting of pressure readings and settings to an external control device and, in some cases, with changes of pressure settings being provided by the external control device. In other cases, it may be useful to monitor pressure in the band, such as via a sensor at an access port, and to control filling of the gastric band based on analysis and/or monitoring of the band pressure during such filling operations. These pressure-based embodiments of the invention are explained in more detail below with reference to FIGS. 16-18, and the aspects discussed below may be used alone or in combination with any of the foregoing embodiments of the invention. The following embodiments of the invention also provide further detail on the use of one or more software applications, e.g., pressure analysis and adjusting software or modules, to facilitate automated pressure control for a gastric band or to facilitate more accurate and/or effective filling and adjustment of bands via an access port and operation of an external fill device.

Figure 16:
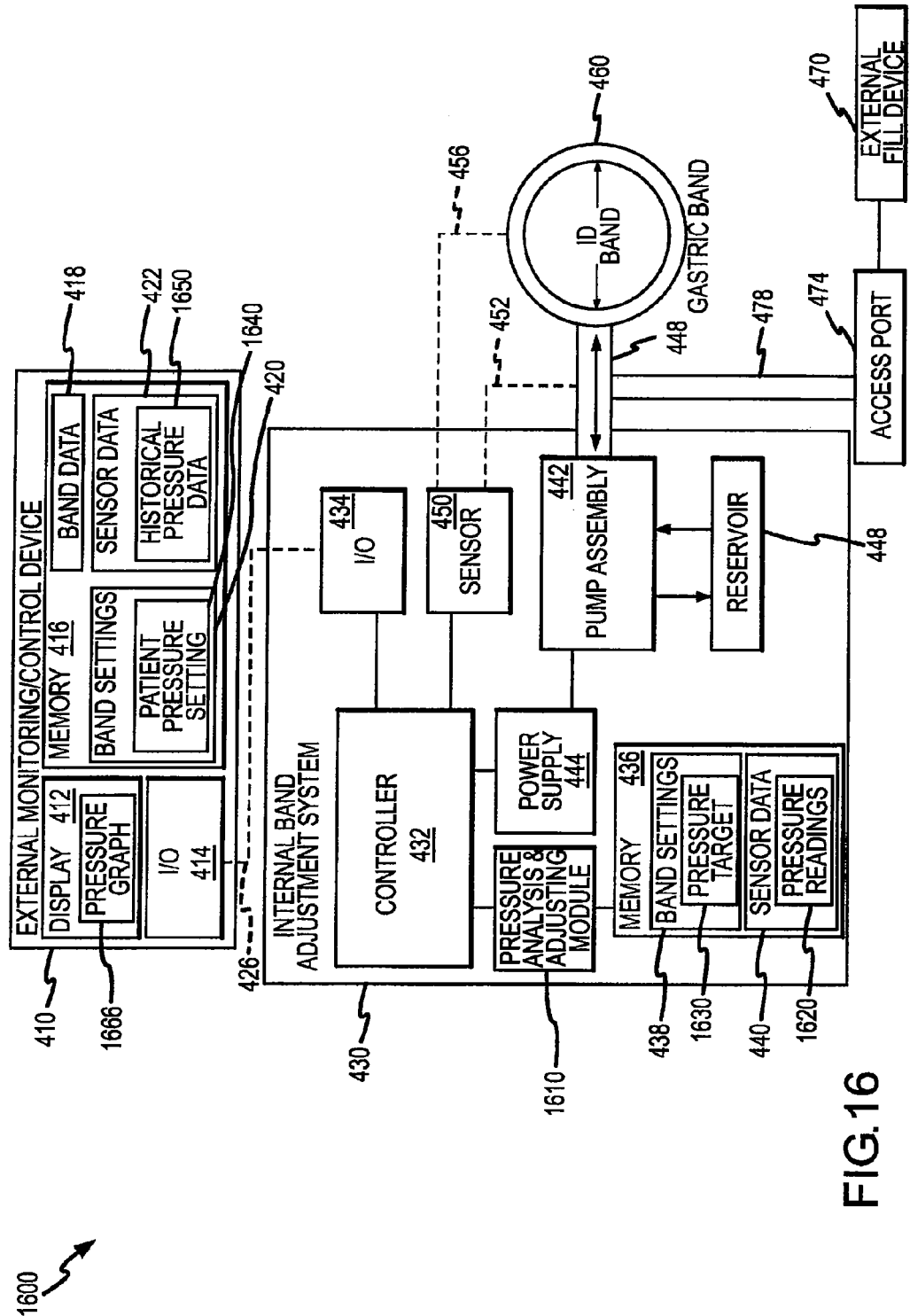
FIG. 16 is a functional block diagram of a self-regulating gastric band system similar to that of FIG. 4 according to another embodiment of the invention showing the use of a software application or module to provide automated (or optional manually instigated) control of band pressure.

For example, another embodiment of a self-regulating gastric band assembly or system 1600 is shown in FIG. 16. The system 1600 is shown to be a modification of system 400 of FIG. 4, with like numbered components not being explained in detail here. Of course, these modifications could be made to any of the self-regulating systems/devices described herein (such as those shown in FIGS. 5-12). The system 1600 is particularly adapted for self-adjusting a gastric band 460 based on a sensed pressure of the fluid in the band 460 (e.g., in the expandable portion of the band). To this end, the sensor 450 of the internal band adjustment system 430 is provided in fluid communication with the band fluid such as by connection to or placement in the band 460, in line 448 or at/in pump assembly 442, in line 478, or in access port 474. The sensor 450 is used to sense or take readings of the pressure of fluid in the band 460 and controller 432 acts to store the pressure readings 1620 in the memory 436 (e.g., as part of the stored sensor data 440). In the memory 436, one or more pressure targets 1630 (e.g., pressure values or levels) may also be stored as part of the band settings 438, and the controller 432 functions to adjust the volume of the fluid in the band 460 via reservoir 448 and pump assembly 442 to maintain this target pressure 1630 (or to maintain fluid or band pressure within a range encompassing the target pressure 1630 to allow for some variance as discussed above). The pressure readings 1620 are communicated to an external monitoring/control device 410 wirelessly 426 via I/O devices 434, 414. The data is stored as historical pressure data 1650 in the memory 416 of the external device 410. The patient pressure setting 1640 is stored in the memory 416 and is provided to or written to the memory 436 of the internal band adjustment system 430 for use in controlling the pressure in band 460. The sensed information 1650 may be reported to a user of the external device 410 by generating a pressure graph or report 1666 on display 412 (e.g., see the report or graphics 1800 of FIG. 18 as an example).

To allow ongoing self-adjusting of pressure, the internal band adjustment system 430 includes a pressure analysis and adjusting module 1610. This may be a software application (or combination of software and hardware) that is run by the controller 432 to process the pressure readings 1620 to determine if the pressure target 1630 is being maintained during ongoing operations. Significantly, though, the module 1610 can also be used to initially establish the pressure target or ideal pressure setting 1630 for a particular patient based on analysis of pressure readings 1620. Then, once set, the module 1610 may be used to adjust the pressure of the band 460 in an ongoing manner and/or in response to commands or queries from the external device 410. In some cases, the controller 432 may also operate to reduce pressure in the band 460 when there is an obstruction or other problem/event for a patient for which loosening of the band 460 temporarily is desirable.

Figure 18:
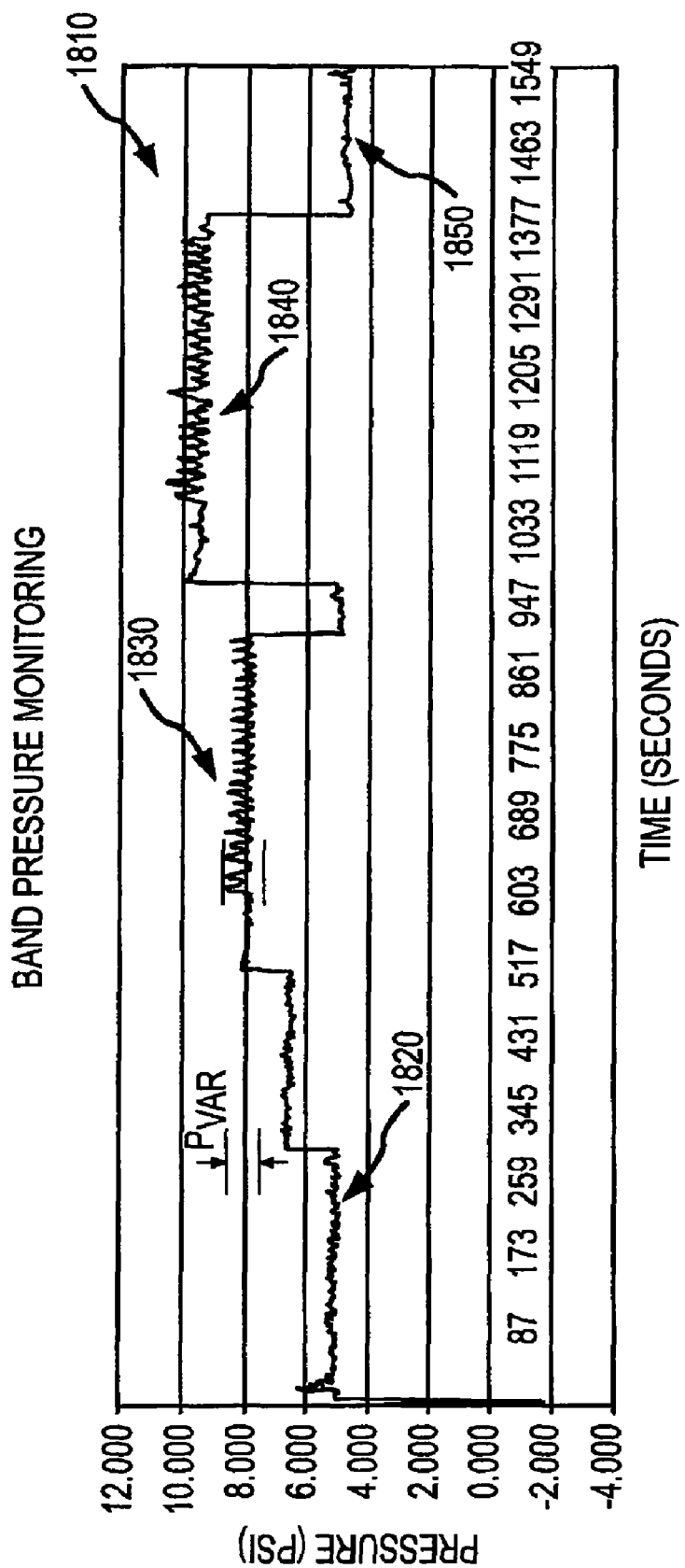
FIG. 18 illustrates a graph of gastric band pressure data, which may be historical or provided via a display in real time.

Operation of the system 1600 and use of the pressure analysis and adjustment module 1610 is now described in detail with reference to FIG. 16 and also FIG. 18. The pressure graph 1810 of FIG. 18 illustrates a graph of pressure over time for a gastric band, such as band 460, installed in a patient. Pressure data 1620 was collected from the sensor 450 over a period of time and over a number of band fill or use operations that included initial or nominal fill, a later adjustment or increase of fluid volume in the band, and a further adjustment to increase the fluid volume to an overfill point. The graph 1810 is useful for showing how pressure data 1620 can be analyzed by the pressure analysis and adjustment module 1610 to establish a pressure target 1630 and to identify when further adjustments may be desirable (e.g., when the pressure target 1630 should be adjusted up or down to suit changing operating parameters such as changes with regard to the patient and/or the band or associated equipment).

The graph 1810 is representative of a real-time pressure curve generated from pressure readings 1620 from an actual patient in which a band 460 has been implanted. Initially, the band 460 may be filled with a nominal amount of fluid to achieve a first or second pressure (e.g., about 5 to 7 PSI) as shown at 1820. This first portion of the curve 1810, i.e., from 0 to 517 seconds, corresponds to when the band 460 was at a fill volume that was inducing satiety in a patient or was slightly overfilled beyond that point. During experimentation, this fill point was determined initially by filling the band, such as with external fill device 470, and receiving feedback from the patient to identify the nominal fill to achieve such feelings of satiety. The inventor noted that there was very little variation in the pressure, $P_{VAR}$, as measured from the maximum and minimum read pressure values at a particular fill volume or by determining a standard deviation in the readings. This minor variation in pressure is shown in the two pressures steps from time 0 to 517 seconds.

In the second portion 1830 of the curve 1810, the band 460 was filled with additional fluid so as to increase the pressure, e.g., to an average or median pressure of about 8 PSI in this example. At this point of the experiment or study (i.e., from about 517 to about 900 seconds, the patient reported being or feeling overfilled and the patient was slightly uncomfortable. The pressure variations, $P_{VAR}$, (or standard deviation) in pressure readings increased significantly relative to variations seen in the satiated fill portion of the curve 1820. Further, when the band 460 is filled even further to an increasingly overfilled level of fluid as shown by curve 1840, the intraband pressure response increases in its variation as can be seen from about 1033 to 1377 seconds. Through this knowledge of an operating band 460, the inventor determined that the pressure analysis and adjustment module 1610 can be configured to determine a pressure target either with no input from an external device 410 or with an initial target being provided by the device 410.

In one embodiment, the pressure analysis and adjustment module 1610 functions to analyze sensed pressure of fluid in the band 460 (e.g., band pressure) and to establish a target pressure setting 1630 for the band 460 (or for the patient using the band 460). To provide this functionality, the internal band adjustment system 430 may operate to awaken or activate the sensor 450 to take pressure readings from of the fluid pressure in the band 460 (e.g., multiple readings per second or more or less readings). The external fill device 470 may be used to provide a conventional, nominal fill of the band 460. For example, it may be known that a volume of fluid can be added via access port 474 (such as with a needle) to not overfill the band but also that likely will not place the band 460 at an ideal or target operating pressure 1630 for any patient.

After (or during) this fill, the module 1610 may cause the controller 432 to collect pressure readings 1620 for a period of time (or to collect a set number of readings) with the sensor 450. These pressure readings may coincide with the initial step of the first portion 1820 of the pressure curve 1810, which in this example is about 5 PSI. The module 1610 operates to analyze the pressure variation (e.g., between a maximum and minimum) at this fill volume. This determined maximum (or average or median) pressure variation, PVAR, or a standard deviation may be stored in memory 436 and compared to a preset maximum acceptable pressure variation. If this preset maximum is not exceeded (which is likely at the initial nominal fill level), the module 1610 causes the controller 432 to operate the pump assembly 442 to pump fluid from reservoir 448 into the band 460 to increase the pressure to a next incremental setting that is higher than the nominal setting by a particular amount (e.g., by 0.5 PSI, 1 PSI, 2 PSI, or some other useful increment), such as from 5 PSI to about 7 PSI as shown in the example in FIG. 18. In some cases, the module 1610 may cause the controller 432 to add a preset volume to the band 460 to increment up or increase the pressure of the band 460 rather than adjusting to a preset pressure increase.

At this new fill level/volume or pressure, the sensor 450 is used to gather another set of pressure readings 1620. The module 1610 processes these readings to determine a pressure variation (or standard deviation for the readings) and compares this variation or deviation to a preset maximum. Again, if the maximum is not exceeded (i.e., the variation in pressure is relatively small), the module 1610 determines that the band 460 may not yet have reached its ideal pressure setting. This ideal or target pressure setting is, in this case, defined as one in which pressure readings are maximized but the pressure variations as measured by differences between maximum and minimum values (or as a standard deviation) do not exceed a threshold level while a fill volume is held steady or constant. In other embodiments, a pressure value below such a "maximum" pressure but above a pressure associated with the nominal or initial fill volume for the band 460 is utilized in operations. The target pressure 1630 may be similar across a population of patients, but it typically will vary enough due to manufacturing tolerances and differences among patients to make it desirable for the module 1610 to be operable to identify a setting 1630 for a particular patient after the band 460 is implanted.

If the pressure still does not vary significantly and does not exceed a preset maximum pressure variation (such as shown in the second step of curve portion 1820), the module 1610 stores the determined pressure variations in memory 436, such as in sensor data, and causes the controller 432 to again operate the pump assembly 442 to increase the pressure in the band 460 by pumping more fluid from the reservoir 448 to the band 460. The band adjustment may be continued until a pressure increment is reached or to add a preset increase in band fluid volume. For example, the pressures sensor 450 continues to gather pressure readings 1620 that are stored in memory 436. When the adjustment is completed (e.g., such as after an increase in pressure of 0.5, 1, 1.5, 2, or similar increase or from about 7 PSI to 8 PSI as shown in FIG. 18), the controller 432 halts operation of the pump assembly 442 and continues to collect readings 1620 from the sensor 450 (such as for a preset period of time or until a preset number of readings are obtained as defined by module 1610). The module 1610 then determines a pressure variation at this new band fill level and compares this determined variation to the preset acceptable variation for the band 460. If the determined variation does not exceed the maximum, another incremental change in fill for the band is initiated by the module 1610. Such as to the pressure level shown at curve portion 1840 of FIG. 18.

In contrast, the module 1610 may determine that at this new fill level that the band pressure has a pressure variation, P.sub.VAR, that is too large because it matches or exceeds the preset maximum value for the band 460. When such a determination is made, the module 1610 may act to cause the controller 432 to operate the pump or valve assembly 442 to reduce the amount of fluid in the band 460 by returning or pumping fluid back into the reservoir 448. For example, the module 1610 may instruct the controller 432 so as to return to the prior fill level (or prior band pressure) or to a fill level or volume (or associated band pressure) between the prior fill level and the present level such as to a midpoint between the two levels. Additional readings may be taken at this level and if the maximum acceptable pressure variation is not exceeded, the pressure associated with this fill level may be stored as the ideal or target pressure 1620 for the patient (or the fill level may be increased incrementally and the process repeated one or more times prior to setting the target pressure 1620 at a level where the maximum pressure variation setting is not exceeded). If the pressure variation is exceeded, the fill may be further reduced until the pressure readings show the variation setting is not exceeded. The module 1610 then can be used to monitor the pressure readings 1620 in a continuous or more periodic fashion and to operate the controller 432 as discussed above to maintain the pressure of the band 460 at the target setting 1630 or in a range that includes the setting 1630 (such as at the midpoint of the range).

In a typical embodiment, the pressure readings 1620 during this process of identifying the target pressure 1630 and otherwise are stored in memory 436. Similarly, the module 1610 may store the pressure variations (or standard deviations) determined at each band fill level as well as, in some embodiments, the volume of fluid added in each step. This data is then transferred via wireless communications 426 to the external monitoring/control device 410 for storage in memory 416, where it can readily be accessed for viewing and review such as by a doctor or other use of device 410. In some cases, the transferred pressure readings 1650 can be used by the control device 1610 in generating graphs 1810 as shown in FIG. 18. In place of pure historical data, the graph 1810 can be displayed on the device at 1666 as the data is being gathered by the internal band adjustment system 430 to provide real time feedback/information. The information in memory 416 may also be transferred to a personal computer or other computing device for storage and/or further analysis.

The system 1600 allows for real time pressure monitoring of the band 460. For example, the device 410 (a handheld or desktop device) typically includes software (not shown) to allow an operator to see actual pressure output from the sensor 450 in a pressure graph or display 1666 (e.g., a graph similar to curve 1810 of FIG. 18). The pressure display 1666 may include a pressure curve (e.g., curve 1810 or the like) and/or additional information such as average pressure, pressure standard deviation or variation, pressure minimum, and pressure maximum as measured over time. The curves in display 1666 are useful for allowing an operator such as physician to visualize the pressure changes within the band 460 while treating a patient or adjusting a band 460. For example, after a routine band adjustment where a physician adds fluid to a gastric band (such as via an external fill device 470), it is typical for a physician to ask the patient to swallow water and then ask how the patient feels to ensure their band is adjusted to an "optimum" fill amount or level. With a graph/curve 1666 in the display 412, the physician can not only listen to the patient verbal feedback but also match with measured pressures and pressure changes/variations after an adjustment to decide if additional adjustments may be useful or advisable.

The curves or changes in pressure are generally generated by peristalsis in the esophagus that is translated down to the stomach and the attached band 460. This can be thought of as a pressure column that is pushed down the stoma of the esophagus and through the stoma at the stomach/band interface. As described above, the software module 1610 acts to analyze pressure readings from a sensor in fluid communication with the band fluid so as to identify when these pressure changes or variations are within an acceptable range (e.g., are below a present maximum variation or standard deviation).

The preset maximum deviation that is used by the module 1610 may be set for a band in a number of ways. For example, the preset maximum pressure variation or standard deviation may be set for all bands in a consistent manner or be set for a particular implanted band. For example, the preset maximum may be determined by studying a group of patient to gather pressure data similar to that discussed relative to the curve 1810 of FIG. 18 and based on such a study an acceptable maximum variation may be set for a particular band design (such as 0.05 to 0.5 PSI and more typically less than about 0.15 PSI or less than 0.1 PSI). This preset may then be programmed into each system 430 for use by the module 1610 in determining the pressure target 1630 for the particular patient (e.g., provide a patient-specific target pressure for the band).

The study of implant patients may be performed in a number of ways to determine the preset maximum pressure variation or deviation but typically will involve some level of patient participation or feedback. In one embodiment, pressure data or readings were collected from conventional gastric bands for a number of patients at several fill levels or volumes. Specifically, pressure readings were obtained after "optimum" fill levels were set (or prior to adjustment to increase fluid volumes in the band), after an adjustment (or injection of additional fluid), and when the patient was swallowing water after completion of the adjustment. Patients were asked to participate in a study when they were not currently in need of an adjustment, i.e., a physician had previously set a band at a target fill level or fluid volume and its associated pressure. Pressure data was collected from the bands in these patients by inserting a needle into their access ports and connecting the needle fluid path to a pressure transducer or sensor. The transducer used in this particular experiment was capable of obtaining multiple pressure readings per second and the equipment connected to the transducer could store these readings and also graph the results in substantially real time (and it is believed similar equipment may be useful for systems 430 of the invention for the sensors 450). It was observed that when a patient's band was at the "optimal" or target setting provided by the physician the pressure readings only varied minimally as is shown in portion 1820 of curve 1810 of FIG. 18. For example, this minimal variation may be less than about 0.1 PSI. When the patient swallowed water gradual increases in pressure was noted but variations were still relatively small.

In contrast, when the volume of fluid in the band was increased to a point that the patient indicated they were noticeably uncomfortable, the average or median pressure not only stepped up to a higher value but the variations in pressure also increased (as can be seen in the curve portion 1830 of curve 1810). The relative intensity of these pressure curves were then correlated to the patients' comfort levels. When the patients' were noticeably uncomfortable, the pressure curves were found to vary significantly, e.g., up to 2 PSI or more. The greater the intensity of the waves or variations in pressure, the longer they tended to last. Data was recorded and observed for each patient at each fill level, e.g., 2 to 5 minute periods at each level at which pressure did not drop (beside detected pressure variations) unless fluid was removed from the band. It was determined in these tests that when the band was returned to a lower or "optimal" fill level (or band pressure associated with such fill volume), the pressure variation again became negligible (i.e., relatively low such as below about 0.1 to 0.2 PSI). This can be seen at portion 1850 of pressure curve 1810 shown in FIG. 18. These experiments provide data for setting a maximum allowable pressure variation (or standard deviation) that can be used with a gastric band (but, in some cases, such experiments would be preferably performed for each particular gastric band design as the acceptable variations may vary with such designs). Based on this data, a pressure analysis and adjustment module, such as module 1610, can be designed that follows a similar process to be followed with an individual patient to determine a pressure target for that patient with a particular gastric band (e.g., moving from a nominal fill volume to higher fill volumes and back again until a fill volume is identified for which the pressure variation remains below a preset maximum pressure variation setting). In other embodiments, the module (such as module 1610) is more complex and is able also to establish the maximum acceptable pressure variation through analysis of various fill levels and the variations identified at each level.

Figure 17:
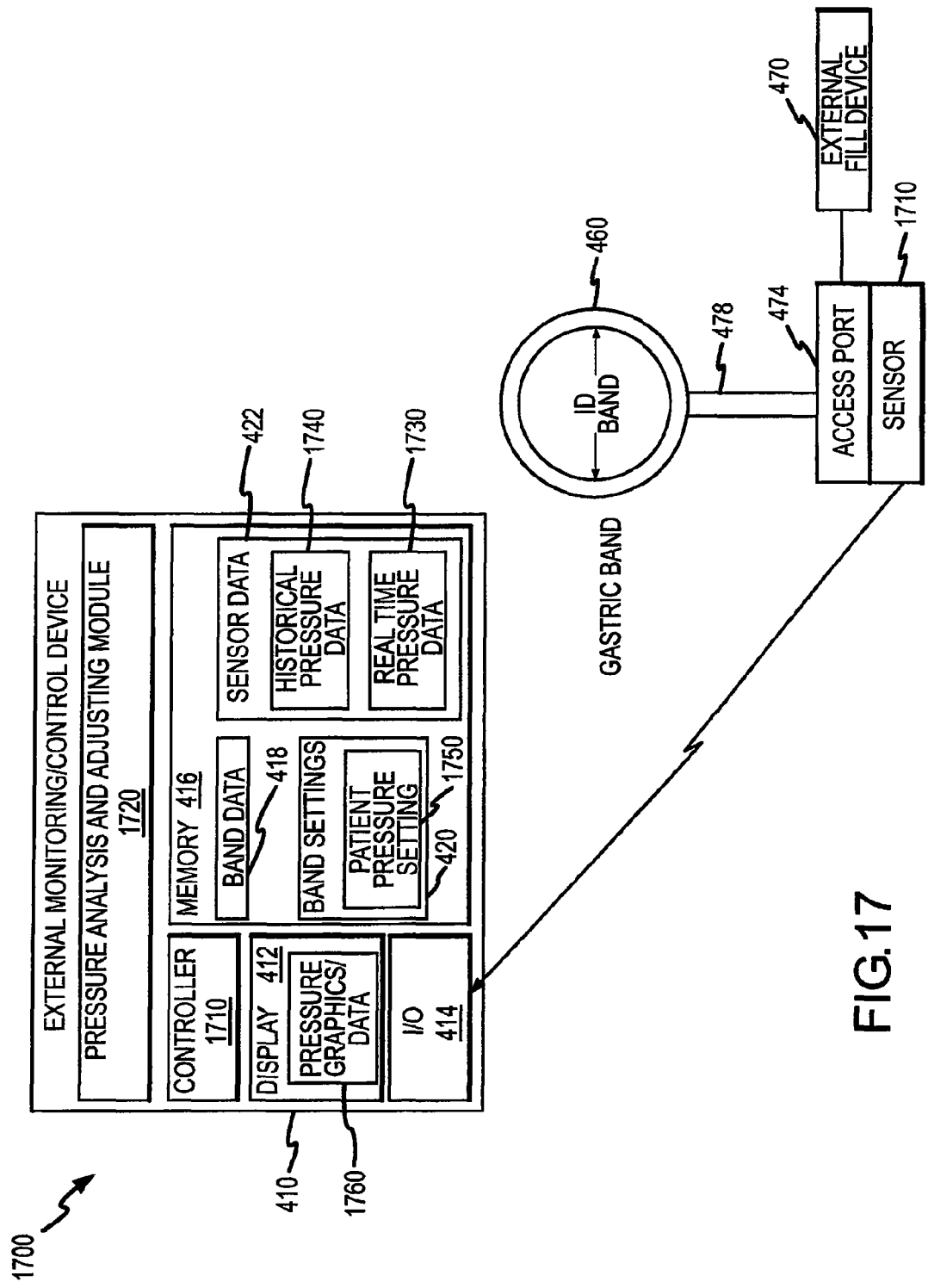
FIG. 17 is a block diagram similar to FIG. 16 showing a gastric band system according to another embodiment of the invention in which a pressure sensor is provided at or near an access port and a pressure analysis and adjusting module is used by an external control device for adjusting the fill of a gastric band.

In some cases, it is desirable for the software provided in the internal system 430 of system 1600 to be provided in an external device so as to provide a new diagnostic tool for use by physicians in adjusting and using gastric bands. FIG. 17 illustrates one such adjustment tool or system 1700. This tool or system 1700 can be used to determine an optimum level of adjustment or band fill based on the pressure response in the band 460 without requiring implantation of an internal adjustment system and its associated sensors. The controller (such as a hand held device) 410 may be configured to allow a physician to gradually increase the pressure in the band 460. To this end, the system 1700 includes a control device 410 (such as a handheld, desktop, or other electronic device) with a controller or processor 1710 that controls operation of display 410, I/O 414, and memory 416 and runs pressure analysis and adjusting module 1720, which may be a software application similar to module 1610 of FIG. 16. The memory is used for storing band data 418 as discussed above, band settings 420 that may include patient pressure settings 1750 including the ideal or target pressure setting that is determined by pressure analysis and adjusting module 1720, and sensor data 422 that may include real time pressure data or pressure readings from a sensor 1710 and historical pressure data 1740.

The system 1700 is also configured to allow pressure sensing of an implanted gastric band 460, and in the illustrated embodiment, this is achieved with a pressure sensor 1710 (e.g., a pressure transducer or the like) that is mounted in or near the access port 474 so as to be in contact with fluid in fill line 478 (and, therefore, the fluid in band 460). The sensor 1710 may also be provided in the external fill device 470 or a line between the port 474 and device 470. In yet other embodiments, the sensor 1710 is provided in the gastric band 460 itself. The sensor 1710 is preferably selected to communicate wirelessly or with a wired connection (e.g., a disconnectable connection) the sensed or read pressures to I/O 414.

As with the module 1610, the module 1720 is preferably configured to allow an operator such as a physician to readily establish a desirable or target pressure setting for the band 460. To this end the module 1720 may be configured to process pressure readings from the sensor 1710 at one or more fill volumes for the gastric band 460, such as when the pressure is being gradually, incrementally increased with the external fill device 470 (e.g., a needle). The module 1720 may function to generate graphs 1760 that are displayed by the controller 1710 on display 410 (such as the graph/curve 1810 of FIG. 18). This graph 1760 may be correlated with the patient in which the band 460 is implanted to identify the satiated fill levels and overfill levels (e.g., portions 1820 and 1830, 1840, respectively, of curve 1810). The module 1720 may take this data to determine pressure variations or standard deviations at each fill level. The module 1720 may act to correlate the variations at each fill level and provide a recommended target fill pressure that will result in pressure variations generally staying below a particular variation level (e.g., such as below 0.5 PSI, below 0.2 PSI, below 0.1 PSI, or some other variation identified by an operator of the device 410 of system 1700 or by the module 1720 itself). The data in memory 416 can be collected and downloaded to the physician's or operator's computer or computer system (e.g., a database in such system) to track pressures over time for the patient. In this manner, the system 1700 can be used for initially setting a pressure for the band 460 and also to later monitor pressure of the band 460 via sensor 1710 such as by queries to the sensor 1710.

While the embodiment of the system 1600 in FIG. 16 and other figures was generally described as self-adjusting, there are situations where it is desirable for these systems to be manually controlled. For example, it may be desirable for a physician or other operator to initiate pressure monitoring operations of the module 1610 so as to allow pressure readings 1620, 1650 to be observed on a graph 1666 or for other reasons. In one implementation, the system 1600 is adapted to be awakened by an operator of the external device 410, such as a technician/physician or the patient themselves. This may be useful when there is an obstruction in the stoma above the position of the band 460. Obstructions result in discomfort by the patient. In such a case, the device 410 may be operated to transmit a "wake up" signal over connection 426 to the internal band adjustment system 430. The module 1610 (or another software module) may process the wake up signal and trigger an auto-adjustment of the band 460. When an obstruction is present, the module 1610 will determine that the pressure readings 1620 from the sensor 450 are too high or above the target setting 1630 (or out of a desired pressure range relative to such setting 1630). The module 1610 responds to such high or out of range pressures by causing the controller 432 to operate the pump assembly 442 to decrease the volume of fluid in the band 460 (e.g., pumping fluid to the reservoir 448 or opening valves to allow flow). Such flow is performed until the obstruction passes and the pressure is out of range on the low side. At this point the module 1610 acts automatically to refill the band 460 with fluid from reservoir 448 (e.g., using power supply 444 to operate the pump 442).

Similarly, in some cases, it is desirable for the system 1600 to further include a "quick" release valve or other device to allow the pressure to be automatically or manually bled off from the band. For example, the system 1600 (or other systems described herein) may include a fluid release mechanism, which may include one or more valves or the like, that is remotely activated by an external controller to release a portion of the fluid from the cavity. Alternatively, the fluid release mechanism may be activated automatically such as by providing a safety valve (e.g., a one way check valve) in a line between the band or its lumen/cavity/shell that is selected to open at pressures over a particular maximum pressure that may be associated with the particular gastric band or with the patient and/or the treatment regimen. In other cases, the fluid release mechanism may be part of the internal adjustment system or be provided by additional components and be activated by commands from the internal controller, processing module, and/or by commands from an external controller or monitoring device. In these embodiments, the measured pressure can be reduced in the event that the external controller, the internal controller, or the check valve or similar device has determined that the measured pressure of the fluid in the cavity is greater than a upper limit of the operating pressure range or is greater than a second maximum pressure set above the upper limit (e.g., 1 to 2 PSI above the upper limit or other useful maximum allowable pressure for a band).

Figure 21:
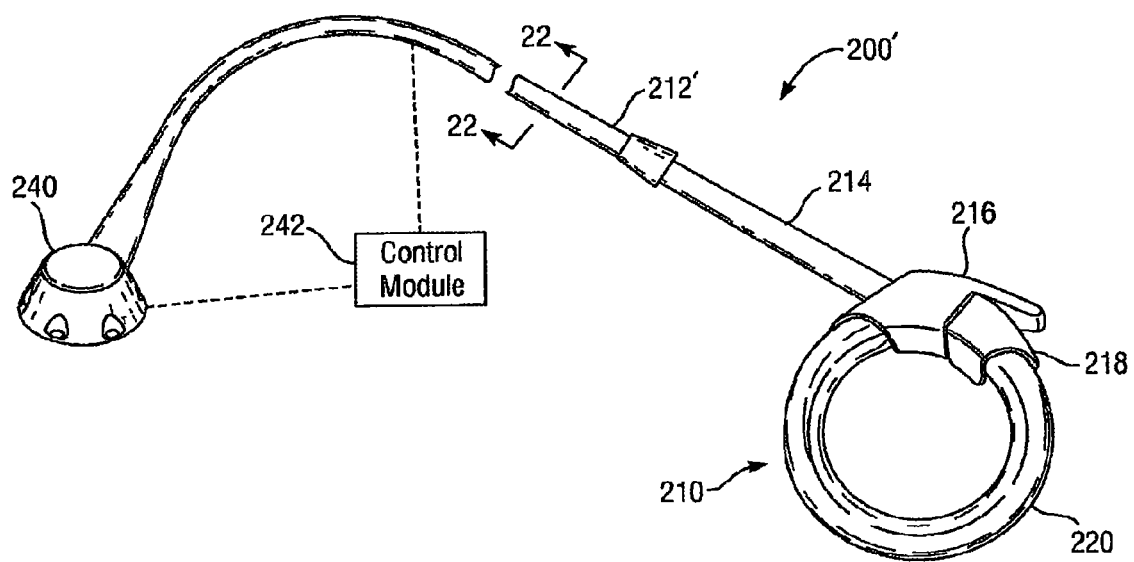
FIG. 21 illustrates a self-regulating gastric band system incorporating an expandable fluid reservoir incorporated in a fill tube extending to a fill port and schematically showing a control module in communication therewith.

FIGS. 19-21 illustrate an alternative embodiment of a self-regulating gastric band assembly 200' that is in many respects similar to the system 200 described with reference to FIGS. 2 and 3, and so like parts will retain the same element numbers. The assembly 200' includes an exemplary gastric band 210 that may used to implement the invention (such as for use as band 110 in system 100). The gastric band assembly 200' includes the gastric band 210 and an internal adjustment system (not shown) that generally includes a sensor for directly sensing properties of the band 210.

The gastric band 210 includes a fill tube or line 212' that provides a fluid connection between an access port 240 (FIG. 21) and an expandable or inflatable portion or lumen 226 in the band 210. A belt 214 with a recessed surface 215 and raised portion 218 are provided along with a buckle member 216 to allow initial forming of a circular loop or band of a particular initial size or inner diameter when the band 210 is implanted about a patient's stomach (e.g., to initially set the size of the band at 9 to 11 cm or another useful inner diameter) to provide an initial size of a stoma. To allow additional fine adjustment of the stoma, the gastric band includes an inflatable portion or member that abuts the outer surfaces of the stomach.

As shown, the gastric band 210 includes a shell or molded shell 220, a solid inner ring 222', and an inflatable portion, member, or balloon 224 made of an elastic or other material that can be increased in size and later reduced in size. The inflatable member 224 includes an internal lumen 226 for received volumes of fluid, e.g., saline or the like. As described above, the gastric band 210 may be configured to provide a local fluid reservoir for storing fluid for expanding or deflating the inflatable portion 224, though in this embodiment the reservoir is not shown as a lumen within the band itself. The inner ring 222' may be a separately formed structural member attached to the shell 220, or may be co-formed along with the shell 220.

As before, an internal adjustment system desirably includes a controller with memory, an internal power supply, and a pump assembly (not shown in FIGS. 19 and 20 but described with reference to FIGS. 4-10). A control module 242 shown schematically in FIG. 21 may function in the same manner as the previously described internal adjustment system 230 shown in FIG. 2, though with different flow paths. Namely, because the alternative fill tube 212' incorporates an exemplary fluid reservoir, described in detail below, the control module 242 preferably connects to the fill tube 212' at the end closest to the gastric band 210. For example, the control module 242 may include control valves in dual flow paths between the reservoir and internal lumen 226 of the gastric band 210 for alternately inflating and deflating the lumen as necessary or desired. Alternatively, the control module 242 could attach to the access port 240 as shown by the possible dashed line connections.

As described above, an implantable fluid reservoir for filling and deflating the inflatable lumen of the gastric band may be provided as a separate component in a housing associated with an internal band adjustment system (such as system 430 of FIG. 4) or the reservoir may be provided as a separate device, such as in the form of a balloon-like structure, that is provided proximate the internal band adjustment system or the band. Alternatively, the reservoir may be provided as part of the gastric band itself such as with the lumen 323 shown in FIG. 3. In the embodiments of FIGS. 22A-22H, various expandable reservoirs are provided along the fill tube 212'. Each will be described below, after a brief description of the use of such reservoirs. In a preferred embodiment, an elongated fluid reservoir extends along a substantial length of the fill tube 212', which is typically about 18 inches (46 cm) long.

One requirement of the fill tube 212' is that it has a low profile during implant so that it along with the belt 214 can easily slide through the buckle member 216 until the buckle snaps into the recessed surface 215. Consequently, reservoirs incorporated into the fill tube 212' are delivered in a collapsed or deflated configuration, and are later inflated, preferably via the access port 240, with saline or other such physiologic fluid. Once inflated, the reservoir remains available as a source of fluid and a drain container for increasing or decreasing the fluid level within the gastric band lumen. Fluid removed from the reservoir is pumped by the control module 242 via a fill/drain line (not shown) to the gastric band lumen 226 of the inflatable member 224 to reduce the size of the ID formed by the band about the stomach to reduce the size of the stoma formed in a patient. At other times, the control module 242 operates to pump fluid from the lumen 226 via the fill/drain line back to the reservoir and increase the ID formed by the band 210 about the stomach, thus increasing the size of the patient's stoma.

A first embodiment of a fill tube/reservoir is not shown but includes an elongated collapsible tube attached concentrically around or alongside the fill tube. The reservoir tube could be evacuated of air prior to implant of the system to cause it to closely conform around or against the fill tube and present a low profile for ease of band buckling. In a preferred embodiment, an elongated collapsible fluid reservoir extends along a substantial length of the fill tube. A "substantial length" means that the reservoir and fill tube extend in parallel for at least a few inches, potentially the entire length of the fill tube. The reservoir may be formed separately and connected to the fill tube during manufacture, or the two components may be formed simultaneously from the same material. Desirably, the fluid reservoir is expandable and the fluid reservoir and fill tube are co-extruded such that the reservoir collapses around at least a portion of the fill tube in a first, deflated state and expands to be substantially adjacent the fill tube in a second, inflated state of the reservoir.

Optionally a protective sheath surrounding the deflated reservoir tube could protect against accidental puncture by graspers and the like, and be removed after band placement and prior to saline expansion of the reservoir. The collapsible portion as well as the protective sheath could be made of silicone, polyurethane, PTFE or other flexible polymers.

Figure 22A:
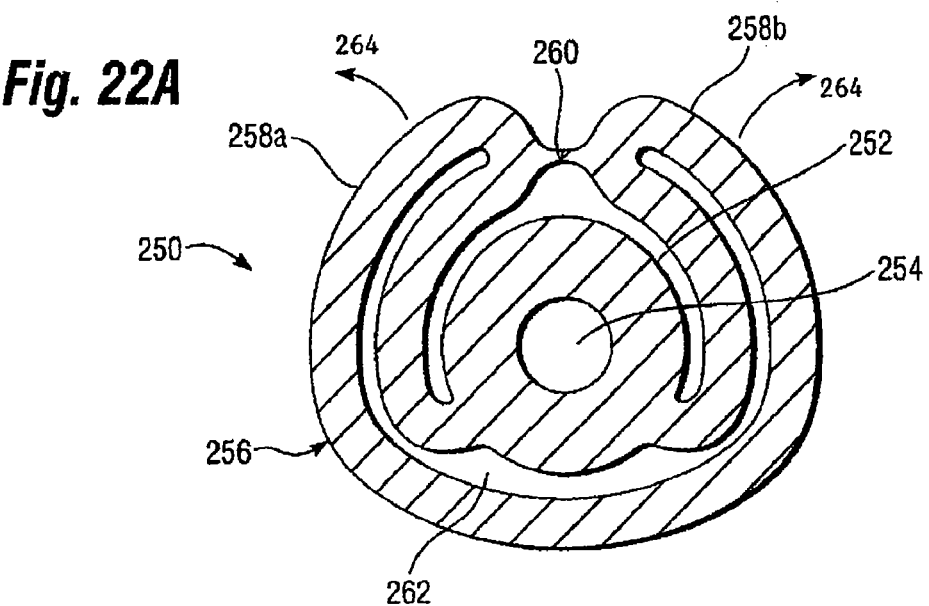
FIGS. 22A and 22B are transverse sectional views through the fill tube of the system of FIG. 21 showing an exemplary expandable fluid reservoir in a first, W-shaped deflated state and a second, inflated state.
Figure 22B:
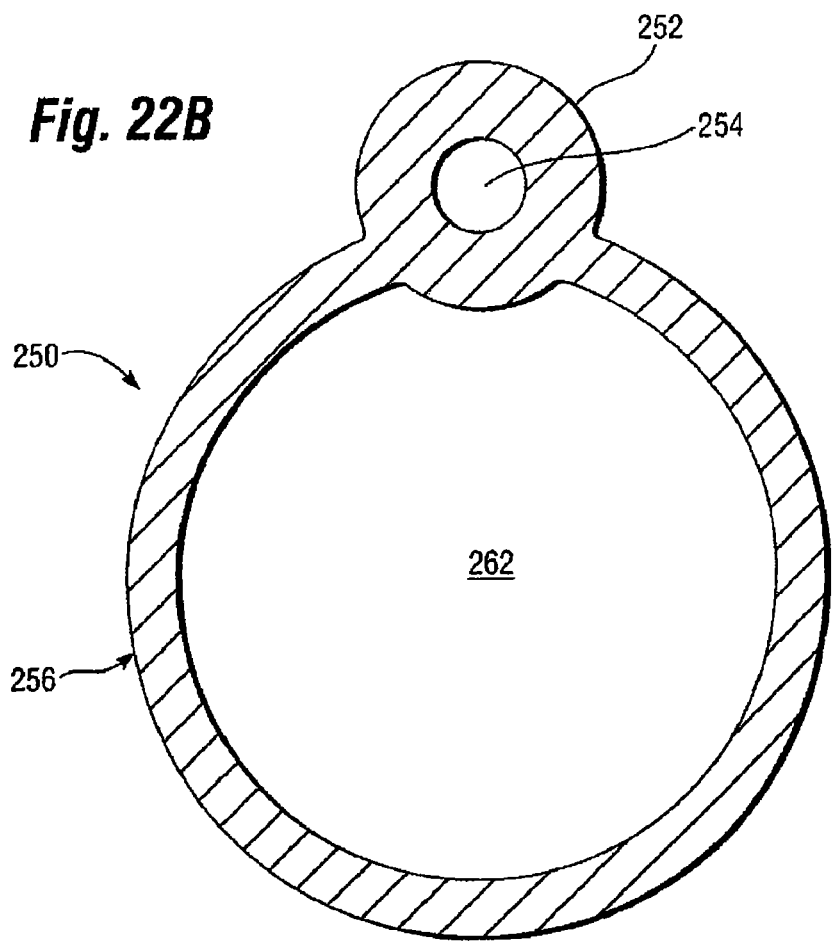

A second embodiment of a fill tube/reservoir 250 is shown in a first, deflated state in FIG. 22A, and a second, inflated state in FIG. 22B. A central tube 252 having an inner lumen 254 provides the fill tube functionality, and desirably remains open to permit later manual introduction of saline to the gastric band system if needed. An expandable reservoir 256 assumes a collapsed configuration in the first state of FIG. 22A, and an inflated substantially tubular configuration in the second state of FIG. 22B. In the collapsed configuration the reservoir 256 has a convoluted shape and folds around the central tube 252 in two wings 258a, 258b that connect at a temporary webbing 260. An inner reservoir lumen 262 has a sideways C-shape in the first, deflated state of the reservoir 250. As the addition of saline increases pressure within the lumen 262, the wings 258a, 258b tend to expand away from one another in the direction of arrows 264, ultimately rupturing the temporary webbing 260. A perforated line may be formed in the webbing 260 to facilitate this rupture. The convoluted first state of the reservoir 256 easily fits though the buckle member 216, whereupon the reservoir 256 may be filled with saline to assume the expanded second state. In one embodiment, the fill tube/reservoir 250 is formed as a co-extrusion with the wall thickness of the reservoir 256 less than that of the central tube 252.

Figure 22C:
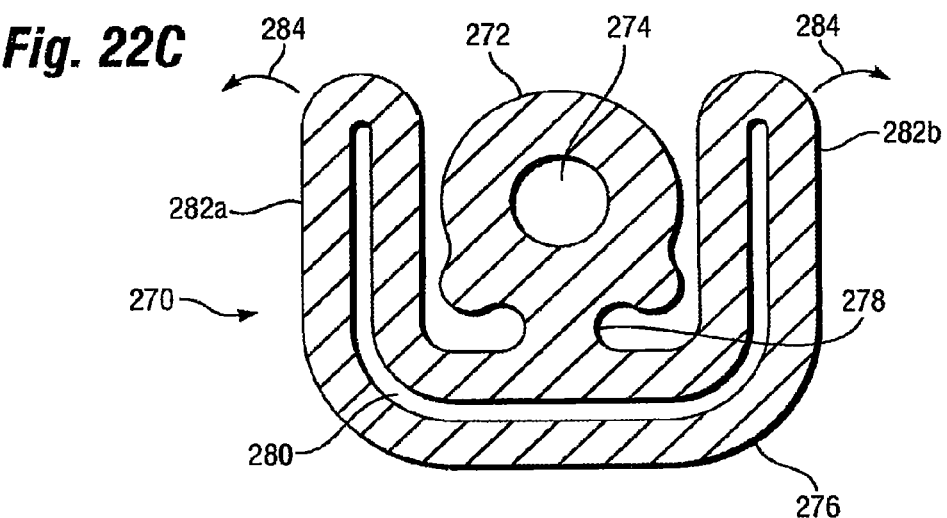
FIGS. 22C and 22D are transverse sectional views through the fill tube of the system of FIG. 21 showing an alternative expandable fluid reservoir in a first, U-shaped deflated state and a second, inflated state.
Figure 22D:
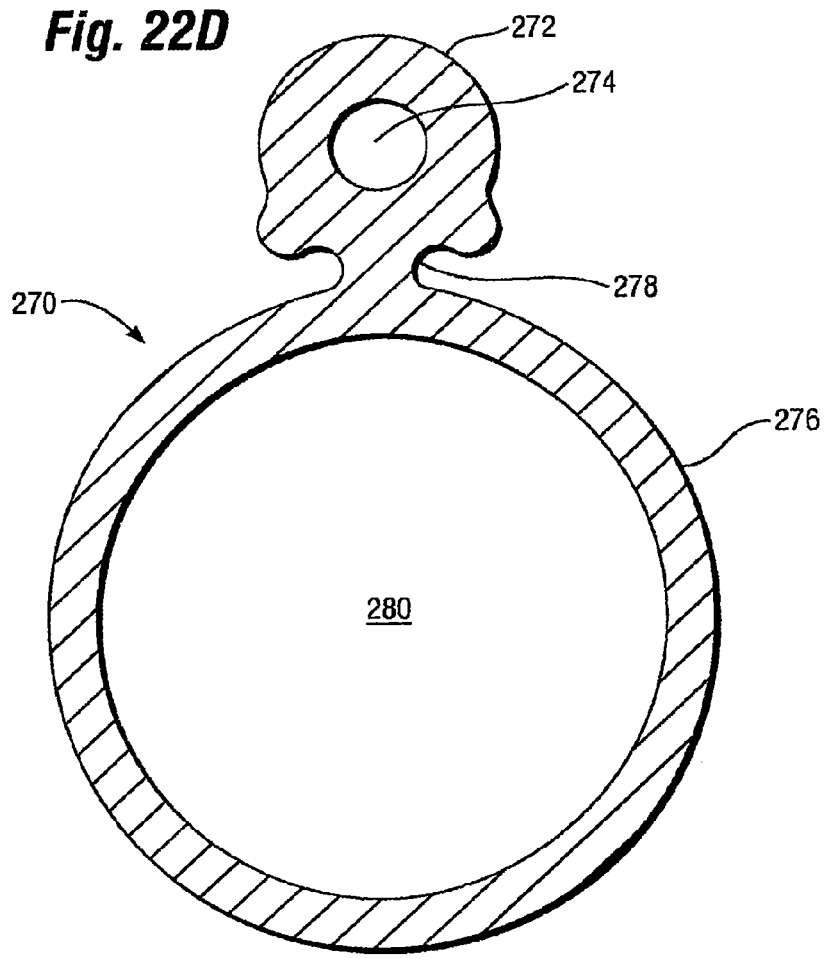

Another embodiment of a fill tube/reservoir 270 is shown in a first, deflated state in FIG. 22C, and a second, inflated state in FIG. 22D. A fill tube 272 having an inner lumen 274 connects to a reservoir 276 via a neck portion 278. A reservoir lumen 280 has a U-shape in the collapsed first state of FIG. 22C, with two wings 282a, 282b of the reservoir 276 extending on either side of the fill tube 272. Upon fluid inflation of the reservoir lumen 280, expansion forces 284 cause the wings 282a, 282b to spread out, ultimately forming the expanded second state of FIG. 22D.

Figure 22E:
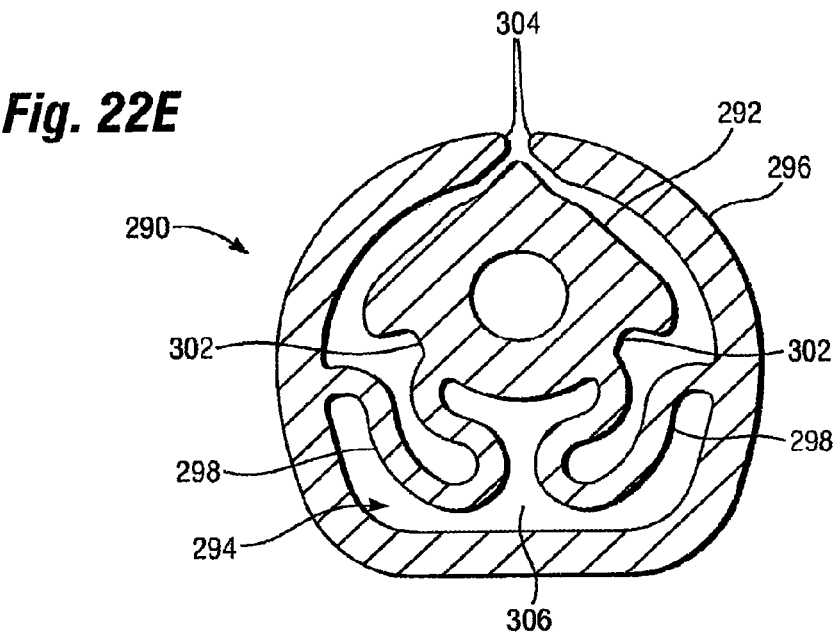
FIGS. 22E and 22F are transverse sectional views through the fill tube of the system of FIG. 21 showing an expandable fluid reservoir having an integral outer protective sheath in a first, deflated state and a second, inflated state.

FIGS. 22E/22F and 22G/22H illustrate two alternative fill tube/reservoirs having a protective outer shell or sheath surrounding the inflatable reservoir at all times. The outer sheath protects the reservoir from damage from graspers and the buckle member 216, and also shields the reservoir from pressure influences from the body. These two designs are exemplary only and many others are contemplated.

Figure 22F:
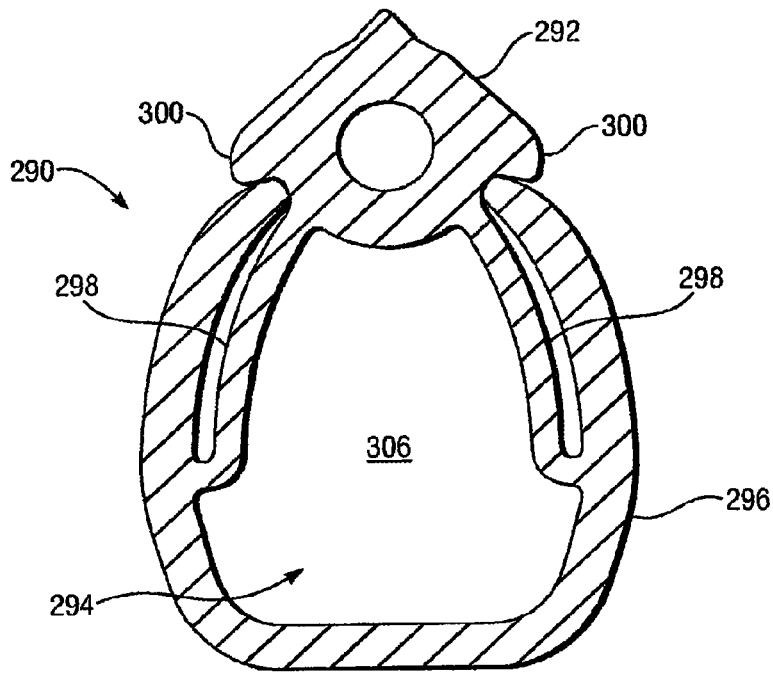

FIGS. 22E and 22F illustrate a fill tube/reservoir 290 wherein a fill tube 292 and reservoir 294 are contained within a split outer sheath 296 in a first, collapsed state, whereas the fill tube 292 emerges from within the sheath in a second, expanded state. The fill tube 292 connects to an inner surface of the sheath 296 via a pair of flexible walls 298 that form a part of the reservoir 294. The fill tube 292 has an arrowhead shape with outward shoulders 300 defining channels 302 for receiving free edges 304 of the outer sheath 296. A reservoir lumen 306 is defined partly by an inner surface of the sheath 296 and partly by the flexible walls 298. As will be clear from the figures, inflation of the reservoir lumen 306 forces the arrowhead-shaped fill tube 292 outward between the free edges 304 of the outer sheath 296 until the free edges, which are biased toward one another, clear the shoulders 300 and snap into the channels 302. This locking feature ensures that the protective outer sheath 296 remains at all times around the reservoir 294. In one embodiment, the fill tube/reservoir 290 and split outer sheath 296 are integrally formed as a co-extrusion with the wall thickness of the reservoir 294 less than that of the outer sheath 296.

Figure 22G:
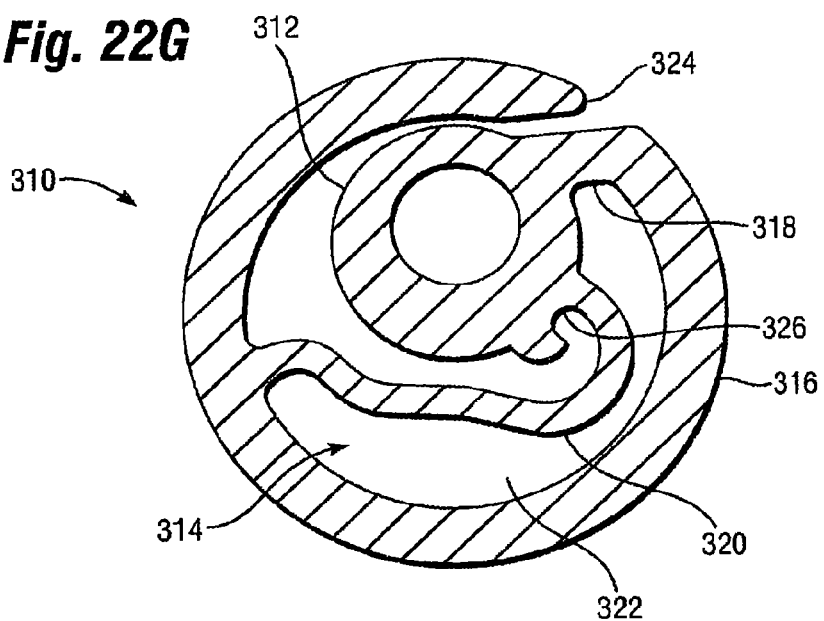
FIGS. 22G and 22H are transverse sectional views through the fill tube of the system of FIG. 21 showing an asymmetric expandable fluid reservoir having an integral outer protective sheath in a first, deflated state and a second, inflated state.
Figure 22H:
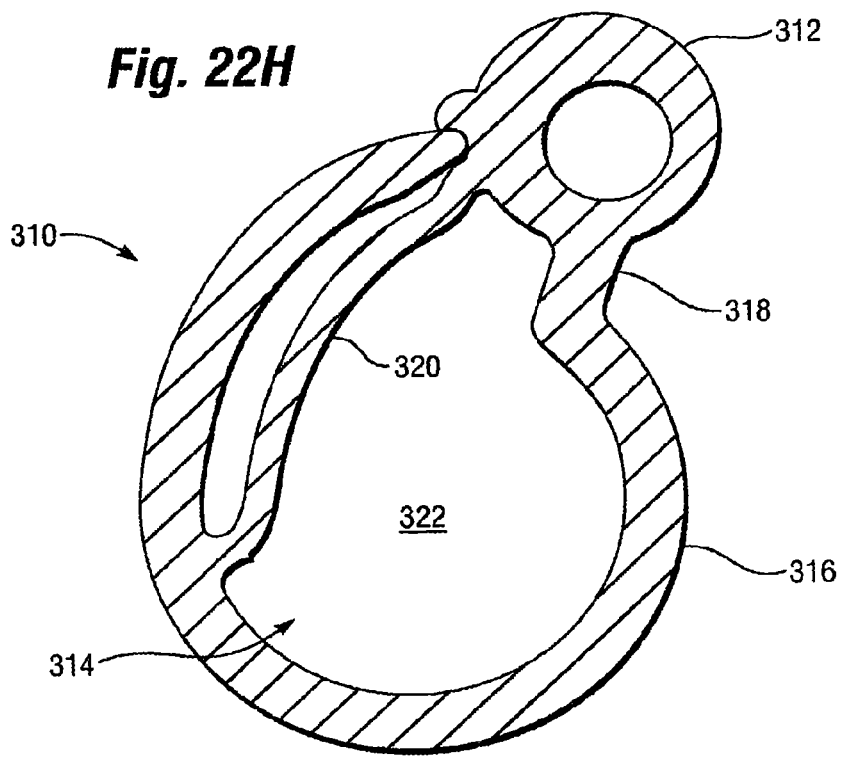

In an asymmetric embodiment of a fill tube/reservoir 310 seen in FIGS. 22G and 22H, a fill tube 312 and reservoir 314 are again contained within a protective outer sheath 316 in a first, collapsed state, whereas the fill tube 312 emerges from within the sheath in a second, expanded state. The fill tube 312 connects on one side via a web 318 and on another side via a flexible wall 320 to the outer sheath 316. A reservoir lumen 322 is defined partly by an inner surface of the sheath 316 and partly by the flexible wall 320. Upon inflation of the reservoir lumen 322, expansion forces cause the fill tube 312 to expand outward (rotate clockwise in the figures) until a free edge 324 of the outer sheath 316 engages a channel 326 formed on one side of the fill tube 312, as seen in FIG. 22H. Again, the locking feature ensures that the protective outer sheath 316 remains at all times around the reservoir 314. In one embodiment, the fill tube/reservoir 310 and outer sheath 316 are integrally formed as a co-extrusion with the wall thickness of the reservoir 314 less than that of the outer sheath 316.

Figure 22I:
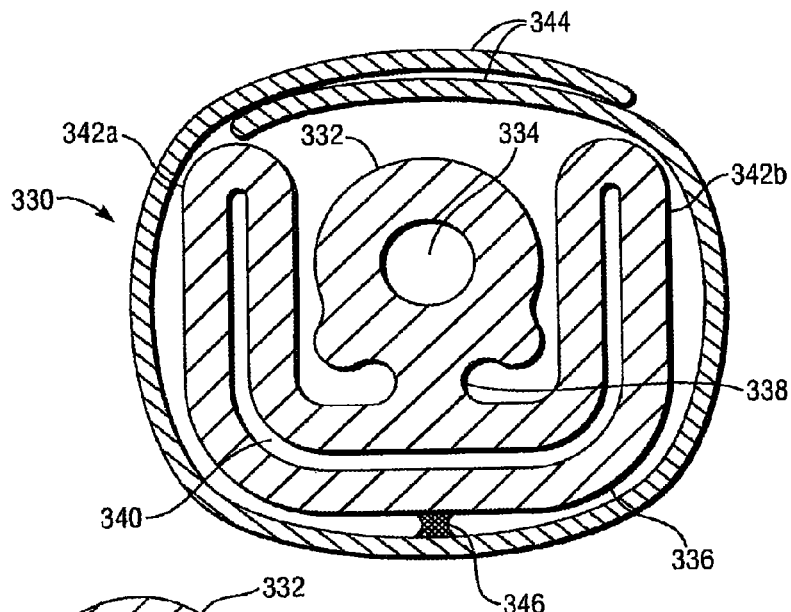
FIGS. 22I and 22J are transverse sectional views through the fill tube of the system of FIG. 21 showing an alternative expandable fluid reservoir having a separate outer protective sheath in a first, deflated state and a second, inflated state, as well as an outer protective sheath.
Figure 22J:
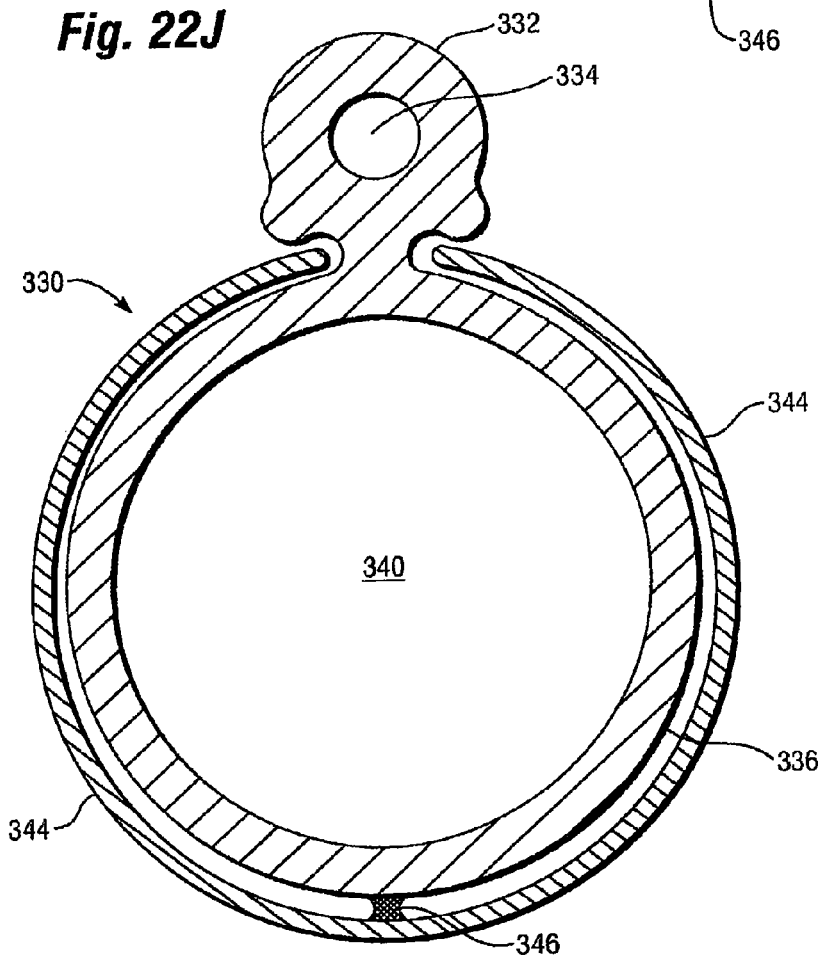

FIGS. 22I and 22J are transverse sectional views through a still further alternative fill tube/reservoir 330 with an alternative expandable fluid reservoir having a separate outer protective sheath. A central fill tube 332 having an inner lumen 334 is integrally connected to an expandable reservoir 336 via a bridge 338. The reservoir 336 assumes a collapsed configuration in the first state of FIG. 22I, and an inflated substantially tubular configuration in the second state of FIG. 22J. In the collapsed configuration the reservoir 336 has a U-shape like the reservoir 276 of FIGS. 22C and 22D, with two wings 342a, 342b extending on either side of the fill tube 332. Upon fluid inflation of a reservoir lumen 340, expansion forces cause the wings 338a, 338b to spread out, ultimately forming the expanded second state of FIG. 22J. The convoluted first state of the reservoir 336 easily fits though the buckle member 216, whereupon the reservoir 336 may be filled with saline to assume the expanded second state.

The fill tube/reservoir 330 also has a protective sheath 344 as described above, though in this embodiment the sheath is formed separately from the reservoir and is connected thereto during manufacture. That is, the sheath 344 comprises a longitudinally split tube that is biased into the compact configuration of FIG. 22I folded around the fill tube/reservoir 330 with its ends overlapping. The sheath 344 connects to the fill tube/reservoir 330 along a lower generatrix via a bead of adhesive or spot weld 346, as will be known by those of skill in the art. Expansion of the reservoir 336 spreads open the sheath 344, which remains protecting the reservoir at all times. This embodiment permits the sheath 344 to be made of a different material than the reservoir 336, which may be an advantage during manufacture.

Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as hereinafter claimed. To practice the invention, the gastric bands that are adjusted by the internal band adjustment systems of the invention may be external to the stomach as shown in FIG. 1, for example, or may be provided or implanted internal to the stomach and/or esophagus, i.e., the gastric bands regulated according to the invention may be intragastric bands. Such an intragastric band may take the same or similar form of the bands described with reference to FIGS. 1-10 or another form (such as forms described in the following incorporated reference), and for example, may be attached and/or implanted in a number of ways such as shown in U.S. Pat. Appl. Publ. No. 2005/0192601, which is incorporated herein by reference.

While the invention has been described in its preferred embodiments, it is to be understood that the words which have been used are words of description and not of limitation. Therefore, changes may be made within the appended claims without departing from the true scope of the invention.

What is claimed is:

1. An adjustable gastric band system for implantation in a body of an overweight patient, the system comprising:
 a gastric band having an inflatable member for positioning around an upper portion of a stomach of the patient;
 a tube in fluid communication with the inflatable member of the gastric band, the tube having an exterior surface forming a channel thereon;
 an expandable reservoir in fluid communication with the inflatable member of the gastric band, the reservoir having a collapsed configuration to facilitate implantation of the reservoir and an expanded configuration for storing a fluid to adjust the inflatable member of the gastric band; and
 a protective outer sheath coupled to the reservoir, the protective outer sheath having a locking member surrounding the channel of the tube when the reservoir is in the collapsed configuration, the locking member configured to engage with the channel when the reservoir is in the expanded configuration.

2. The system of claim 1 wherein the reservoir is disposed around a portion of the tube when in the collapsed configuration and the reservoir is configured to be substantially adjacent to the tube when in the expanded configuration.

3. The system of claim 2 further comprising a temporary webbing for maintaining the reservoir in the collapsed configuration around the portion of the tube, the temporary webbing configured to rupture when the reservoir expands to the expanded configuration.

4. The system of claim 3 further comprising a perforation formed in the temporary webbing to facilitate the rupture of the temporary webbing.

5. The system of claim 1 wherein the reservoir is evacuated of air when in the collapsed configuration.

6. The system of claim 1 wherein the reservoir and the tube are formed simultaneously from the same material.

7. The system of claim 1 wherein the protective outer sheath is integrally formed as a co-extrusion with the tube or the reservoir.

8. The system of claim 1 wherein the protective outer sheath is manufactured separately from the reservoir.

9. An implantable gastric band system for the treatment of obesity in a patent, the system comprising:
 an adjustable gastric band having an inflatable portion, the inflatable portion configured to encircle an upper portion of a stomach of the patient;
 a tube in fluid communication with the inflatable portion of the gastric band, the tube having an exterior surface defining a channel thereon;
 an expandable reservoir defining a lumen therein, the lumen in fluid communication with the inflatable portion of the gastric band, the lumen having a collapsed state to facilitate implantation of the reservoir and an expanded state for containing a fluid to adjust the inflatable portion of the gastric band; and
 an outer shell surrounding the lumen and the tube when the lumen is in the collapsed state, a portion of the outer shell configured to engage with the channel of the tube when the lumen is in the expanded state.

10. The system of claim 9 further comprising a flexible wall coupled between the tube and the outer shell, the flexible wall forming a part of the reservoir.

11. The system of claim 10 wherein the lumen is defined partly by an inner surface of the outer shell and partly by the flexible wall.

12. The system of claim 11 wherein the outer shell has a thickness greater than the thickness of the flexible wall.

13. The system of claim 9 wherein the outer shell surrounds the lumen at all times.

14. The system of claim 9 wherein the outer shell is made of a flexible polymer.

15. The system of claim 14 wherein the flexible polymer is silicon, polyurethane or PTFE.

16. An implantable gastric band system for the treatment of an overweight patent, the system comprising:
- an adjustable gastric band having an inflatable lumen configured to be positioned around a stomach of the patient;
- an expandable reservoir in fluid communication with the inflatable lumen of the gastric band, the reservoir having a deflated configuration to facilitate implantation of the reservoir and an inflated configuration for storing a fluid to adjust the inflatable lumen of the gastric band;
- a tube in fluid communication with the inflatable lumen of the gastric band, the tube coupled to the reservoir along a first length of the tube; and
- a protective sheath surrounding the reservoir and the tube when the reservoir is in the deflated configuration, the protective sheath having an engagement element configured to engage with tube along the first length of the tube when the reservoir is in the inflated configuration.

17. The system of claim 16 further comprising an adhesive bead coupling the protective sheath to the reservoir.

18. The system of claim 16 wherein the protective sheath is made of a different material than the reservoir.

19. The system of claim 16 wherein the protective sheath is manufactured separately from the reservoir.

20. The system of claim 16 wherein the protective sheath comprises a longitudinally split tube having a first end and a second end, the first end overlapping the second end when the reservoir is in the deflated configuration.

* * * * *